US011351023B2

(12) United States Patent
Hamill et al.

(10) Patent No.: US 11,351,023 B2
(45) Date of Patent: Jun. 7, 2022

(54) SYSTEMS AND METHODS FOR PROTECTING THE CEREBRAL VASCULATURE

(71) Applicant: BOSTON SCIENTIFIC SCIMED, INC., Maple Grove, MN (US)

(72) Inventors: Whittaker Ian Hamill, Petaluma, CA (US); Shih-hsiung Albert Yuan, Pleasanton, CA (US); Daniel W. Fifer, Windsor, CA (US); David J. Blaeser, Champlin, MN (US)

(73) Assignee: Claret Medical, Inc., Santa Rosa, CA (US)

( * ) Notice: Subject to any disclaimer, the term of this patent is extended or adjusted under 35 U.S.C. 154(b) by 169 days.

(21) Appl. No.: 16/546,535

(22) Filed: Aug. 21, 2019

(65) Prior Publication Data

US 2020/0060802 A1    Feb. 27, 2020

Related U.S. Application Data

(60) Provisional application No. 62/720,816, filed on Aug. 21, 2018.

(51) Int. Cl.
*A61F 2/01* (2006.01)
*A61M 39/06* (2006.01)
(Continued)

(52) U.S. Cl.
CPC .............. *A61F 2/012* (2020.05); *A61B 90/39* (2016.02); *A61F 2/0105* (2020.05); *A61M 39/06* (2013.01);
(Continued)

(58) Field of Classification Search
CPC .. A61F 2/01; A61F 2/011; A61F 2/012; A61F 2/013; A61F 2/0105;
(Continued)

(56) References Cited

U.S. PATENT DOCUMENTS 3,472,230 A   10/1969   Fogarty
4,619,246 A   10/1986   Molgaard-Nielsen et al.
(Continued)

FOREIGN PATENT DOCUMENTS

DE    10049812 A1   4/2002
EP     1400257 A2   3/2004
(Continued)

OTHER PUBLICATIONS

International Search Report and Written Opinion dated Dec. 2, 2019 for International Application No. PCT/US2019/047434.
(Continued)

*Primary Examiner* — Tuan V Nguyen
(74) *Attorney, Agent, or Firm* — Seager, Tufte & Wickhem LLP

(57) ABSTRACT

Vascular filters and deflectors and methods for filtering bodily fluids. A blood filtering assembly can capture embolic material dislodged or generated during an endovascular procedure to inhibit or prevent the material from entering the cerebral vasculature. A blood deflecting assembly can deflect embolic material dislodged or generated during an endovascular procedure to inhibit or prevent the material from entering the cerebral vasculature.

17 Claims, 23 Drawing Sheets

(51) Int. Cl.
*A61B 90/00* (2016.01)
*A61M 25/10* (2013.01)

(52) U.S. Cl.
CPC ....... *A61B 2090/3966* (2016.02); *A61F 2/011* (2020.05); *A61F 2002/016* (2013.01); *A61M 25/104* (2013.01); *A61M 2039/062* (2013.01)

(58) Field of Classification Search
CPC ........ A61F 2230/006; A61F 2230/0006; A61F 2230/0015; A61F 2230/0019; A61F 2230/0067; A61F 2/016
See application file for complete search history.

(56) References Cited

U.S. PATENT DOCUMENTS

| | | |
|---|---|---|
| 4,630,609 A | 12/1986 | Chin |
| 4,650,466 A | 3/1987 | Luther |
| 4,706,671 A | 11/1987 | Weinrib |
| 4,723,549 A | 2/1988 | Wholey et al. |
| 4,873,978 A | 10/1989 | Ginsburg |
| 5,108,419 A | 4/1992 | Reger |
| 5,192,286 A | 3/1993 | Phan et al. |
| 5,200,248 A | 4/1993 | Thompson et al. |
| 5,329,923 A | 7/1994 | Lundquist |
| 5,348,545 A | 9/1994 | Shani et al. |
| 5,381,782 A | 1/1995 | DeLaRama et al. |
| 5,395,327 A | 3/1995 | Lundquist et al. |
| 5,613,980 A | 3/1997 | Chauhan |
| 5,624,430 A | 4/1997 | Eton et al. |
| 5,662,671 A | 9/1997 | Barbut et al. |
| 5,680,873 A | 10/1997 | Berg et al. |
| 5,707,389 A | 1/1998 | Louw et al. |
| 5,766,151 A | 6/1998 | Valley et al. |
| 5,779,716 A | 7/1998 | Cano et al. |
| 5,800,525 A * | 9/1998 | Bachinski .............. A61F 2/01 623/1.1 |
| 5,814,064 A | 9/1998 | Daniel et al. |
| 5,827,324 A | 10/1998 | Cassell |
| 5,833,650 A | 11/1998 | Imran |
| 5,848,964 A | 12/1998 | Samuels |
| 5,897,529 A | 4/1999 | Ponzi |
| 5,897,819 A | 4/1999 | Miyata et al. |
| 5,910,154 A | 6/1999 | Tsugita et al. |
| 5,910,364 A | 6/1999 | Miyata et al. |
| 5,911,734 A | 6/1999 | Tsugita et al. |
| 5,935,139 A | 8/1999 | Bates |
| 5,941,896 A * | 8/1999 | Kerr .................. A61F 2/0105 606/200 |
| 5,980,555 A | 11/1999 | Barbut et al. |
| 5,989,281 A | 11/1999 | Barbut et al. |
| 5,993,469 A | 11/1999 | McKenzie et al. |
| 6,001,118 A | 12/1999 | Daniel et al. |
| 6,010,522 A | 1/2000 | Barbut et al. |
| 6,027,520 A | 2/2000 | Tsugita et al. |
| 6,042,598 A | 3/2000 | Tsugita et al. |
| 6,045,547 A | 4/2000 | Ren et al. |
| 6,051,014 A | 4/2000 | Jang |
| 6,080,140 A | 6/2000 | Swaminathan et al. |
| 6,083,239 A | 7/2000 | Addis |
| 6,096,053 A | 8/2000 | Bates |
| 6,099,534 A | 8/2000 | Bates et al. |
| 6,120,494 A | 9/2000 | Jonkman |
| 6,126,673 A | 10/2000 | Kim et al. |
| 6,129,739 A | 10/2000 | Khosravi |
| 6,142,987 A | 11/2000 | Tsugita |
| 6,146,396 A | 11/2000 | Konya |
| 6,152,946 A | 11/2000 | Broome et al. |
| 6,171,328 B1 | 1/2001 | Addis |
| 6,179,851 B1 | 1/2001 | Barbut et al. |
| 6,179,861 B1 | 1/2001 | Khosravi et al. |
| 6,203,561 B1 | 3/2001 | Ramee et al. |
| 6,214,026 B1 | 4/2001 | Lepak et al. |
| 6,235,045 B1 | 5/2001 | Barbut et al. |
| 6,245,087 B1 | 6/2001 | Addis |
| 6,245,088 B1 | 6/2001 | Lowery |
| 6,245,089 B1 | 6/2001 | Daniel et al. |
| 6,264,663 B1 | 7/2001 | Cano |
| 6,270,513 B1 | 8/2001 | Tsugita et al. |
| 6,277,138 B1 | 8/2001 | Levinson et al. |
| 6,287,321 B1 | 9/2001 | Jang |
| 6,290,710 B1 | 9/2001 | Cryer et al. |
| 6,309,399 B1 | 10/2001 | Barbut et al. |
| 6,325,815 B1 | 12/2001 | Kusleika et al. |
| 6,336,934 B1 | 1/2002 | Gilson et al. |
| 6,336,116 B1 | 2/2002 | Brooks et al. |
| 6,361,545 B1 * | 3/2002 | Macoviak ........ A61B 17/12109 606/200 |
| 6,364,900 B1 | 4/2002 | Heuser |
| 6,371,970 B1 | 4/2002 | Khosravi |
| 6,371,971 B1 | 4/2002 | Tsugita et al. |
| 6,375,628 B1 | 4/2002 | Zadno-Azizi et al. |
| 6,383,174 B1 | 5/2002 | Eder |
| 6,383,205 B1 | 5/2002 | Samson |
| 6,440,120 B1 | 8/2002 | Maahs |
| 6,454,799 B1 | 9/2002 | Schreck |
| 6,485,502 B2 | 11/2002 | Don Michael |
| 6,499,487 B1 | 12/2002 | McKenzie et al. |
| 6,517,559 B1 | 2/2003 | O'Connell |
| 6,530,939 B1 | 3/2003 | Hopkins et al. |
| 6,537,297 B2 | 3/2003 | Tsugita et al. |
| 6,544,279 B1 | 4/2003 | Hopkins et al. |
| 6,558,356 B2 | 5/2003 | Barbut |
| 6,589,263 B1 | 7/2003 | Hopkins et al. |
| 6,595,983 B2 | 7/2003 | Voda |
| 6,605,102 B1 | 8/2003 | Mazzocchi |
| 6,616,679 B1 | 9/2003 | Khosravi et al. |
| 6,620,148 B1 | 9/2003 | Tsugita |
| 6,620,182 B1 | 9/2003 | Khosravi et al. |
| 6,648,837 B2 | 11/2003 | Kato et al. |
| 6,663,652 B2 | 12/2003 | Daniel et al. |
| 6,676,682 B1 | 1/2004 | Tsugita et al. |
| 6,712,834 B2 | 3/2004 | Yassour et al. |
| 6,712,835 B2 | 3/2004 | Mazzocchi |
| 6,719,717 B1 | 4/2004 | Johnson et al. |
| 6,726,621 B2 | 4/2004 | Suon et al. |
| 6,726,651 B1 | 4/2004 | Robinson et al. |
| 6,726,701 B2 | 4/2004 | Gilson |
| 6,740,061 B1 | 5/2004 | Oslund |
| 6,817,999 B2 | 11/2004 | Berube et al. |
| 6,830,579 B2 | 12/2004 | Barbut |
| 6,843,798 B2 | 1/2005 | Kusleika et al. |
| 6,872,216 B2 | 3/2005 | Daniel |
| 6,881,194 B2 | 4/2005 | Miyata et al. |
| 6,887,258 B2 | 5/2005 | Denison et al. |
| 6,905,490 B2 | 6/2005 | Parodi |
| 6,907,298 B2 | 6/2005 | Smits et al. |
| 6,958,074 B2 | 10/2005 | Russell |
| 6,969,396 B2 | 11/2005 | Krolik et al. |
| 7,011,094 B2 | 3/2006 | Rapacki et al. |
| 7,048,752 B2 | 5/2006 | Mazzocchi |
| 7,094,249 B1 | 8/2006 | Broome |
| 7,115,134 B2 | 10/2006 | Chambers |
| 7,160,255 B2 | 1/2007 | Saadat |
| 7,169,161 B2 | 1/2007 | Bonnette et al. |
| 7,169,165 B2 | 1/2007 | Belef et al. |
| 7,182,757 B2 | 2/2007 | Miyata et al. |
| 7,214,237 B2 | 5/2007 | Don Michael |
| 7,278,974 B2 | 10/2007 | Kato et al. |
| 7,303,575 B2 | 12/2007 | Ogle |
| 7,306,618 B2 | 12/2007 | Demond et al. |
| 7,313,445 B2 | 12/2007 | McVenes et al. |
| 7,323,001 B2 | 1/2008 | Clubb et al. |
| 7,329,278 B2 | 2/2008 | Seguin et al. |
| 7,399,308 B2 | 7/2008 | Borillo et al. |
| 7,410,491 B2 | 8/2008 | Hopkins |
| 7,493,154 B2 | 2/2009 | Bonner et al. |
| 7,559,925 B2 | 7/2009 | Goldfarb et al. |
| 7,572,272 B2 | 8/2009 | Denison et al. |
| 7,621,904 B2 | 11/2009 | McFerran et al. |
| 7,722,634 B2 | 5/2010 | Panetta et al. |
| 7,766,961 B2 | 8/2010 | Patel et al. |
| 7,918,859 B2 | 4/2011 | Katoh et al. |
| 7,922,732 B2 | 4/2011 | Mazzocchi et al. |

(56) References Cited

U.S. PATENT DOCUMENTS

| | | |
|---|---|---|
| 7,976,562 B2 | 7/2011 | Bressler et al. |
| 7,998,104 B2 | 8/2011 | Chang |
| 8,002,790 B2 | 8/2011 | Brady et al. |
| 8,021,351 B2 | 9/2011 | Boldenow et al. |
| 8,052,713 B2 | 11/2011 | Khosravi et al. |
| 8,092,483 B2 | 1/2012 | Galdonik et al. |
| 8,206,412 B2 | 6/2012 | Galdonik et al. |
| 8,372,108 B2 | 2/2013 | Lashinski |
| 8,382,788 B2 | 2/2013 | Galdonik |
| 8,460,335 B2 | 6/2013 | Carpenter |
| 8,518,073 B2 | 8/2013 | Lashinski |
| 8,753,370 B2 | 6/2014 | Lashinski |
| 8,876,796 B2 | 11/2014 | Fifer et al. |
| 8,974,489 B2 | 3/2015 | Lashinski |
| 9,017,364 B2 | 4/2015 | Fifer et al. |
| 9,055,997 B2 | 6/2015 | Fifer et al. |
| 9,259,306 B2 | 2/2016 | Fifer et al. |
| 9,326,843 B2 | 5/2016 | Lee et al. |
| 9,345,565 B2 | 5/2016 | Fifer et al. |
| 9,480,548 B2 | 11/2016 | Carpenter |
| 9,492,264 B2 | 11/2016 | Fifer et al. |
| 9,566,144 B2 | 2/2017 | Purcell et al. |
| 9,636,205 B2 | 5/2017 | Lee et al. |
| 9,943,395 B2 | 4/2018 | Fifer et al. |
| 9,980,805 B2 | 5/2018 | Fifer |
| 2001/0041858 A1 | 11/2001 | Ray et al. |
| 2002/0022858 A1 | 2/2002 | Demond et al. |
| 2002/0026145 A1 | 2/2002 | Bagaoisan et al. |
| 2002/0055767 A1 | 5/2002 | Forde et al. |
| 2002/0068015 A1 | 6/2002 | Polaschegg et al. |
| 2002/0077596 A1 | 6/2002 | McKenzie et al. |
| 2002/0091409 A1 | 7/2002 | Sutton et al. |
| 2002/0095170 A1 | 7/2002 | Krolik et al. |
| 2002/0095172 A1 | 7/2002 | Mazzocchi et al. |
| 2002/0123761 A1 | 9/2002 | Barbut et al. |
| 2002/0161394 A1 | 10/2002 | Macoviak et al. |
| 2002/0165571 A1 | 11/2002 | Herbert et al. |
| 2002/0165573 A1 | 11/2002 | Barbut |
| 2003/0100919 A1 | 5/2003 | Hopkins et al. |
| 2003/0130684 A1 | 7/2003 | Brady et al. |
| 2003/0144686 A1 | 7/2003 | Martinez et al. |
| 2003/0171770 A1 | 9/2003 | Kusleika et al. |
| 2003/0199960 A1 | 10/2003 | Paskar |
| 2003/0216774 A1* | 11/2003 | Larson .................. A61F 2/0105 606/200 |
| 2004/0002730 A1 | 1/2004 | Denison et al. |
| 2004/0006370 A1 | 1/2004 | Tsugita |
| 2004/0044350 A1 | 3/2004 | Martin et al. |
| 2004/0044360 A1 | 3/2004 | Lowe |
| 2004/0064092 A1 | 4/2004 | Tsugita et al. |
| 2004/0093015 A1 | 5/2004 | Ogle |
| 2004/0167565 A1 | 8/2004 | Beulke et al. |
| 2004/0193206 A1 | 9/2004 | Gerberding |
| 2004/0215167 A1 | 10/2004 | Belson |
| 2004/0215230 A1 | 10/2004 | Frazier |
| 2004/0220611 A1 | 11/2004 | Ogle |
| 2004/0225321 A1 | 11/2004 | Krolik et al. |
| 2004/0230220 A1 | 11/2004 | Osborne |
| 2004/0243175 A1 | 12/2004 | Don Michael |
| 2004/0254601 A1 | 12/2004 | Eskuri |
| 2004/0254602 A1 | 12/2004 | Lehe et al. |
| 2005/0010285 A1 | 1/2005 | Lambrecht et al. |
| 2005/0065397 A1 | 3/2005 | Saadat et al. |
| 2005/0080356 A1 | 4/2005 | Dapolito et al. |
| 2005/0085847 A1 | 4/2005 | Galdonik et al. |
| 2005/0101987 A1 | 5/2005 | Salahieh |
| 2005/0131449 A1 | 6/2005 | Salahieh et al. |
| 2005/0137696 A1 | 6/2005 | Salahieh |
| 2005/0177132 A1 | 8/2005 | Lentz et al. |
| 2005/0209631 A1 | 9/2005 | Galdonik et al. |
| 2005/0277976 A1 | 12/2005 | Galdonik et al. |
| 2006/0015136 A1 | 1/2006 | Besselink |
| 2006/0015138 A1 | 1/2006 | Gertner |
| 2006/0030876 A1* | 2/2006 | Peacock, III ........... A61F 2/013 606/200 |
| 2006/0030877 A1 | 2/2006 | Martinez et al. |
| 2006/0041188 A1 | 2/2006 | Dirusso et al. |
| 2006/0047301 A1 | 3/2006 | Ogle |
| 2006/0089618 A1 | 4/2006 | McFerran et al. |
| 2006/0089666 A1 | 4/2006 | Linder et al. |
| 2006/0100658 A1 | 5/2006 | Obana et al. |
| 2006/0100662 A1 | 5/2006 | Daniel et al. |
| 2006/0129180 A1 | 6/2006 | Tsugita et al. |
| 2006/0135961 A1 | 6/2006 | Rosenman et al. |
| 2006/0136043 A1 | 6/2006 | Cully et al. |
| 2006/0149350 A1 | 7/2006 | Patel et al. |
| 2006/0161241 A1 | 7/2006 | Barbut et al. |
| 2006/0200047 A1 | 9/2006 | Galdonik et al. |
| 2006/0200191 A1 | 9/2006 | Zadno-Azizi |
| 2006/0259066 A1 | 11/2006 | Euteneuer |
| 2007/0005131 A1 | 1/2007 | Taylor |
| 2007/0043259 A1 | 2/2007 | Jaffe et al. |
| 2007/0060944 A1 | 3/2007 | Boldenow et al. |
| 2007/0088244 A1 | 4/2007 | Miller et al. |
| 2007/0088383 A1 | 4/2007 | Pal et al. |
| 2007/0173878 A1 | 7/2007 | Heuser |
| 2007/0191880 A1 | 8/2007 | Cartier et al. |
| 2007/0208302 A1 | 9/2007 | Webster et al. |
| 2007/0244504 A1 | 10/2007 | Keegan et al. |
| 2008/0004687 A1 | 1/2008 | Barbut |
| 2008/0033467 A1 | 2/2008 | Miyamoto et al. |
| 2008/0058860 A1 | 3/2008 | Demond et al. |
| 2008/0065145 A1 | 3/2008 | Carpenter |
| 2008/0065147 A1 | 3/2008 | Mazzocchi et al. |
| 2008/0086110 A1 | 4/2008 | Galdonik et al. |
| 2008/0109088 A1 | 5/2008 | Galdonik et al. |
| 2008/0125848 A1 | 5/2008 | Kusleika et al. |
| 2008/0154153 A1 | 6/2008 | Heuser |
| 2008/0172066 A9 | 6/2008 | Galdonik et al. |
| 2008/0188884 A1 | 8/2008 | Gilson et al. |
| 2008/0234722 A1 | 9/2008 | Bonnette et al. |
| 2008/0262442 A1 | 10/2008 | Carlin et al. |
| 2008/0300462 A1 | 12/2008 | Intoccia et al. |
| 2009/0024072 A1 | 1/2009 | Criado et al. |
| 2009/0024153 A1 | 1/2009 | Don Michael |
| 2009/0069840 A1 | 3/2009 | Hallisey |
| 2009/0198269 A1 | 8/2009 | Hannes et al. |
| 2009/0203962 A1 | 8/2009 | Miller et al. |
| 2009/0254172 A1 | 10/2009 | Grewe et al. |
| 2009/0287187 A1 | 11/2009 | Legaspi et al. |
| 2009/0326575 A1 | 12/2009 | Galdonik |
| 2010/0004633 A1 | 1/2010 | Rothe et al. |
| 2010/0010476 A1 | 1/2010 | Galdonik et al. |
| 2010/0063537 A1 | 3/2010 | Ren et al. |
| 2010/0106182 A1 | 4/2010 | Patel et al. |
| 2010/0179583 A1 | 7/2010 | Carpenter et al. |
| 2010/0179584 A1 | 7/2010 | Carpenter et al. |
| 2010/0179585 A1 | 7/2010 | Carpenter et al. |
| 2010/0179647 A1 | 7/2010 | Carpenter et al. |
| 2010/0185216 A1 | 7/2010 | Garrison et al. |
| 2010/0191276 A1 | 7/2010 | Lashinski |
| 2010/0211095 A1 | 8/2010 | Carpenter |
| 2010/0228280 A1 | 9/2010 | Groothius et al. |
| 2010/0312268 A1 | 12/2010 | Belson |
| 2010/0324589 A1 | 12/2010 | Carpenter et al. |
| 2011/0066221 A1 | 3/2011 | White et al. |
| 2011/0282379 A1 | 11/2011 | Lee et al. |
| 2012/0046739 A1 | 2/2012 | von Oepen et al. |
| 2012/0095500 A1 | 4/2012 | Heuser |
| 2012/0203265 A1 | 8/2012 | Heuser |
| 2013/0123835 A1 | 5/2013 | Anderson et al. |
| 2013/0131714 A1 | 5/2013 | Wang et al. |
| 2013/0231694 A1 | 9/2013 | Lashinski |
| 2013/0238010 A1 | 9/2013 | Johnson et al. |
| 2014/0052170 A1 | 2/2014 | Heuser et al. |
| 2014/0094843 A1 | 4/2014 | Heuser |
| 2014/0100597 A1 | 4/2014 | Wang et al. |
| 2014/0249567 A1 | 9/2014 | Adams et al. |
| 2014/0276922 A1 | 9/2014 | McLain et al. |
| 2015/0039016 A1 | 2/2015 | Naor et al. |
| 2015/0073533 A1 | 3/2015 | Kassab et al. |
| 2015/0230910 A1 | 8/2015 | Lashinski et al. |
| 2015/0335416 A1 | 11/2015 | Fifer et al. |
| 2016/0058541 A1 | 3/2016 | Schotzko et al. |

(56) References Cited

U.S. PATENT DOCUMENTS

| | | |
|---|---|---|
| 2016/0262864 A1 | 9/2016 | Von Mangoldt et al. |
| 2016/0310255 A1 | 10/2016 | Purcell et al. |
| 2017/0042658 A1 | 2/2017 | Lee et al. |
| 2017/0112609 A1 | 4/2017 | Purcell et al. |
| 2017/0181834 A1 | 6/2017 | Fifer et al. |
| 2017/0202657 A1 | 7/2017 | Lee et al. |
| 2018/0177582 A1 | 6/2018 | Lashinski |
| 2018/0235742 A1 | 8/2018 | Fields et al. |
| 2019/0125513 A1* | 5/2019 | Purcell .................. A61F 2/013 |
| 2019/0183628 A1* | 6/2019 | Purcell .............. A61M 25/0147 |

FOREIGN PATENT DOCUMENTS

| | | |
|---|---|---|
| EP | 1253871 B1 | 2/2007 |
| EP | 2303384 A2 | 4/2011 |
| EP | 2391303 A2 | 12/2011 |
| EP | 2480165 A2 | 8/2012 |
| EP | 2658476 A1 | 11/2013 |
| EP | 2387427 B1 | 8/2014 |
| EP | 2859864 A1 | 4/2015 |
| JP | 2003505216 A | 2/2003 |
| JP | 2003526451 A | 9/2003 |
| JP | 2003290231 A | 10/2003 |
| JP | 3535098 B2 | 6/2004 |
| JP | 2006500187 A | 1/2006 |
| JP | 2008511401 A | 4/2008 |
| JP | 2008515463 A | 5/2008 |
| JP | 2011525405 A | 9/2011 |
| WO | 9923976 A1 | 5/1999 |
| WO | 0021604 A1 | 4/2000 |
| WO | 0108743 A1 | 2/2001 |
| WO | 0167989 A2 | 9/2001 |
| WO | 2004026175 A1 | 4/2004 |
| WO | 2005118050 A2 | 12/2005 |
| WO | 2006026371 A1 | 3/2006 |
| WO | 2006076505 A2 | 7/2006 |
| WO | 2008033845 A2 | 3/2008 |
| WO | 2008100790 A2 | 8/2008 |
| WO | 2008113857 A2 | 9/2008 |
| WO | 2009032834 A1 | 3/2009 |
| WO | 2010008451 A2 | 1/2010 |
| WO | 2010081025 A1 | 7/2010 |
| WO | 2010083527 A2 | 7/2010 |
| WO | 2010088520 A2 | 8/2010 |
| WO | 2011034718 A2 | 3/2011 |
| WO | 2011017103 A2 | 10/2011 |
| WO | 2012092377 A1 | 7/2012 |
| WO | 2014145892 A2 | 9/2014 |
| WO | 2018156655 A1 | 8/2018 |

OTHER PUBLICATIONS

Internet Archive Wayback Machine; Fiber Innovative Technology: FIT Capabilities; downloaded from http://web.archive.org/web/20010217040848/http://www.fitfibers.com/capabilities.htm (Archived Feb. 17, 2001; printed on Dec. 12, 2016).

Internet Archive Wayback Machine; Fiber Innovative Technology: 4DG Fibers; downloaded from http://web.archive.org/web/20011030070010/http://fitfibers.com/4DG_Fibers.htm (Archived Oct. 30, 2001; printed on Dec. 12, 2016).

Internet Archive Wayback Machine; Fiber Innovative Technology: FIT Products; downloaded from http://web.archive.org/web/20010408003529/http://www.fitfibers.com/product.htm (Archived Apr. 8, 2001; printed on Dec. 12, 2016).

\* cited by examiner

SYSTEMS AND METHODS FOR PROTECTING THE CEREBRAL VASCULATURE

CROSS-REFERENCE TO RELATED APPLICATIONS

This application claims the benefit of priority under 35 U.S.C. § 119 to U.S. Provisional Application Ser. No. 62/720,816, filed Aug. 21, 2018, the entirety of which is incorporated herein by reference.

TECHNICAL FIELD

In general, the present disclosure relates to medical devices for filtering blood. And, more particularly, in certain embodiments, to a method and a system of filters and deflectors for protecting the cerebral arteries from emboli, debris and the like dislodged during an endovascular or cardiac procedure.

BACKGROUND

There are four arteries that carry oxygenated blood to the brain, i.e., the right and left vertebral arteries, and the right and left common carotid arteries. Various procedures conducted on the human body, e.g., transcatheter aortic valve replacement (TAVR), aortic valve valvuloplasty, carotid artery stenting, closure of the left atrial appendage, mitral valve annuloplasty, mitral valve replacement, mitral valve repair, thoracic endovascular aortic repair (TEVAR), etc., can cause and/or dislodge native or foreign materials, which dislodged bodies can travel into one or more of the cerebral arteries resulting in, inter alia, stroke. Therefore, filtering the innominate artery, right subclavian artery, right brachiocephalic artery, right common carotid artery, left vertebral artery, and left subclavian artery at aortic branch arches or at the arches of said arteries may be useful to prevent dislodged materials from migrating to the cerebral area.

Thromboembolic disorders, such as stroke, pulmonary embolism, peripheral thrombosis, atherosclerosis, and the like affect many people. These disorders are a major cause of morbidity and mortality in the United States and throughout the world. Thromboembolic events are characterized by an occlusion of a blood vessel. The occlusion can be caused by a clot which is viscoelastic or jelly-like and comprises platelets, fibrinogen, and other clotting proteins.

Percutaneous aortic valve replacement procedures have become popular, but stroke rates related to this procedure are between two and twenty percent. During catheter delivery and valve implantation, plaque or other material may be dislodged from the vasculature and may travel through the carotid circulation and into the brain. When an artery is occluded by a clot or other embolic material, tissue ischemia (lack of oxygen and nutrients) develops. The ischemia progresses to tissue infarction (cell death) if the occlusion persists. Infarction does not develop or is greatly limited if the flow of blood is reestablished rapidly. Failure to reestablish blood-flow can lead to the loss of limb, angina pectoris, myocardial infarction, stroke, or even death.

Reestablishing blood flow and removal of the thrombus is highly desirable. Surgical techniques and medicaments to remove or dissolve obstructing material have been developed, but exposing a subject to surgery may be traumatic and is best avoided when possible. Additionally, the use of certain devices carry risks such as the risk of dislodging foreign bodies, damaging the interior lining of the vessel as the catheter is being manipulated, blood thinning, etc.

A variety of filtration or deflection devices have been proposed, to prevent entry of debris into the cerebral circulation. Some isolate only the brachiocephalic artery and left common carotid, while others might additionally isolate the left Subclavian but typically through the use of multiple catheters. Others are said to isolate all three arteries leading to the cerebral circulation, from a single catheter, but the catheter is introduced via the femoral artery and none have achieved adoption.

The need thus remains for a simple, single catheter to enable endovascular isolation of the complete cerebral circulation, preferably from an access point other than the femoral artery.

SUMMARY

The present invention provides a three vessel cerebral protection system.

In a first example, an embolic protection system for isolating the cerebral vasculature may comprise a first protection device having a proximal portion configured to remain outside the body and a distal portion and a second protection device having a proximal portion configured to remain outside the body and a distal portion. The distal portion of the first protection device may comprise a proximal sheath, a proximal self-expanding filter assembly radially within the proximal sheath, a distal sheath, and a distal self-expanding filter assembly radially within the distal sheath. The distal portion of the second protection device may comprise an outer sheath, an inner member radially within the outer sheath, and a third filter assembly radially within the outer sheath and coupled to the inner member.

Alternatively or additionally to any of the examples above, in another example, the inner member may comprise a wire.

Alternatively or additionally to any of the examples above, in another example, the third filter assembly of the second protection device may have a generally self-expanding tubular main body portion defining a lumen extending from a distal end to a proximal end thereof.

Alternatively or additionally to any of the examples above, in another example, the generally tubular main body portion may be configured to be positioned over an ostium of the left subclavian artery.

Alternatively or additionally to any of the examples above, in another example, the wire may be woven into the third self-expanding filter assembly adjacent a distal end of the third filter assembly.

Alternatively or additionally to any of the examples above, in another example, a distal edge of a filter element of the third filter assembly may be folded proximally over the wire.

Alternatively or additionally to any of the examples above, in another example, the wire may comprise a plurality of wires each having a distal end coupled to a distal end of the third filter assembly.

Alternatively or additionally to any of the examples above, in another example, proximal actuation of the plurality of wires may be configured to invert the third filter assembly.

Alternatively or additionally to any of the examples above, in another example, the wire may be interwoven into the third filter assembly to form an expandable support structure having a first cross-sectional dimension in a first expanded configuration exterior to the outer sheath and a second cross-sectional dimension in a second collapsed configuration within the outer sheath, the second cross-sectional dimension smaller than the first cross-sectional dimension.

Alternatively or additionally to any of the examples above, in another example, the embolic protection system may further comprise an angiographic catheter radially within the outer sheath, wherein the angiographic catheter may have an outer dimension greater than the second cross-sectional dimension of the expandable support structure.

Alternatively or additionally to any of the examples above, in another example, a distal end of the angiographic catheter may be configured to engage the expandable support structure when the expandable support structure is in the second collapsed configuration within the outer sheath.

Alternatively or additionally to any of the examples above, in another example, the third filter assembly may comprise an expandable support structure and a filter element.

Alternatively or additionally to any of the examples above, in another example, the expandable support structure may comprise a plurality of longitudinally extending legs, the filter element coupled to the plurality of longitudinally extending legs adjacent to a distal end of the filter element.

Alternatively or additionally to any of the examples above, in another example, the expandable support structure may comprise a first longitudinally extending leg, a second longitudinally extending leg, a support ring having a first portion and a second portion, and a pair of hinges movingly coupling the first and second portions of the support ring to the first and second longitudinally extending legs.

Alternatively or additionally to any of the examples above, in another example, the support ring may be coupled to the filter element adjacent to a distal end of the filter element.

In another example, an embolic protection system for isolating the cerebral vasculature may comprise a first protection device having a proximal portion configured to remain outside the body and a distal portion and a second protection device having a proximal portion configured to remain outside the body and a distal portion. The distal portion of the first protection device may comprise a proximal sheath, a proximal self-expanding filter assembly radially within the proximal sheath, a distal sheath, and a distal self-expanding filter assembly radially within the distal sheath. The distal portion of the second protection device may comprise an outer sheath, a wire radially within the outer sheath, and a third filter assembly radially within the outer sheath and coupled to the wire.

Alternatively or additionally to any of the examples above, in another example, the third filter assembly of the second protection device may have a generally self-expanding tubular main body portion defining a lumen extending from a distal end to a proximal end thereof.

Alternatively or additionally to any of the examples above, in another example, the generally tubular main body portion may be configured to be positioned over an ostium of the left subclavian artery.

Alternatively or additionally to any of the examples above, in another example, the wire may be woven into the third self-expanding filter assembly adjacent a distal end of the third filter assembly.

Alternatively or additionally to any of the examples above, in another example, a distal edge of a filter element of the third filter assembly may be folded proximally over the wire.

Alternatively or additionally to any of the examples above, in another example, the wire may comprise a plurality of wires each having a distal end coupled to a distal end of the third filter assembly.

Alternatively or additionally to any of the examples above, in another example, proximal actuation of the plurality of wires may be configured to invert the third filter assembly.

Alternatively or additionally to any of the examples above, in another example, the wire may be interwoven into the third filter assembly to form an expandable support structure having a first cross-sectional dimension in a first expanded configuration exterior to the outer sheath and a second cross-sectional dimension in a second collapsed configuration within the outer sheath, the second cross-sectional dimension smaller than the first cross-sectional dimension.

Alternatively or additionally to any of the examples above, in another example, the embolic protection system may further comprise an angiographic catheter radially within the outer sheath, wherein the angiographic catheter may have an outer dimension greater than the second cross-sectional dimension of the expandable support structure.

Alternatively or additionally to any of the examples above, in another example, a distal end of the angiographic catheter may be configured to engage the expandable support structure when the expandable support structure is in the second collapsed configuration within the outer sheath.

In another example, an embolic protection system for isolating the cerebral vasculature may comprise a first protection device having a proximal portion configured to remain outside the body and a distal portion and a second protection device having a proximal portion configured to remain outside the body and a distal portion. The distal portion of the first protection device may comprise a proximal sheath, a proximal self-expanding filter assembly radially within the proximal sheath, a distal sheath, and a distal self-expanding filter assembly radially within the distal sheath. The distal portion of the second protection device may comprise an outer sheath, an inner member radially within the outer sheath, and a third filter assembly radially within the outer sheath and coupled to a distal end of the inner member, the third filter assembly including an expandable support structure and a filter element.

Alternatively or additionally to any of the examples above, in another example, the expandable support structure may comprise a plurality of longitudinally extending legs, the filter element coupled to the plurality of longitudinally extending legs adjacent to a distal end of the filter element.

Alternatively or additionally to any of the examples above, in another example, the expandable support structure may comprise a first longitudinally extending leg, a second longitudinally extending leg, a support ring having a first portion and a second portion, and a pair of hinges movingly coupling the first and second portions of the support ring to the first and second longitudinally extending legs.

Alternatively or additionally to any of the examples above, in another example, the support ring may be coupled to the filter element adjacent to a distal end of the filter element.

In another example, an embolic protection system for isolating the cerebral vasculature may comprise a first protection device having a proximal portion configured to remain outside the body and a distal portion and a second protection device having a proximal portion configured to remain outside the body and a distal portion. The distal portion of the first protection device may comprise a proximal sheath, a proximal self-expanding filter assembly radially within the proximal sheath, a distal sheath, and a distal self-expanding filter assembly radially within the distal sheath. The distal portion of the second protection device may comprise an outer sheath and a third filter assembly coupled to and extending distally from a distal end of the outer sheath, the third filter assembly including an expandable support structure and a filter element.

Alternatively or additionally to any of the examples above, in another example, the expandable support structure may comprise a plurality of legs, a distal ring, and a pull wire, wherein a distal end of each leg of the plurality of legs may be coupled to the distal ring and a proximal end of each leg of the plurality of legs may be coupled to the distal end of the outer sheath.

Alternatively or additionally to any of the examples above, in another example, a distal end of the pull wire may be coupled to the distal ring and proximal actuation of the pull wire may be configured to proximally displace the distal ring relative to the outer sheath and deflect the plurality of legs radially outward to expand the filter element.

Alternatively or additionally to any of the examples above, in another example, the expandable support structure may comprise include a longitudinally extending leg and a distal hoop.

Alternatively or additionally to any of the examples above, in another example, the embolic protection system may further comprise a radially inward extending deployment member coupled to a proximal portion of the longitudinally extending leg and a pull wire coupled to the proximal portion of the longitudinally extending leg.

Alternatively or additionally to any of the examples above, in another example, a proximal portion of the pull wire may be disposed between the outer sheath and an inner liner.

In another example, a method of inhibiting embolic material from entering cerebral vasculature may comprise deploying a first filter system comprising a first filter and a second filter. Deploying the first filter system may comprise deploying the first filter in a brachiocephalic artery and deploying the second filter in a left common carotid artery. The method may further comprise deploying a second filter system including an outer sheath and a third filter. Deploying the second filter system may comprise deploying the third filter in the left subclavian artery. The method may further comprise advancing an angioplasty catheter though a central lumen of the third filter and resheathing the third filter into the outer sheath.

Alternatively or additionally to any of the examples above, in another example, advancing the angioplasty catheter may deploy the third filter.

Alternatively or additionally to any of the examples above, in another example, resheathing the third filter may comprise advancing the outer sheath.

Alternatively or additionally to any of the examples above, in another example, resheathing the third filter may comprise inverting the third filter.

Alternatively or additionally to any of the examples above, in another example, inverting the third filter may comprise pulling a pull wire attached to a distal portion of the third filter.

Alternatively or additionally to any of the examples above, in another example, the third filter may be mounted to an inner shaft extending through the outer sheath.

Alternatively or additionally to any of the examples above, in another example, advancing the angioplasty catheter may comprise advancing the angioplasty catheter through the inner shaft.

Alternatively or additionally to any of the examples above, in another example, the second filter system may comprise an expandable structure at a proximal portion of the third filter.

Alternatively or additionally to any of the examples above, in another example, the method may further comprise expanding the expandable structure from a collapsed configuration, in which an inner diameter of the expandable structure is less than an outer diameter of the angioplasty catheter, to an expanded configuration, in which the inner diameter of the expandable structure is greater than the outer diameter of the angioplasty catheter.

Alternatively or additionally to any of the examples above, in another example, the third filter may be supported with the angioplasty catheter.

Alternatively or additionally to any of the examples above, in another example, the second filter system may comprise a projection extending into the central lumen of the third filter.

Alternatively or additionally to any of the examples above, in another example, deploying the third filter may comprise advancing the angioplasty catheter against the projection.

In another example, a system for inhibiting embolic material from entering cerebral vasculature may comprise a first filter system comprising a first filter configured to be deployed in a brachiocephalic artery and a second filter configured to be deployed in a left common carotid artery, a second filter system comprising a third filter configured to be deployed from an outer sheath, and an angioplasty catheter configured to be advanced through the second filter system.

Alternatively or additionally to any of the examples above, in another example, the system may further comprise a pull wire attached to a distal portion of the third filter.

Alternatively or additionally to any of the examples above, in another example, the system may further comprise an inner shaft extending through the outer sheath, third filter mounted to the inner shaft.

Alternatively or additionally to any of the examples above, in another example, the second filter system may comprise an expandable structure at a proximal portion of the third filter, the expandable structure configured to be expanded from a collapsed configuration, in which an inner diameter of the expandable structure is less than an outer diameter of the angioplasty catheter, to an expanded configuration, in which the inner diameter of the expandable structure is greater than the outer diameter of the angioplasty catheter.

Alternatively or additionally to any of the examples above, in another example, the second filter system may comprise a projection extending into the central lumen of the third filter.

In another example, a three vessel cerebral protection catheter may comprise an elongate flexible tubular sheath, having a proximal end and a distal end, an inner member extending through the sheath, and a filter assembly. The filter assembly may comprise a filter membrane carried between the inner member and the sheath and an aortic support hoop configured to seal the membrane against the wall of the aorta. The filter assembly may be configured to isolate the aorta from the brachiocephalic, left common carotid and left subclavian arteries when a distal portion of the filter assembly is expanded within the left subclavian artery and the sheath is retracted to expose the membrane.

Alternatively or additionally to any of the examples above, in another example, the filter assembly may further comprise structural elements to reinforce the aortic support hoop.

Alternatively or additionally to any of the examples above, in another example, the filter assembly may comprise a distal filter element configured to be expanded within the left subclavian.

Alternatively or additionally to any of the examples above, in another example, the distal filter element may comprise a frame, the frame being connected to the aortic support hoop by a support connector.

Alternatively or additionally to any of the examples above, in another example, when deployed, the aortic support hoop may be angled to extend from the aorta to the left subclavian artery.

Alternatively or additionally to any of the examples above, in another example, the filter assembly may comprise a distal anchor configured to anchor the distal portion of the filter assembly in the left subclavian artery.

Alternatively or additionally to any of the examples above, in another example, the filter assembly may further comprise a support leg extending from the aortic support hoop to the distal portion of the filter assembly.

In another example, a method of inhibiting embolic material from entering cerebral vasculature may comprise deploying a filter system comprising an outer sheath and a filter, wherein deploying the filter system comprises deploying the filter in the left subclavian artery. The method may further comprise advancing an angioplasty catheter though a central lumen of the filter and resheathing the filter into the outer sheath.

Alternatively or additionally to any of the examples above, in another example, advancing the angioplasty catheter may deploy the filter.

Alternatively or additionally to any of the examples above, in another example, resheathing the filter may comprise advancing the outer sheath.

Alternatively or additionally to any of the examples above, in another example, resheathing the filter may comprise inverting the filter.

Alternatively or additionally to any of the examples above, in another example, inverting the filter may comprise pulling a pull wire attached to a distal portion of the filter.

Alternatively or additionally to any of the examples above, in another example, the filter may be mounted to an inner shaft extending through the outer sheath.

Alternatively or additionally to any of the examples above, in another example, advancing the angioplasty catheter may comprise advancing the angioplasty catheter through the inner shaft.

Alternatively or additionally to any of the examples above, in another example, the filter system may comprise an expandable structure at a proximal portion of the filter.

Alternatively or additionally to any of the examples above, in another example, the method may further comprise expanding the expandable structure from a collapsed configuration, in which an inner diameter of the expandable structure is less than an outer diameter of the angioplasty catheter, to an expanded configuration, in which the inner diameter of the expandable structure is greater than the outer diameter of the angioplasty catheter.

Alternatively or additionally to any of the examples above, in another example, the method may further comprise supporting the filter with the angioplasty catheter.

Alternatively or additionally to any of the examples above, in another example, the filter system may comprise a projection extending into the central lumen of the filter.

Alternatively or additionally to any of the examples above, in another example, deploying the filter may comprise advancing the angioplasty catheter against the projection.

The above summary of exemplary embodiments is not intended to describe each disclosed embodiment or every implementation of the present disclosure.

BRIEF DESCRIPTION OF THE DRAWINGS

The invention may be more completely understood in consideration of the following detailed description of various embodiments in connection with the accompanying drawings, in which.

Figure 1:
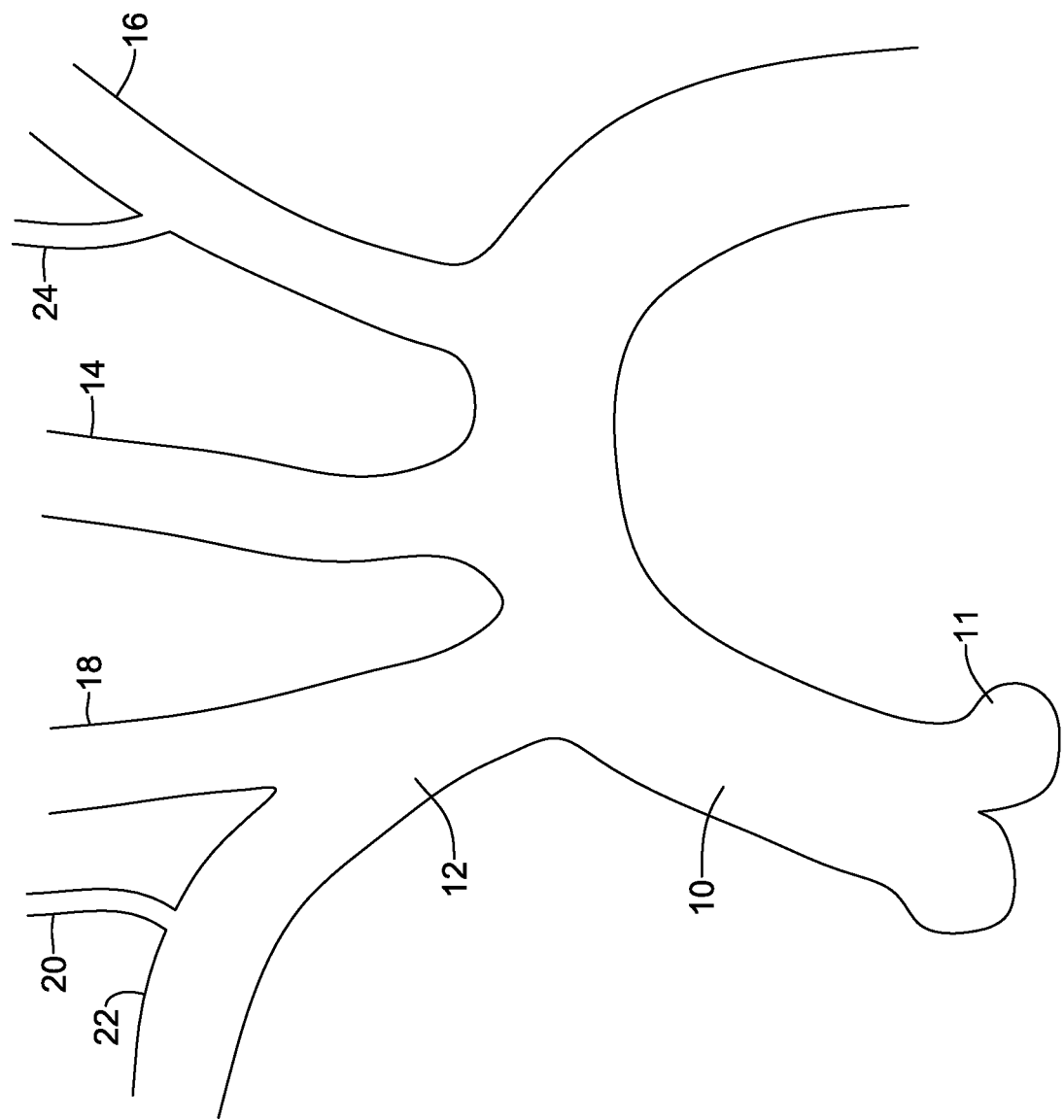
FIG. 1 is a schematic view of an aortic arch.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimension ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

The disclosure generally relates to devices and methods for filtering fluids and/or deflecting debris contained within fluids, including body fluids such as blood. The filtering or deflecting device can be positioned in an artery upstream from the brain before and/or during an endovascular procedure (e.g., transcatheter aortic valve implantation (TAVI) or replacement (TAVR), transcatheter mitral valve implantation (TAMI) or replacement (TAMR), surgical aortic valve replacement (SAVR), thoracic endovascular aortic repair (TEVAR), other surgical valve repair, implantation, or replacement, cardiac ablation (e.g., ablation of the pulmonary vein to treat atrial fibrillation) using a variety of energy modalities (e.g., radio frequency (RF), energy, cryo, microwave, ultrasound), cardiac bypass surgery (e.g., open-heart, percutaneous), transthoracic graft placement around the aortic arch, valvuloplasty, etc.) to inhibit or prevent embolic material such as debris, emboli, thrombi, etc. resulting from entering the cerebral vasculature.

Devices and methods have been developed to filter blood flowing to the innominate artery and the left common carotid artery, which provide about 90% of the blood entering the cerebral vasculature. Examples are provided in U.S. Pat. Nos. 8,876,796 and 9,492,264, which are herein incorporated by reference in its entirety. Certain such devices and methods leave the left subclavian artery, and thus the left vertebral artery, which provides about 10% of the blood entering the cerebral vasculature, exposed to potential embolic material. Other embodiments described in U.S. Pat. No. 8,876,796 filter blood flowing to the left common carotid artery and the left subclavian artery. Certain such devices and methods leave the innominate artery, and thus both the right common carotid artery and the right vertebral artery, which provide about 50% of the blood entering the cerebral vasculature, exposed to potential embolic material. Assuming perfect use and operation, either of these options may leave potential stroke rates as high as one to ten percent due to exposed arteries that provide blood flow to the cerebral vasculature.

Several multi-vessel embodiments of cerebral protection devices that can provide full cerebral protection (e.g., protecting all four blood vessels supplying blood to the brain) with minimal arch interference are described below. The devices may be used to trap and/or deflect particles in other blood vessels within a subject, and they can also be used outside of the vasculature. The devices described herein are generally adapted to be delivered percutaneously to a target location within a subject but can be delivered in any suitable way and need not be limited to minimally-invasive procedures. The devices and/or systems described herein may be used separately to protect specific vessels or in combination with other systems or multiples of a same or different device to protect multiple vessels.

FIG. 1 is a schematic view of an aortic arch 10. The aortic arch 10 is downstream of the aortic valve 11. The aortic arch 10 typically includes three great branch arteries: the brachiocephalic artery or innominate artery 12, the left common carotid artery 14, and the left subclavian artery 16. The innominate artery 12 branches to the right carotid artery 18, then the right vertebral artery 20, and thereafter is the right subclavian artery 22. The right subclavian artery 22 supplies blood to and may be directly accessed from (termed right radial access) the right arm. The left subclavian artery 16 branches to the left vertebral artery 24, usually in the shoulder area. The left subclavian artery 16 supplies blood to and may be directly accessed from (termed left radial access) the left arm.

Four of the arteries illustrated in FIG. 1 supply blood to the cerebral vasculature: (1) the left carotid artery 14 (about 40% of cerebral blood supply); (2) the right carotid artery 18 (about 40% of cerebral blood supply); (3) the right vertebral artery 20 (about 10% of cerebral blood supply); and (4) the left vertebral artery 24 (about 10% of cerebral blood supply). The devices and methods described herein are also compatible with the prevalent (27%) bovine variant.

Figure 2:
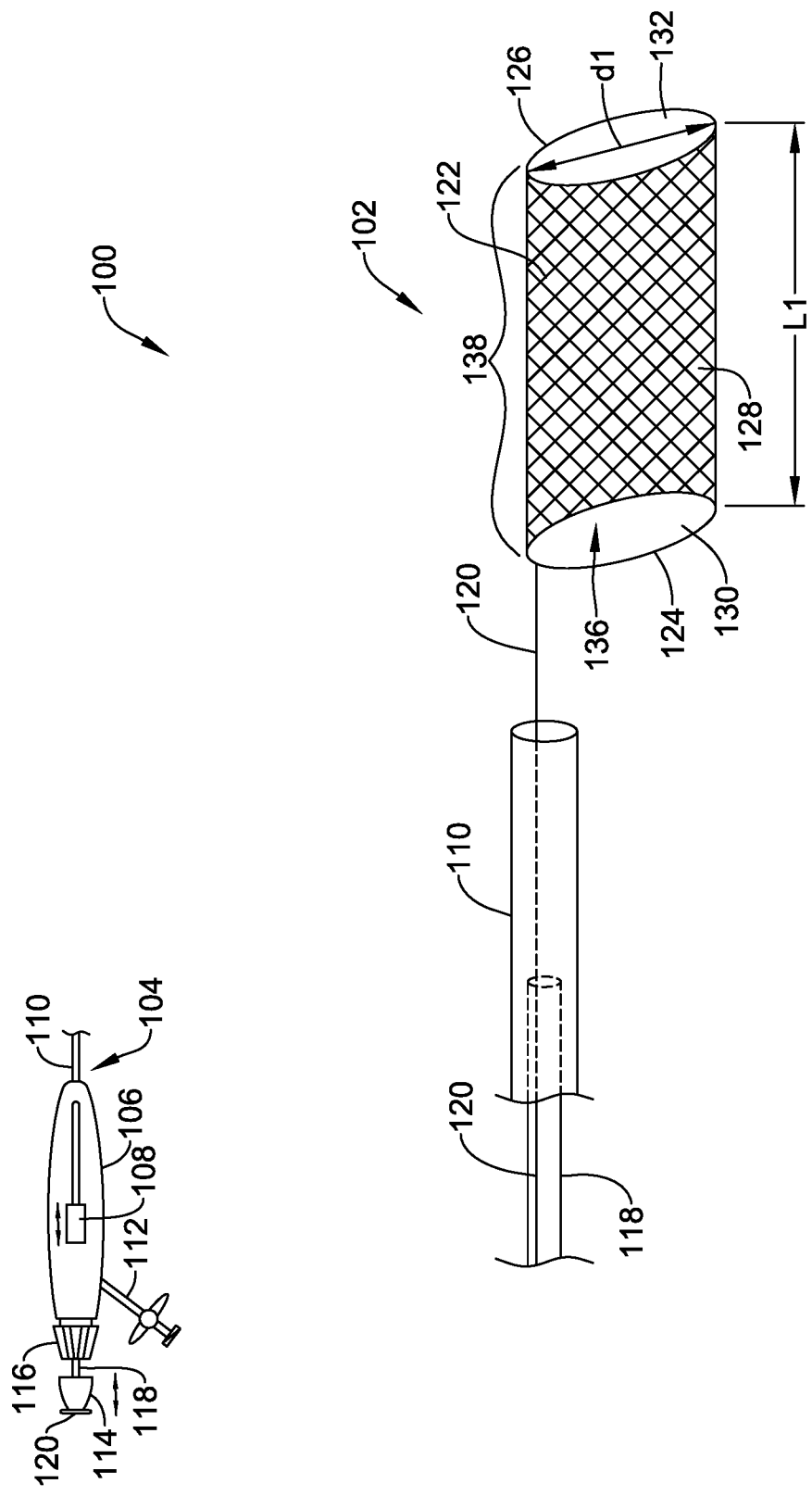
FIG. 2 illustrates a first embodiment of a protection device.

FIG. 2 illustrates a schematic side view of an illustrative filtering or protection device 100 which may be configured to filter a body fluid, such as, but not limited to blood. The protection device 100 may be used alone but is also compatible and/or synergistic with other filter systems, as will be described in more detail herein. It is further contemplated that the various filtering devices described herein can be differently combined to form various protection systems.

The protection device 100 may include a distal end region 102 and a proximal end region 104. The proximal end region 104 may be configured to be held and manipulated by a user, such as a surgeon. The distal end region 102 may be configured to be positioned at a target location such as, but not limited to, the left subclavian artery 16 adjacent to the ostium of the left vertebral artery 24. When the distal end region 102 is so deployed, blood is filtered prior to entering the left vertebral artery 24.

The proximal end region 104 may include a handle 106, a control 108 such as a slider, an outer sheath 110, a port 112, an inner member translation control 114 such as a knob, and hemostasis valve control 116 such as a knob. In some embodiments, the handle 106 may include fewer or more control elements than those illustrated in FIG. 2. The proximal end region 104 may also include an inner member 118 radially inward of the outer sheath 110, although this is not required. In some embodiments the protection device may be free from or not include the inner member 118. While not explicitly shown, the proximal end region 104 may also include a filter wire 120 radially inward of the outer sheath 110 (and sometimes radially outward of the inner member 118). Some illustrative filter wires are described in commonly assigned U.S. Pat. No. 9,566,144, the entirety of which is hereby incorporated by reference.

The slider 108 can be used to translate the outer sheath 110 and/or a filter assembly 122. For example, the slider 108 may proximally retract the outer sheath 110, the slider 108 may distally advance the filter assembly 122 out of the outer sheath 110, or the slider 108 may proximally retract the outer sheath 110 and distally advance the filter assembly 122 (e.g., simultaneously or serially), which can allow the filter assembly 122 to radially expand. The slider 108 may also be configured to have an opposite translation effect, which can allow the filter assembly 122 to be radially collapsed (e.g., due to compression by the outer sheath 110) as the filter assembly 122 is drawn into the outer sheath 110. Other deployment systems are also possible, for example comprising gears or other features such as helical tracks (e.g., configured to compensate for any differential lengthening due to foreshortening of the filter assembly 122, configured to convert rotational motion into longitudinal motion), a mechanical element, a pneumatic element, a hydraulic element, etc. for opening and/or closing the filter assembly 122. The slider 108 may be independent of the inner member 118 such that the inner member 118 is longitudinally movable independent of the filter assembly 122 and the outer sheath 110 (and/or the filter wire 120, or other components). The inner member translation control 114 can be used to longitudinally translate the inner member 118, for example before, after, and/or during deployment of the filter assembly 122. The inner member translation control 114 may comprise a slider in the handle 106 (e.g., separate from the slider 108).

The port 112 may be in fluid communication with the inner member 118 (e.g., via a Y-shaped connector in the handle 106). The port 112 can be used to flush the device (e.g., with saline) before, during, and/or after use, for example to remove air. The port 112 can additionally, or alternatively, be used to monitor blood pressure at the target location, for example by connecting an arterial pressure monitoring device in fluid communication with a lumen of the outer sheath 110. The port 112 can be also or alternatively be used to inject contrast agent, dye, thrombolytic agents such as tissue plasminogen activator (t-PA), etc.

The rotatable hemostasis valve control 116 can be used to reduce or minimize fluid loss through the protection device 100 during use. For example, a portion of the protection device 100 may be positioned in the left subclavian artery 16 and the direction of blood flow with respect to the device 100 will be distal to proximal, so blood may be otherwise inclined to follow the pressure drop out of the device 100. The hemostasis valve control 116 is illustrated as being rotatable, but other arrangements are also possible (e.g., longitudinally displaceable). The hemostasis valve control 116 may be configured to fix relative positions of the outer sheath 110 and the filter assembly 122, for example as described with respect to the hemostasis valve in U.S. Pat. No. 8,876,796. The hemostasis valve 116 may comprise, for example, an elastomeric seal and HV nut.

The distal end region 102 may include an outer sheath 110 and an inner tubular member 118. In some embodiments, the inner tubular member 118 may be coupled to the to the filter assembly 122 while in other embodiments, the inner tubular member 118 move independent of the filter assembly 122. In some embodiments, the inner tubular member 118 may not be present. The inner tubular member 118 may define a lumen (not explicitly shown) extending from a proximal end (not explicitly shown) to the distal end (not explicitly shown) thereof. The lumen may be configured to receive other medical devices, including, but not limited to a pigtail or angiography catheter 134 (see, for example, FIG. 3), a procedural catheter (such as, but not limited to a TAVR or TAVI procedural catheter or device), etc. The angiographic catheter 134 may be radially inward of the inner tubular member 118 and the inner tubular member 118 may be radially inward of the outer sheath 110. The filter assembly 122 may be radially between the outer sheath 110 and the angiographic catheter 134 (e.g., radially inward of the outer sheath 110 and the angiographic catheter 134 radially inward of the filter assembly 122) in a delivery state, shape or position. The protection device 100 may include a filter wire 120 or a guidewire radially inward of the inner tubular member 118 and/or the angiographic catheter 134. In some embodiments, the outer sheath 110 and/or the inner tubular member 118 may have a diameter large enough for a procedural catheter to pass therethrough, although this is not required. The outer sheath 110 may comprise an atraumatic distal tip. The protection device 100 and other protection devices described herein may be flexible and/or atraumatic. The outer sheath 110 may comprise a curvature, for example based on an intended placement location.

The filter assembly 122 may include a proximal end ring 124, a distal end ring 126, and a filter element 128 extending therebetween. In some embodiments, the filter assembly 122 may not require the proximal end ring 124 and/or the distal end ring 126. For example, the filter element 128 may be a self-supporting filter having stent-like braided or woven structure. In some embodiments, the proximal and/or distal end rings 124, 126 may act as a frame to generally provide expansion support to the filter element 128 in the expanded state. In the expanded state, the filter element 128 is configured to filter fluid (e.g., blood) flowing through the filter element 128 and to inhibit or prevent particles (e.g., embolic material) from flowing through the filter element 128 by capturing or deflecting the particles in the filter element 128. The proximal and/or distal end rings 124, 126 may be configured to engage or appose the inner walls of a lumen (e.g., blood vessel) in which the filter assembly 122 is expanded. The proximal and/or distal end rings 124, 126 may comprise or be constructed of, for example, nickel titanium (e.g., nitinol), nickel titanium niobium, chromium cobalt (e.g., MP35N, 35NLT), copper aluminum nickel, iron manganese silicon, silver cadmium, gold cadmium, copper tin, copper zinc, copper zinc silicon, copper zinc aluminum, copper zinc tin, iron platinum, manganese copper, platinum alloys, cobalt nickel aluminum, cobalt nickel gallium, nickel iron gallium, titanium palladium, nickel manganese gallium, stainless steel, combinations thereof, and the like. The proximal and/or distal end rings 124, 126 may comprise a wire (e.g., having a round (e.g., circular, elliptical) or polygonal (e.g., square, rectangular) cross-section). For example, in some embodiments, the proximal and/or distal end rings 124, 126 comprise a straight piece of nitinol wire shape set into a circular or oblong hoop or hoop. While not explicitly shown, one or two straight legs may longitudinally along or at an angle to a longitudinal axis of the filter assembly 122 between the proximal and distal end rings 124, 126. At least one of the proximal end ring 124, the distal end ring 126, and/or the filter element 128 may be coupled to a filter wire 120 or tether.

The filter wire 120 may be configured to facilitate retrieval of the filter assembly 122 into the outer sheath 110. The proximal and/or distal end rings 124, 126 may form a shape of an opening 130, 132 of the filter assembly 122. The opening 130, 132 may be circular, elliptical, or any shape that can appropriately appose sidewalls of a vessel such as the left subclavian artery or the left vertebral artery. In some embodiments, the openings 130, 132 may be free from the filter element 128 with a lumen 136 extending therebetween to allow for another device (e.g., an angiographic catheter 134) to pass through the lumen 136. In other embodiments, the proximal end ring may include the filter element 128 (e.g., the proximal opening 130 is covered) while the distal end ring 126 remains open or uncovered. The orientation of the uncovered opening may vary depending on where the access incision is located.

The proximal and/or distal end rings 124, 126 may include a radiopaque marker such as a small coil wrapped around or coupled to the hoop to aid in visualization under fluoroscopy. In some embodiments, the frame may comprise a shape other than a hoop, for example, a spiral. In some embodiments, the filter assembly 122 may not include or be substantially free of a frame. In some embodiments, the proximal and/or distal end rings 124, 126 and the filter element 128 have a generally tubular configuration.

The filter element 128 may have a generally tubular main body portion 138. The generally tubular main body 138 may be configured to filter blood or fluid flow that is flowing thorough the sidewall (e.g., in radial outward direction) as opposed to along a longitudinal axis of the filter assembly 122.

The filter element 128 may include pores configured to allow blood to flow through the filter element 128, but that are small enough to inhibit or prevent particles, such as embolic material, from passing through the filter element 128. The filter element 128 may comprise a filter membrane such as a polymer (e.g., polyurethane, polytetrafluoroethylene (PTFE)) film mounted to the proximal and/or distal rings 124,126 (e.g., nitinol). The filter element 128 may have a thickness between about 0.0001 inches and about 0.03 inches (e.g., no more than about 0.0001 inches, about 0.001 inches, about 0.005 inches, about 0.01 inches, about 0.015 inches, about 0.02 inches, about 0.025 inches, about 0.03 inches, ranges between such values, etc.).

The film may comprise a plurality of pores or holes or apertures extending through the film. The film may be formed by weaving or braiding filaments or membranes and the pores may be spaces between the filaments or membranes. The filaments or membranes may comprise the same material or may include other materials (e.g., polymers, non-polymer materials such as metal, alloys such as nitinol, stainless steel, etc.). The pores of the filter element 128 are configured to allow fluid (e.g., blood) to pass through the filter element 128 and to resist the passage of embolic material that is carried by the fluid. The pores can be circular, elliptical, square, triangular, or other geometric shapes. Certain shapes such as an equilateral triangular, squares, and slots may provide geometric advantage, for example restricting a part larger than an inscribed circle but providing an area for fluid flow nearly twice as large, making the shape more efficient in filtration versus fluid volume. The pores may be laser drilled into or through the filter element 128, although other methods are also possible (e.g., piercing with microneedles, loose braiding or weaving). The pores may have a lateral dimension (e.g., diameter) between about 10 micron (μm) and about 1 mm (e.g., no more than about 10 μm, about 50 μm, about 100 μm, about 150 μm, about 200 μm, about 250 μm, about 300 μm, about 400 μm, about 500 μm, about 750 μm, about 1 mm, ranges between such values, etc.). Other pore sizes are also possible, for example depending on the desired minimum size of material to be captured.

The material of the filter element 128 may comprise a smooth and/or textured surface that is folded or contracted into the delivery state by tension or compression into a lumen. A reinforcement fabric may be added to or embedded in the filter element 128 to accommodate stresses placed on the filter element 128 during compression. A reinforcement fabric may reduce the stretching that may occur during deployment and/or retraction of the filter assembly 122. The embedded fabric may promote a folding of the filter to facilitate capture of embolic debris and enable recapture of an elastomeric membrane. The reinforcement material could comprise, for example, a polymer and/or metal weave to add localized strength. The reinforcement material could be imbedded into the filter element 128 to reduce thickness. For example, imbedded reinforcement material could comprise a polyester weave mounted to a portion of the filter element 128 near the longitudinal elements of the proximal and/or distal end rings 124, 126 where tensile forces act upon the proximal and/or distal end rings 124, 126 and filter element 128 during deployment and retraction of the filter assembly 122 from the outer sheath 110 and/or the distal sheath 58.

In some embodiments, the filter element 128 may be formed from a braided or woven structure. For example, one or more filaments may be woven or braided together to form the filter element 128. The filaments may be formed from polyether ether ketone (PEEK), nitinol, stainless steel, etc. The braid and/or weave may be configured to allow fluid or blood to pass while trapping or blocking debris. It is contemplated that the braid or weave may have openings that have a lateral dimension (e.g., diameter) between about 10 micron (μm) and about 1 mm (e.g., no more than about 10 μm, about 50 μm, about 100 μm, about 150 μm, about 200 μm, about 250 μm, about 300 μm, about 400 μm, about 500 μm, about 750 μm, about 1 mm, ranges between such values, etc.). Other pore sizes are also possible, for example depending on the desired minimum size of material to be captured. It is contemplated that a braided or woven filter element 128 may not require the proximal and/or distal end rings 124, 126 to support the filter element 128.

In some cases, the filter assembly 122 may include a self-expanding filter assembly (e.g., comprising a superelastic material with stress-induced martensite due to confinement in the outer sheath 110). The filter assembly 122 may comprise a shape-memory material configured to self-expand upon a temperature change (e.g., heating to body temperature). The filter assembly 122 may comprise a shape-memory or superelastic frame (e.g., comprising a distal end hoop comprising nitinol) and a microporous material (e.g., comprising a polymer including laser-drilled holes) coupled to the frame, for example similar to the filter assemblies described in U.S. Pat. No. 8,876,796. Alternatively, or additionally, the filter assembly 122 may comprise a shape-memory or superelastic filter element 128.

The filter assembly 122 in an expanded, unconstrained state has a maximum diameter or effective diameter (e.g., if the mouth is in the shape of an ellipse) d1. The diameter d1 can be between about 1 millimeter (mm) and about 40 mm. In some embodiments (e.g., when the filter assembly 122 is configured to be positioned in the left subclavian artery 16), the diameter d1 may be between about 7 mm and about 12 mm. In other embodiments (e.g., when the filter assembly 122 is configured to be positioned in the aortic arch 10), the diameter d1 is between about 20 mm and about 35 mm. In yet other embodiments (e.g., when the filter assembly 122 is configured to be positioned in the left vertebral artery 24), the diameter d1 may be between about 2 mm and about 4.5 mm. Other diameters d1 or other types of lateral dimensions are also possible. Different diameters d1 can allow treatment of a selection of subjects having different vessel sizes.

The filter assembly 122 has a maximum length L1. The length L1 can be between about 7 mm and about 50 mm. It is contemplated that when both the proximal opening 130 and the distal opening 132 are uncovered or free from the filter element 128, the length L1 may be selected such that the filter element 128 extends across the ostium of the left vertebral artery 24, as will be described in more detail herein. Other lengths L1 are also possible, for example based on the diameter or effective diameter d1. For example, the length L1 of the filter assembly 122 may increase as the diameter d1 increases, and the length L1 of the filter assembly 122 may decrease as the diameter d1 decreases. Different lengths L1 can allow treatment of a selection of subjects having different vessel sizes.

The distal end region 102 may include fluoroscopic markers to aid a user in positioning the device 100, deploying the filter assembly 122, utilizing the angiographic catheter 134, etc. A fluoroscopic marker (not explicitly shown) may be positioned proximate to a distal end of the outer sheath 110. Another fluoroscopic marker (not explicitly shown) may be positioned proximate to a proximal end of the filter assembly 122. In some cases, another fluoroscopic marker (not explicitly shown) may be proximate to a distal end of the filter assembly 122. Another fluoroscopic marker (not explicitly shown) may be proximate to a distal end of the inner member 118. The fluoroscopic markers may comprise a radiopaque material (e.g., iridium, platinum, tantalum, gold, palladium, tungsten, tin, silver, titanium, nickel, zirconium, rhenium, bismuth, molybdenum, combinations thereof, and the like). More or fewer fluoroscopic markers are also possible.

In some embodiments, the protection device 100 may include a guidewire (not explicitly shown) extending therethrough, although the guidewire may be characterized as being separate from the protection device 100, for example independently sold, packaged, and/or directed. The guidewire may extend through a lumen of the outer sheath 110, the inner tubular member 118 and/or the angiographic catheter 134. The lumen of the outer sheath 110, the inner tubular member 118, and/or the angiographic catheter 134 may be configured to receive a guidewire having a diameter between about 0.014 inches (0.356 mm) and about 0.025 inches (0.635 mm). If so provided, the guidewire may extend through a lumen of the filter assembly 122. For example, any portion of the protection device 100 may be tracked over the guidewire to position the protection device 100 at a desired location.

The filter assembly 122 may be positioned, for example, in the left subclavian artery 16, to protect the cerebral vasculature (e.g., the left vertebral artery 24) from embolic debris during an endovascular procedure such as TAVI. While the filter assembly 122 is described as being positioned in the left subclavian artery 16, the system 100 is not so limited. The filter assembly 122 may be positioned within other arteries or lumens, as desired. It is contemplated that the filter assembly 122 may be positioned within the left subclavian artery 16 such that at least a portion of the tubular main body portion 138 of the filter element 128 is positioned over an entirety of the ostium of the left vertebral artery 24 such that blood flow is filtered prior to entering the left vertebral artery 24, as will be described in more detail herein.

Figure 3:
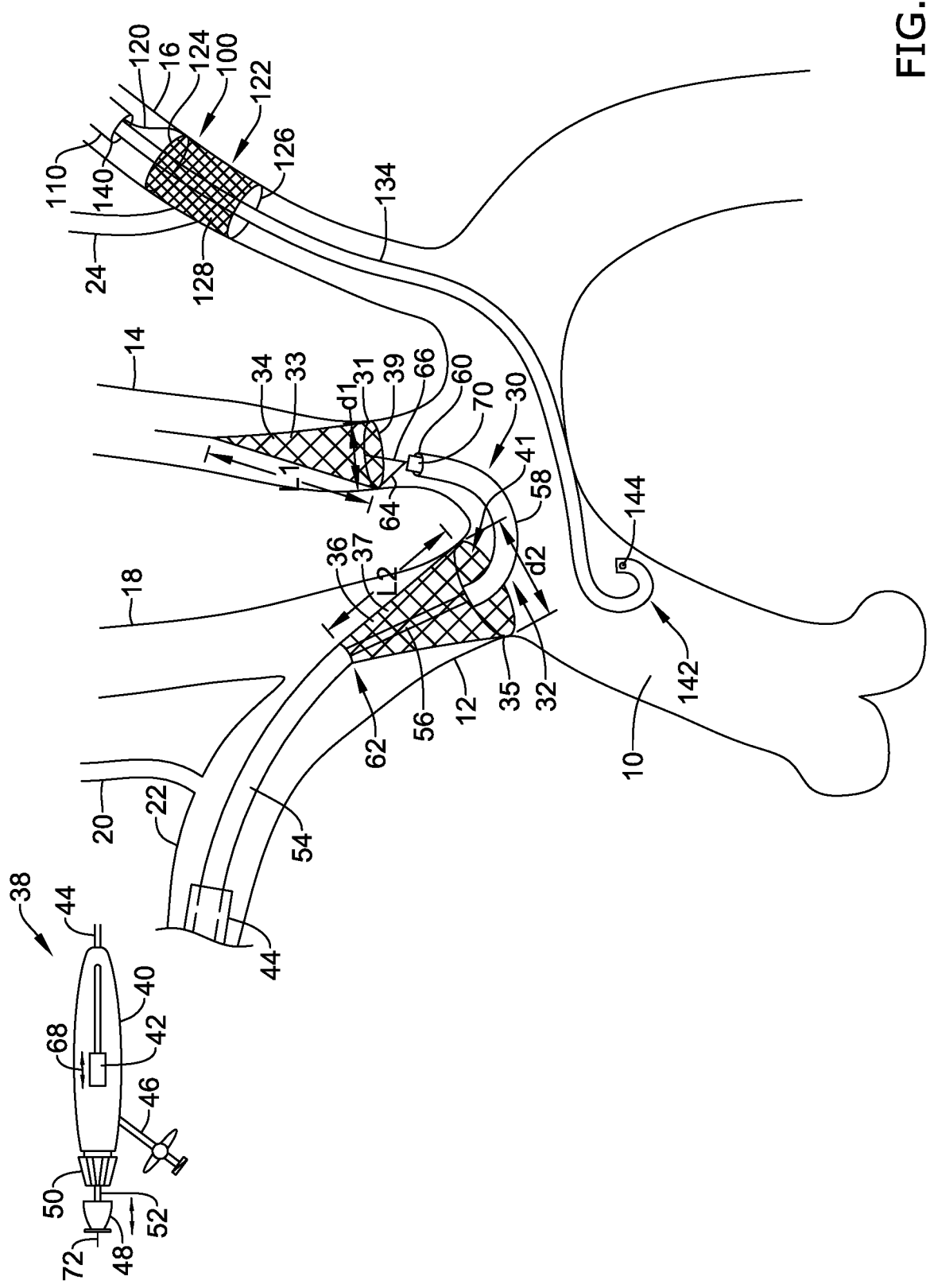
FIG. 3 illustrates another alternative embodiment of a protection device.

The protection device 100 may be used in combination with other protection devices, as shown in FIG. 3. FIG. 3 is a schematic view of an aortic arch including the protection device 100 positioned in the left subclavian artery 16 and a second protection device 30 positioned in the left common carotid artery 14 and the innominate artery 12.

In some methods of use, the first filter system 100 is advanced into the subject through an incision made in the subject's left radial artery, or alternatively the left brachial artery. The system 100 is advanced into the left subclavian artery 16. In some cases, the outer sheath 110 may be advanced over a guidewire, although this is not required. In some implementations, the guidewire and the outer sheath 110 and/or inner tubular member 118 (and/or the filter assembly 122) may be tracked together, with the guidewire leading the outer sheath 110 and/or inner tubular member 118 (e.g., advance the guidewire a distance, then advance the outer sheath 110 and/or the inner tubular member 118 over the guidewire approximately the same distance). In some cases, where the guidewire is floppy or lacks rigidity, it may be introduced inside the outer sheath 110 and then advanced ahead of the inner tubular member 118 in the vasculature.

The outer sheath 110 may be curved and/or steerable to facilitate navigation from the left subclavian artery 16. The inner tubular member 118 may be advanced simultaneously with or serially to the outer sheath 110. Additionally, the angiographic catheter 134 may be advanced simultaneously with or serially to the inner tubular member 118 and/or the outer sheath 110. Once the outer sheath 110 is positioned in or adjacent to the ostium of the left vertebral artery 24, the angiographic catheter 134 may be advanced distally from the outer sheath 110. A distal end region 142 of angiographic catheter 134 may have a generally arcuate shape (although this is not required) and may include one or more apertures 144 therein. The one or more apertures 144 may be in fluid communication with a lumen and may be configured to deliver a radiopaque fluid or contrast fluid.

Tracking of the protection device 100 may be performed under fluoroscopy, for example using radiopaque markers (e.g., at a distal end of the outer sheath 110 and/or the inner tubular member 118) and/or radiopaque fluid or contrast media. Radiopaque fluid may be provided through the inner tubular member 118, the angiographic catheter 134, and/or the outer sheath 110. The protection device 100 may be positioned so that the distal end ring 126 of the filter assembly 122 is upstream of the left vertebral artery 24 or proximate to the ostium of the left subclavian artery 16 so that the filter assembly 122 can inhibit or prevent embolic material from entering the cerebral vasculature through the left vertebral artery 24. However, it is contemplated that positioning may be based on available anatomy.

During navigation through the vasculature, the filter assembly 122 may be disposed within a lumen of the outer sheath 110 and held in a collapsed position therein until the filter assembly 122 is advanced distally from the outer sheath 110 and/or the outer sheath 110 is proximally retracted relative to the filter assembly 122. After the angiographic catheter 134 has been deployed, the outer sheath 110 may then be proximally retracted (and/or the inner tubular member 118 distally advanced if coupled to the filter assembly 122) to deploy the filter assembly 122. In some cases, the filter assembly 122 may be deployed before advancing the angiographic catheter 134, or substantially simultaneously therewith. The filter assembly 122 may be positioned to direct any dislodged debris downstream away from the left vertebral artery 24.

Radiopaque markers, for example on the filter assembly 122 can help determine when the filter assembly 122 achieves a deployed state. Differential longitudinal movement of the filter assembly 122 and the outer sheath 110 can cease upon full or appropriate deployment of the filter assembly 122. Apposition of the filter assembly 122 with sidewalls of the left subclavian artery 16 can be verified, for example using radiopaque fluid or contrast media. Radiopaque fluid may be provided through the angiographic catheter 134, the inner tubular member 118, and/or the outer sheath 110. If the radiopaque fluid is able to flow between the frame of the filter assembly 122 and the sidewalls of the aortic arch, then the filter assembly 122 may be improperly positioned (e.g., indicative of inadequate deployment, inadequate sizing, calcium, etc.). The filter assembly 122 may be retracted back into the outer sheath 110 and redeployed, or a different protection device may be used. After positioning of the protection device 100, the angiographic catheter 134 may be withdrawn and the procedural catheter advanced through the lumen of the inner tubular member 118 and the filter assembly 122, if so desired.

After the first filter device 100 has been positioned (or substantially simultaneously therewith or prior to implantation of the first system 100), a second protection device or filter system 30 may be deployed. In some embodiments, the second filter system 30 may be positioned within the innominate artery 12 and/or the left common carotid artery 14, although this is not required.

The second protection device 30 may include a distal end region 32 and a proximal end region 38. The proximal end region 38 may be configured to be held and manipulated by a user such as a surgeon. The distal end region 32 may be configured to be positioned at a target location such as, but not limited to, the innominate artery 12 and/or the left common carotid artery 14. When the distal end region 32 is so deployed, blood is filtered prior to entering the left common carotid artery 14, the right common carotid artery 18, and the right vertebral artery 20.

The proximal end region 38 may include a handle 40, a control 42 such as a slider, an outer sheath 44, a port 46, an inner member translation control 48 such as a knob, and hemostasis valve control 50 such as a knob. In some embodiments, the handle 40 may include fewer or more control elements than those illustrated in FIG. 3. The proximal end region 38 may also include an inner member 52 radially inward of the outer sheath 44. While not explicitly shown, the proximal end region 38 may also include a filter wire 66 radially inward of the outer sheath 44 (and sometimes radially outward of the inner member 52).

The slider 42 can be used to translate the outer sheath 44 and/or a filter assembly 36 (e.g., coupled to a proximal shaft 54). For example, the slider 42 may proximally retract the outer sheath 44, the slider 42 may distally advance the filter assembly 36 out of the outer sheath 44, or the slider 42 may proximally retract the outer sheath 44 and distally advance the proximal filter assembly 36 (e.g., simultaneously or serially), which can allow the proximal filter assembly 36 to radially expand. The slider 42 may also be configured to have an opposite translation effect, which can allow the filter assembly 36 to be radially collapsed (e.g., due to compression by the outer sheath 44) as the filter assembly 36 is drawn into the outer sheath 44. Other deployment systems are also possible, for example comprising gears or other features such as helical tracks (e.g., configured to compensate for any differential lengthening due to foreshortening of the filter assembly 36, configured to convert rotational motion into longitudinal motion), a mechanical element, a pneumatic element, a hydraulic element, etc. for opening and/or closing the filter assembly 36. While not explicitly shown, the handle 40 may include a similar mechanism for manipulating the distal filter assembly 34 via the filter wire 66, the inner member 52 and/or the guiding member 60.

The port 46 is in fluid communication with the inner member 52 (e.g., via a Y-shaped connector in the handle 40). The port 46 can be used to flush the device (e.g., with saline) before, during, and/or after use, for example to remove air. The port 46 can additionally, or alternatively, be used to monitor blood pressure at the target location, for example by connecting an arterial pressure monitoring device in fluid communication with a lumen of the outer sheath 44. The port 46 can be also or alternatively be used to inject contrast agent, dye, thrombolytic agents such as tissue plasminogen activator (t-PA), etc. The slider 42 may be independent of the inner member 52 such that the inner member 52 is longitudinally movable independent of the proximal filter assembly 36 and the outer sheath 44 (and/or the distal filter assembly 34, the filter wire 66, inner member 52, or the guiding member 60). The inner member translation control 48 can be used to longitudinally translate the inner member 52, for example before, after, and/or during deployment of the filter assembly 36. The inner member translation control 48 may comprise a slider in the handle 40 (e.g., separate from the slider 42).

The rotatable hemostasis valve control 50 can be used to reduce or minimize fluid loss through the protection device 30 during use. For example, a proximal portion and/or intermediate region of the protection device may be positioned in the right subclavian artery 22 and the direction of blood flow with respect to the device 30 will be distal to proximal, so blood may be otherwise inclined to follow the pressure drop out of the device 30. The hemostasis valve control 50 is illustrated as being rotatable, but other arrangements are also possible (e.g., longitudinally displaceable). The hemostasis valve control 50 may be configured to fix relative positions of the outer sheath 44 and the filter assembly 36, for example as described with respect to the hemostasis valve in U.S. Pat. No. 8,876,796. The hemostasis valve 50 may comprise, for example, an elastomeric seal and HV nut.

The distal end region 32 of the second protection device 30 may include a first or distal filter assembly 34 configured to be deployed within the left common carotid artery 14 and a second or proximal filter assembly 36 configured to deployed within the innominate artery 12. The distal end region 32 may further include a proximal (or outer) sheath 44, a proximal shaft 54 coupled to an expandable proximal filter assembly 36, a distal shaft 56 coupled to a distal articulatable sheath 58, a distal filter assembly 34, and guiding member 60.

The proximal shaft 54 is co-axial with proximal sheath 44, and a proximal region 62 of proximal filter assembly 36 is secured to proximal shaft 54. In its collapsed configuration (not explicitly shown), the proximal filter assembly 36 may be disposed within proximal sheath 44 and is disposed distally relative to proximal shaft 54. The proximal sheath 44 may be axially (e.g., distally and proximally) movable relative to proximal shaft 54 and the proximal filter assembly 36. The system 30 may also include a distal sheath 58 secured to a distal region of the distal shaft 56. The distal shaft 56 may be co-axial with the proximal shaft 54 and the proximal sheath 44. The distal sheath 58 and distal shaft 56 may be secured to one another and axially movable relative to the proximal sheath 44, the proximal shaft 54, and the proximal filter assembly 36. The system 30 may also include a distal filter assembly 34 carried by the guiding member 60. While not explicitly shown, the distal filter assembly 34 may be maintained in a collapsed configuration within the distal sheath 58. The guiding member 60 may be coaxial with distal sheath 58 and distal shaft 56 as well as proximal sheath 44 and proximal shaft 54. The guiding member 60 may be axially movable relative to distal sheath 58 and distal shaft 56 as well as proximal sheath 44 and proximal shaft 54. The proximal sheath 44, the distal sheath 58, and the guiding member 60 may each be adapted to be independently moved axially relative to one other. That is, the proximal sheath 44, the distal sheath 58, and the guiding member 60 are adapted for independent axial translation relative to each of the other two components. It is contemplated that the handle 40 may include control elements (such as, but not limited to, slides, switches, buttons, dials, etc.) configured to individually actuate the proximal sheath 44, the distal sheath 58, and the guiding member 60.

The proximal filter assembly 36 may include a support element or frame 35 and a filter element 37. Similarly, the distal filter assembly 34 includes support element 31 and a filter element 33. The frames 31, 35 may be similar in form and function to the end rings 124, 126 described herein. Similarly, the filter elements 35, 37 may be similar in form and function to the filter element 128 described herein. The frames 31, 35 may generally provide expansion support to the filter elements 33, 37 in the expanded state. In the expanded state, the filter elements 33, 37 are configured to filter fluid (e.g., blood) flowing through the filter elements 33, 37 and to inhibit or prevent particles (e.g., embolic material) from flowing through the filter elements 33, 37 by capturing the particles in the filter elements 33, 37. The frames 31, 35 are configured to engage or appose the inner walls of a lumen (e.g., blood vessel) in which the filter assembly 34, 36 is expanded.

In some embodiments, the frames 31, 35 comprises a straight piece of nitinol wire shape set into a circular or oblong hoop or hoop with one or two straight legs running longitudinally along or at an angle to a longitudinal axis of the filter assembly 34, 36. At least one of the straight legs may be coupled to a filter wire 66 or a strut 64, as shown with respect to the distal filter assembly 34. The straight legs may be on a long side of the filter assembly 34, 36 and/or on a short side of the filter assembly 34, 36. The frames 31, 35 may form a shape of an opening 39, 41 of the filter assembly 34, 36. The opening 39, 41 may be circular, elliptical, or any shape that can appropriately appose sidewalls of a vessel such as the left subclavian artery or the left vertebral artery. The filter assembly 34, 36 may have a generally proximally-facing opening 39, 41. In other embodiments, the opening 39, 41 may be distally facing. The orientation of the opening 39, 41 may vary depending on where the access incision is located. For example, as shown in FIG. 3, the proximal filter assembly 36 has a generally distally-facing opening 41, and the distal filter assembly 34 has a generally proximally-facing opening 39 relative to the device 30. The filter assemblies 34, 36 can be thought of as facing opposite directions.

In some embodiments, the frames 31, 35 and the filter elements 33, 37 form an oblique truncated cone having a non-uniform or unequal length around and along the length of the filter assembly 34, 36. In such a configuration, along the lines of a windsock, the filter assembly 34, 36 has a larger opening 39, 41 (upstream) diameter and a reduced ending (downstream) diameter.

The filter assembly 34, 36 may be coupled (e.g., crimped, welded, soldered, etc.) to a distal end of a deployment wire or filter wire 66 via a strut or wire 64, although this is not required. When both or all of the filter wire 66 and the strut 64 are provided, the filter wire 66 and the strut 64 may be coupled within the guiding member 60 proximal to the filter assembly 34 using a crimp mechanism. In other embodiments, the filter wire 66 and the strut 64 may be a single unitary structure. The filter wire 66 and/or strut 64 can comprise a rectangular ribbon, a round (e.g., circular, elliptical) filament, a portion of a hypotube, a braided structure (e.g., as described herein), combinations thereof, and the like. The filter wire 66 can be coupled to the handle 40 and/or a slider to provide differential longitudinal movement versus the outer sheath 44, as shown by the arrows 68, which can sheathe and unsheathe the distal filter assembly 34 from the distal sheath 58. Similarly, the proximal filter assembly 36 may be unsheathe through actuation of a mechanism on the handle 40 or through movement of the handle 40 itself.

The filter assembly 34, 36 in an expanded, unconstrained state has a maximum diameter or effective diameter (e.g., if the mouth is in the shape of an ellipse) d2, d3. The diameter d2, d3 can be between about 1 mm and about 15 mm (e.g., at least about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, ranges between such values, etc.). In some embodiments, the diameter d2, d3 is between about 7 mm and about 12 mm (e.g., about 7 mm, about 8 mm, about 9 mm, about 10 mm, about 11 mm, about 12 mm, ranges between such values, etc.). In some embodiments, the diameter d is between about 2 mm and about 4.5 mm (e.g., about 2 mm, about 2.5 mm, about 3 mm, about 3.5 mm, about 4 mm, about 4.5 mm, ranges between such values, etc.). Other diameters d2, d3 or other types of lateral dimensions are also possible. Different diameters d2, d3 can allow treatment of a selection of subjects having different vessel sizes.

The filter assembly 34, 36 has a maximum length L2, L3. The length L2, L3 can be between about 7 mm and about 50 mm (e.g., at least about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 30 mm, about 35 mm, about 40 mm, about 45 mm, about 50 mm, ranges between such values, etc.). Other lengths L2, L3 are also possible, for example based on the diameter or effective diameter d2, d3. For example, the length L2, L3 of the filter assembly 34, 36 may increase as the diameter d2, d3 increases, and the length L2, L3 of the filter assembly 34, 36 may decrease as the diameter d2, d3 decreases. A distance from an apex of the mouth of the filter assembly 34, 36 to an elbow in the frame may be about 35 mm. Different lengths L2, L3 can allow treatment of a selection of subjects having different vessel sizes.

As described in more detail below, the distal sheath 58 may be adapted to be steered, or bent, relative to the proximal sheath 44 and the proximal filter assembly 36. As the distal sheath 58 is steered, the relative directions in which the openings face will be adjusted. Regardless of the degree to which the distal sheath 58 is steered, the filter assemblies 34, 36 are still considered to having openings facing opposite directions. For example, the distal sheath 58 could be steered to have an approximately 180 degree bend, in which case the filter assemblies 34, 36 would have openings 39, 41 facing in substantially the same direction, as shown in FIG. 3. The directions of the filter openings 41, 39 are therefore described if the system were to assume a substantially straightened configuration (not explicitly shown). The proximal filter element 37 may taper down in the proximal direction from support element 35, while the distal filter element 33 may taper down in the distal direction from support element 31. A fluid, such as blood, flows through the opening and passes through the pores in the filter elements 33, 37, while the filter elements 33, 37 are adapted to trap foreign particles therein and prevent their passage to a location downstream of the filter assemblies.

The filter assemblies 34, 36 may be secured to separate system components. For example, the proximal filter assembly 36 is secured to the proximal shaft 54, while the distal filter assembly 34 is secured to guiding member 60. In FIG. 3, the filter assemblies 34, 36 are secured to independently actuatable components. This may allow the filter assemblies 34, 36 to be independently positioned and controlled. Additionally, the filter assembles 34, 36 may be collapsed within two different tubular members in their collapsed configurations. For example, the proximal filter assembly 36 is collapsed within proximal sheath 44, while the distal filter assembly 34 is collapsed within distal sheath 58. In the system's delivery configuration, the filter assemblies 34, 36 are axially-spaced from one another. For example, in FIG. 3, the distal filter assembly 34 is distally-spaced relative to proximal filter assembly 36. However, in an alternative embodiment, the filter assemblies 34, 36 may be positioned such that a first filter is located within a second filter.

In some embodiments, the distal sheath 58 and the proximal sheath 44 have substantially the same outer diameter. When the filter assemblies 34, 36 are collapsed within the respective sheaths 58, 44, the sheath portion of the system 30 therefore has a substantially constant outer diameter, which can ease the delivery of the system 30 through the patient's body and increase the safety of the delivery. The distal and proximal sheaths 58, 44 may have substantially the same outer diameter, both of which have larger outer diameters than the proximal shaft 54. The proximal shaft 54 may have a larger outer diameter than the distal shaft 56, wherein the distal shaft 56 is disposed within the proximal shaft 54. The guiding member 60 may have a smaller diameter than the distal shaft 56. In some embodiments, the proximal and distal sheaths 44, 58 have an outer diameter between 3 French (F) and 14 F. In certain embodiments, the outer diameter is between 4 F and 8 F. In still other embodiments, the outer diameter is between 4 F and 6 F. In some embodiments, the sheaths 44, 58 have different outer diameters. For example, the proximal sheath 44 can have a size of 6 F, while the distal sheath 58 has a size of 5 F. In an alternate embodiment the proximal sheath 44 is 5 F and the distal sheath 58 is 4 F. These are just examples and are not intended to limit the sheaths 44, 58 to a particular size. A distal sheath 58 with a smaller outer diameter than the proximal sheath 44 reduces the delivery profile of the system 30 and can ease delivery.

In some methods of use, the second filter system 30 is advanced into the subject through an incision made in the subject's right radial artery, or alternatively the right brachial artery. In a variety of medical procedures, a medical instrument is advanced through a subject's femoral artery, which is larger than the right radial artery. A delivery catheter used in femoral artery access procedures has a larger outer diameter than would be allowed in a filter system advanced through a radial artery. Additionally, in some uses the filter system is advanced from the right radial artery into the aorta via the brachiocephalic trunk. The radial artery has the smallest diameter of the vessels through which the system is advanced. The radial artery therefore limits the size of the system that can be advanced into the subject when the radial artery is the access point. The outer diameters of the systems described herein, when advanced into the subject via a radial artery, are therefore smaller than the outer diameters of the guiding catheters (or sheaths) typically used when access is gained via a femoral artery. In some embodiments, the system 30 may be advanced over a guidewire 72, although this is not required.

The system 30 may be delivered to the left carotid artery 14 and the innominate artery 12 in a delivery configuration. The system's delivery configuration generally refers to the configuration where both filter assemblies 34, 36 are in collapsed configurations within the system (e.g., within the distal and proximal sheaths 58, 44). The distal articulating sheath 58 may be independently movable with 3 degrees of freedom relative to the proximal sheath 44 and proximal filter assembly 36. In some embodiments, the proximal sheath 44 and the distal sheath 58 may be releasably coupled together. For example, the proximal sheath 44 can be coupled to the distal sheath 58 using an interference fit, a friction fit, a spline fitting, end to end butt fit or any other type of suitable coupling between the two sheaths 44, 58. When coupled together, the components move as a unit. For example, the proximal sheath 44, the proximal shaft 54, the proximal filter assembly 36, the distal shaft 56, and the distal filter assembly 34 will rotate and translate axially (in the proximal or distal direction) as a unit. When the proximal sheath 44 is retracted to allow the proximal filter assembly 36 to expand, the distal sheath 58 can be independently rotated, steered, or translated axially (either in the proximal direction or distal direction). The distal sheath 58 therefore has 3 independent degrees of freedom: axial translation, rotation, and steering. The adaptation to have 3 independent degrees of freedom is advantageous when positioning the distal sheath 58 in a target location, details of which are described below.

The system 30 is advanced into the subject's right radial artery through an incision in the right arm, or alternately through the right brachial artery. The system is advanced through the right subclavian artery 22 and into the brachiocephalic or innominate artery 12, and a portion of the system is positioned within the aortic arch 10. The proximal sheath 44 is retracted proximally to allow proximal filter support element 35 to expand to an expanded configuration against the wall of the innominate artery 12, as is shown in FIG. 3. The proximal filter element 37 is secured either directly or indirectly to support element 35 and is therefore reconfigured to the configuration shown in FIG. 3. The position of distal sheath 58 can be substantially maintained while proximal sheath 44 is retracted proximally. Once expanded, the proximal filter assembly 36 filters blood traveling through the innominate artery 12, and therefore filters blood traveling into the right common carotid artery 18 and the right vertebral artery 20. The expanded proximal filter assembly 36 is therefore in position to prevent foreign particles from traveling into the right common carotid artery 18 and the right vertebral artery 20 and into the cerebral vasculature.

The distal sheath 58 is then steered, or bent, and the distal end 70 of the distal sheath 58 is advanced into the left common carotid artery 14. The guiding member 60 is thereafter advanced distally relative to distal sheath 58, allowing the distal support element 31 to expand from a collapsed configuration to a deployed configuration against the wall of the left common carotid artery 14, as shown in FIG. 3. The distal filter element 33 is also reconfigured into the configuration shown in FIG. 3. Once expanded, the distal filter assembly 34 filters blood traveling through the left common carotid artery 14. In some embodiments, the distal filter assembly 34 may be deployed prior to the deployment of the proximal filter assembly 36. The distal filter assembly 34 is therefore in position to trap foreign particles and prevent them from traveling into the cerebral vasculature. Together, the first protection device 100 and the second protection device 30 may protect all four cerebral arteries 14, 18, 20, 24 during a procedure.

The protection device(s) 100, 30 can thereafter be removed from the subject (or at any point in the procedure). In an illustrative embodiment, to remove the second protection device 30, the distal filter assembly 34 is first retrieved back within distal sheath 58 to the collapsed configuration. To do this, the guiding member 60 is retracted proximally relative to the distal sheath 58. This relative axial movement causes the distal sheath 58 to engage a strut or wire 64 and begin to move strut 64 towards guiding member 60. The support element 31, which is coupled to the strut 64, begins to collapse upon the collapse of the strut 64. The filter element 33 therefore begins to collapse as well. Continued relative axial movement between the guiding member 60 and the distal sheath 58 continues to collapse the strut 64, the support element 31, and the filter element 33 until the distal filter assembly 34 is retrieved and re-collapsed back within distal sheath 58 (not explicitly shown). Any foreign particles trapped within the distal filter element 33 are contained therein as the distal filter assembly 34 is re-sheathed. The distal sheath 58 is then steered into a configuration where the distal sheath 58 is generally parallel with the distal shaft 56. Said differently, the distal sheath 58 is steered such that it has a generally linear orientation. The proximal sheath 44 is then advanced distally relative to proximal filter assembly 36. This causes proximal filter assembly 36 to collapse around the distal shaft 56, trapping any particles within the collapsed proximal filter element 37. The proximal sheath 44 continues to be moved distally towards the distal sheath 58 until the proximal sheath 44 is coupled with or nearly coupled with the distal sheath 58. The entire system 30 can then be removed from the subject.

The first filter system 100 can be removed either before, substantially simultaneously with, or after the second filter system 30. The outer sheath 110 is advanced distally relative to the filter assembly 122. This causes the filter assembly 122 to collapse. As the opening 130 of proximal end ring 124 may be free from the filter element 128, the filter assembly 122 may not trap any debris or may trap less debris than if the proximal end ring 124 included a filter element 128. The outer sheath 110 continues to be moved distally until the entire filter assembly 122 is within the sheath 110. The entire system 100 can then be removed from the subject.

In any of the embodiments mentioned herein, the filter or filter assemblies 34, 36, 122 may alternatively be detached from the delivery catheter, and the delivery catheter removed leaving the filter assemblies 34, 36, 122 behind. The filter or filter assemblies 34, 36, 122 can be left in place permanently, or retrieved by snaring it with a retrieval catheter following a post procedure treatment period of time. Alternatively, the filter assemblies 34, 36, 122 may remain attached to the catheter, and the catheter may be left in place post procedure for the treatment period of time. That treatment period may be at least one day, one week, three weeks, five weeks or more, depending upon the clinical circumstances. Patients with an indwelling filter or filter assemblies may be administered any of a variety of thrombolytic or anticoagulant therapies, including tissue plasminogen activator, streptokinase, coumadin, heparin and others known in the art.

Figure 4:
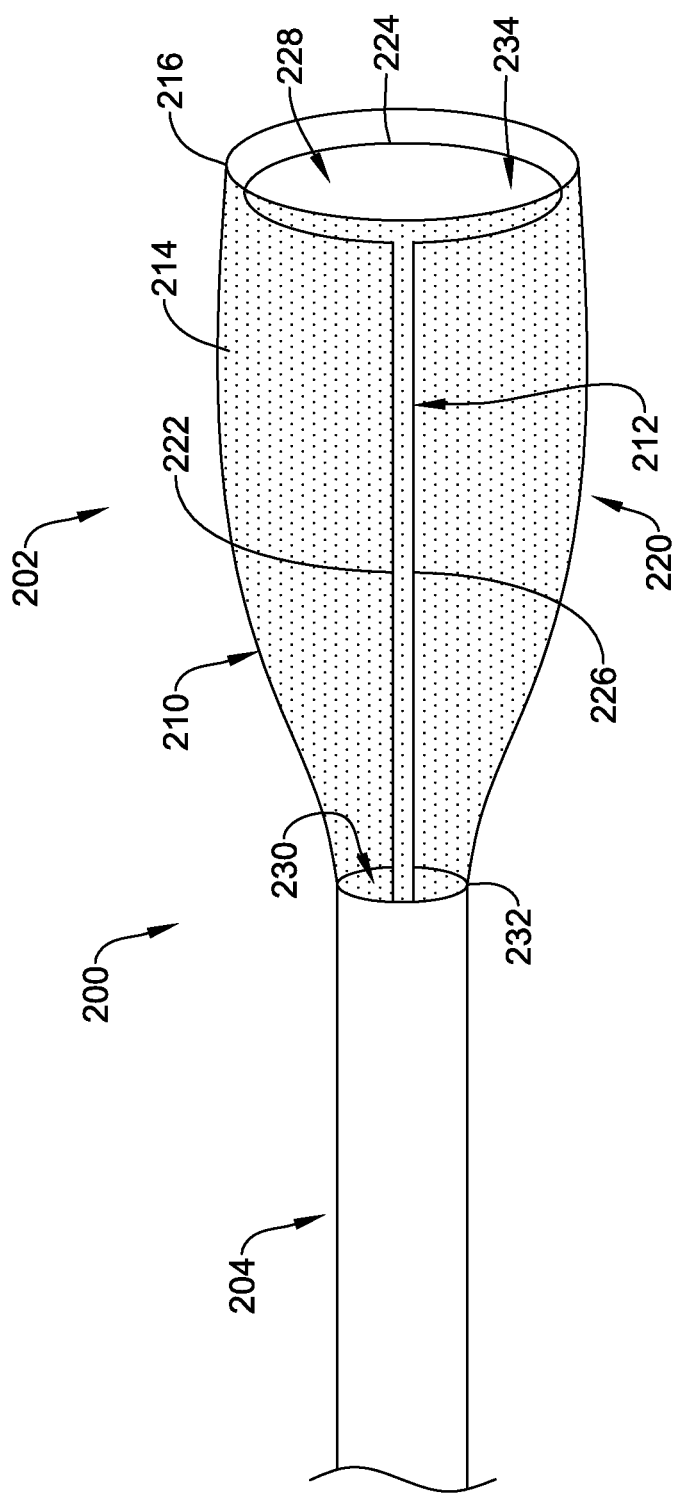
FIG. 4 illustrates another alternative embodiment of a protection device.

FIG. 4 illustrates a side view of another illustrative protection device 200. The protection device 200 may be configured to be positioned in the left subclavian artery 16. In some cases, the protection device 200 may be positioned in another vessel or lumen. In some embodiments, the protection device 200 may be used in combination with other protection devices, such as, but not limited to the protection device 30 described herein.

The protection device 200 comprises a proximal portion (not explicitly shown) and a distal portion 202. The proximal portion is configured to be held and manipulated by a user such as a surgeon. In some cases, the proximal portion may be coupled to a handle configured to facilitate delivery and deployment of the device 200. In some cases, the handle of the protection device 200 may be similar in form and function to the handles 40, 106 described herein. The distal portion 202 is configured to be positioned at a target location such as the left subclavian artery 16. When the distal portion 202 is configured to be positioned at the left subclavian artery 16, the location may be upstream of the left vertebral artery 24 such that the blood is filtered prior to entering the left vertebral artery 24.

The protection device 200 may include at least an outer sheath 204 and a filter assembly 210. The filter assembly 210 may include a filter element 214 and a tether or wire 212, or support element, woven into the filter element 214 adjacent a distal end 216 thereof. In some embodiments, the filter assembly 210 may be a stent supported filter. The wire 212 may include two free ends (not explicitly shown) configured to remain outside the body. To weave the wire 212 into the filter element 214, a first end of the wire 212 may be woven into a main body portion 220 of the filter element 214 in the distal direction. Once the first end of the wire 212 is adjacent to the distal end 216 of the filter element 214, the wire 212 may be woven about the circumference of the filter element 214. It is contemplated that the wire 212 may extend about 360° degrees, less than 360°, less than 270°, less than 180°, etc. about the circumference of the filter element 214. The first end of the wire 212 may then be woven into the main body portion 220 of the filter element 214 in the proximal direction. For example, the wire 212 may include a generally longitudinally extending first portion 222, a circumferentially extending second portion 224, and a generally longitudinally extending third portion 226. It is contemplated that alternative patterns and/or methods of interweaving the wire 212 may be used, as desired. For example, at least one of the free ends of the wire 212 may not extend to the proximal end of the device 200.

The wire 212 may be similar in form and function to the end rings 124, 126 described herein. For example, the wire 212 may be formed from similar materials, wire shapes, sizes, etc., as the end rings 124, 126. Similarly, the filter element 214 may be similar in form and function to the filter element 128 described herein. In some embodiments, the filter assembly 210 may be self-expanding. The wire 212 generally provides expansion support to the filter element 214 in its expanded configurations, while the filter element 214 is adapted to filter fluid, such as blood, and trap particles flowing therethrough. The wire 212 may also facilitate retrieval of the filter assembly 210. The wire 212 is adapted to engage the wall of the lumen in which it is expanded to ensure good apposition and sealing with the wall. The filter element 214 has pores therein that are sized to allow the blood to flow therethrough, but are small enough to prevent unwanted foreign particles from passing therethrough. The foreign particles are therefore trapped by and within the filter element 214. As shown in FIG. 4, the filter assembly 210 has a generally distally-facing opening 228. In other embodiments, the opening 228 may be proximally facing. The orientation of the opening 228 may vary depending on where the access incision is located and/or the vessel in which it is deployed.

In some embodiments, the wire 212 and the filter element 214 form an oblique truncated cone having a non-uniform or unequal length around and along the length of the filter assembly 210. In such a configuration, along the lines of a windsock, the filter assembly 210 has a larger opening 228 (upstream) diameter and a reduced ending (downstream) diameter. The filter assembly may define a central lumen 234 extending the length thereof to allow an angiographic or pigtail catheter to pass through the lumen 234. The lumen 234 may include an open proximal end and an open distal end 228. It is contemplated that the open proximal end may be in fluid communication with the central lumen 230 of the outer sheath 204 or other tubular member to direct any captured debris away from the cerebral vasculature. In some cases, the open proximal end of the filter assembly may be positioned within a distal portion of the lumen 230 of the outer sheath 204 or other tubular member.

The outer sheath 204 may define a lumen 230 extending from a proximal end to the distal end 232 thereof. The lumen 230 may be configured to slidably receive the filter assembly 210, an inner tubular member (not explicitly shown) pigtail or angiography catheter (not explicitly shown), and/or a procedural catheter (such as, but not limited to a TAVR or TAVI procedural catheter or device), etc. The pigtail catheter (if so provided) and the filter assembly 210 may be radially inward of the outer sheath 204. In some embodiments, the pigtail catheter and the filter assembly 210 may be advanced simultaneously (or substantially simultaneously) through the lumen 230 of the outer sheath 204. In other embodiments, the pigtail catheter (if so provided) and the filter assembly 210 may be advanced sequentially or one after the other. The filter assembly 210 may be radially within the outer sheath 204 in a delivery state or shape or position. The outer sheath 204 may have a diameter large enough for a procedural catheter to pass therethrough. The outer sheath 204 may comprise an atraumatic distal tip. In some cases, the outer sheath 204 may be flexible and/or atraumatic. The outer sheath 204 may comprise a curvature, for example based on an intended placement location (e.g., the left subclavian artery 16 and/or other lumen). Alternatively, or additionally, the outer sheath 204 may be steerable.

The filter assembly 210 may be coupled (e.g., crimped, welded, soldered, etc.) to the wire 212. For example, as described above, the wire 212 may be interwoven with the filter element 214. However, it is contemplated that the filter assembly 210 may be coupled to the wire 212 using other methods, including, but not limited to, crimping, welding, soldering, adhesives, hot melting, etc. The wire 212 can be coupled to a handle or a component thereof (not explicitly shown) to provide differential longitudinal movement relative to the outer sheath 204, which can sheathe and unsheathe the filter assembly 210 from the outer sheath 204.

While not explicitly shown, the filter assembly 210 may, in addition to, or alternatively to, the wire 212, be mounted on a tubular shaft. The tubular shaft may be similar in form and function to the guiding member 60 described above and may be advanced within the lumen 230 of the outer sheath 204. It is contemplated that the tubular shaft may be advanced over a guidewire to facilitate navigation to the left subclavian artery 16. For example, the left subclavian artery 16 may be cannulated with a guidewire and the filter assembly 210 inserted into the left subclavian artery 16 by advancing the tubular shaft over the guidewire.

The distal portion 202 may include fluoroscopic markers to aid a user in positioning the device 200, deploying the filter assembly 210, utilizing the pigtail catheter, etc. A fluoroscopic marker (not explicitly shown) may be positioned proximate to a distal end of the outer sheath 204. Another fluoroscopic marker (not explicitly shown) may be positioned proximate to a proximal end of the filter assembly 210. In some cases, another fluoroscopic marker (not explicitly shown) may be proximate to a distal end of the filter assembly 210. The fluoroscopic markers may comprise a radiopaque material (e.g., iridium, platinum, tantalum, gold, palladium, tungsten, tin, silver, titanium, nickel, zirconium, rhenium, bismuth, molybdenum, combinations thereof, and the like). More or fewer fluoroscopic markers are also possible.

In some methods of use, the filter system 200 is advanced into the subject through an incision made in the subject's left radial artery, or alternatively the left brachial artery. The system 200 is advanced into the left subclavian artery 16. In some cases, the outer sheath 204 may be advanced over a guidewire, although this is not required. In some implementations, the guidewire and the outer sheath 204 and/or inner tubular member, if so provided, (and/or the filter assembly 210) may be tracked together, with the guidewire leading the outer sheath 204 and/or inner tubular member (e.g., advance the guidewire a distance, then advance the outer sheath 204 and/or the inner tubular member over the guidewire approximately the same distance). In some cases, where the guidewire is floppy or lacks rigidity, it may be introduced inside the outer sheath 204 and then advanced ahead of the inner tubular member in the vasculature.

The outer sheath 204 may be curved and/or steerable to facilitate navigation from the left subclavian artery 16. The inner tubular member may be advanced simultaneously with or serially to the outer sheath 204. Additionally, the angiographic catheter may be advanced simultaneously with or serially to the inner tubular member and/or the outer sheath 204. Once the outer sheath 204 is positioned in or adjacent to the ostium of the left vertebral artery 24, the angiographic catheter may be advanced distally from the outer sheath 204.

Tracking of the protection device 200 may be performed under fluoroscopy, for example using radiopaque markers (e.g., at a distal end of the outer sheath 204 and/or the inner tubular member) and/or radiopaque fluid or contrast media. Radiopaque fluid may be provided through the inner tubular member, the angiographic catheter, and/or the outer sheath 204. The protection device 200 may be positioned so that the circumferentially extending second portion 224 of the wire 212 of the filter assembly 210 is upstream of the left vertebral artery 24 or proximate to the ostium of the left subclavian artery 16 so that the filter assembly 210 can inhibit or prevent embolic material from entering the cerebral vasculature through the left vertebral artery 24. However, it is contemplated that positioning may be based on available anatomy.

During navigation through the vasculature, the filter assembly 210 may be disposed within a lumen of the outer sheath 204 and held in a collapsed position therein until the filter assembly 210 is advanced distally from the outer sheath 204 and/or the outer sheath 204 is proximally retracted relative to the filter assembly 210. After the angiographic catheter has been deployed, the outer sheath 204 may then be proximally retracted (and/or the inner tubular member distally advanced if coupled to the filter assembly 210) to deploy the filter assembly 210. In some cases, the filter assembly 210 may be deployed before advancing the angiographic catheter, or substantially simultaneously therewith. The filter assembly 210 may be positioned to direct any dislodged debris downstream away from the left vertebral artery 24.

Radiopaque markers, for example on the filter assembly 210 can help determine when the filter assembly 210 achieves a deployed state. Differential longitudinal movement of the filter assembly 210 and the outer sheath 204 can cease upon full or appropriate deployment of the filter assembly 210. Apposition of the filter assembly 210 with sidewalls of the left subclavian artery 16 can be verified, for example using radiopaque fluid or contrast media. Radiopaque fluid may be provided through the angiographic catheter, the inner tubular member, and/or the outer sheath 204. If the radiopaque fluid is able to flow between the frame of the filter assembly 210 and the sidewalls of the aortic arch, then the filter assembly 210 may be improperly positioned (e.g., indicative of inadequate deployment, inadequate sizing, calcium, etc.). The filter assembly 210 may be retracted back into the outer sheath 204 and redeployed, or a different protection device may be used. After positioning of the protection device 200, the angiographic catheter may be withdrawn and the procedural catheter advanced through the lumen of the inner tubular member and the filter assembly 210, if so desired.

After the filter device 200 has been positioned (or substantially simultaneously therewith or prior to implantation of the device 200), a second protection device or filter system, such as, but not limited to the protection device 30 described herein may be deployed. In some embodiments, the second filter system 30 may be positioned within the innominate artery 12 and/or the left common carotid artery 14, although this is not required.

The filter device 200 can be removed either before, substantially simultaneously with, or after the second filter system 30, if so provided. The filter assembly 210 may be retrieved by applying a proximal force or pulling motion on the wire 212 (e.g., on one or both of the free ends thereof) to invert the filter assembly 210 and pull it into the lumen 230 of the outer sheath 204. Alternatively or in addition to the proximal force on the wire 212, the outer sheath 204 is advanced distally relative to the filter assembly 210. This causes the filter assembly 210 to collapse, trapping any particles within the collapsed proximal filter element 214. The wire 212 is proximally actuated and/or the outer sheath 204 moved distally until the entire filter assembly 210 is within the sheath 204. The entire system 200 can then be removed from the subject.

In any of the embodiments mentioned herein, the filter assembly 210 may alternatively be detached from the delivery catheter, and the delivery catheter removed leaving the filter assembly 210 behind. The filter assembly 210 can be left in place permanently, or retrieved by snaring it with a retrieval catheter following a post procedure treatment period of time. Alternatively, the filter assembly 210 may remain attached to the catheter, and the catheter may be left in place post procedure for the treatment period of time. That treatment period may be at least one day, one week, three weeks, five weeks or more, depending upon the clinical circumstances. Patients with an indwelling filter or filter assemblies may be administered any of a variety of thrombolytic or anticoagulant therapies, including tissue plasminogen activator, streptokinase, coumadin, heparin and others known in the art.

Figure 5:
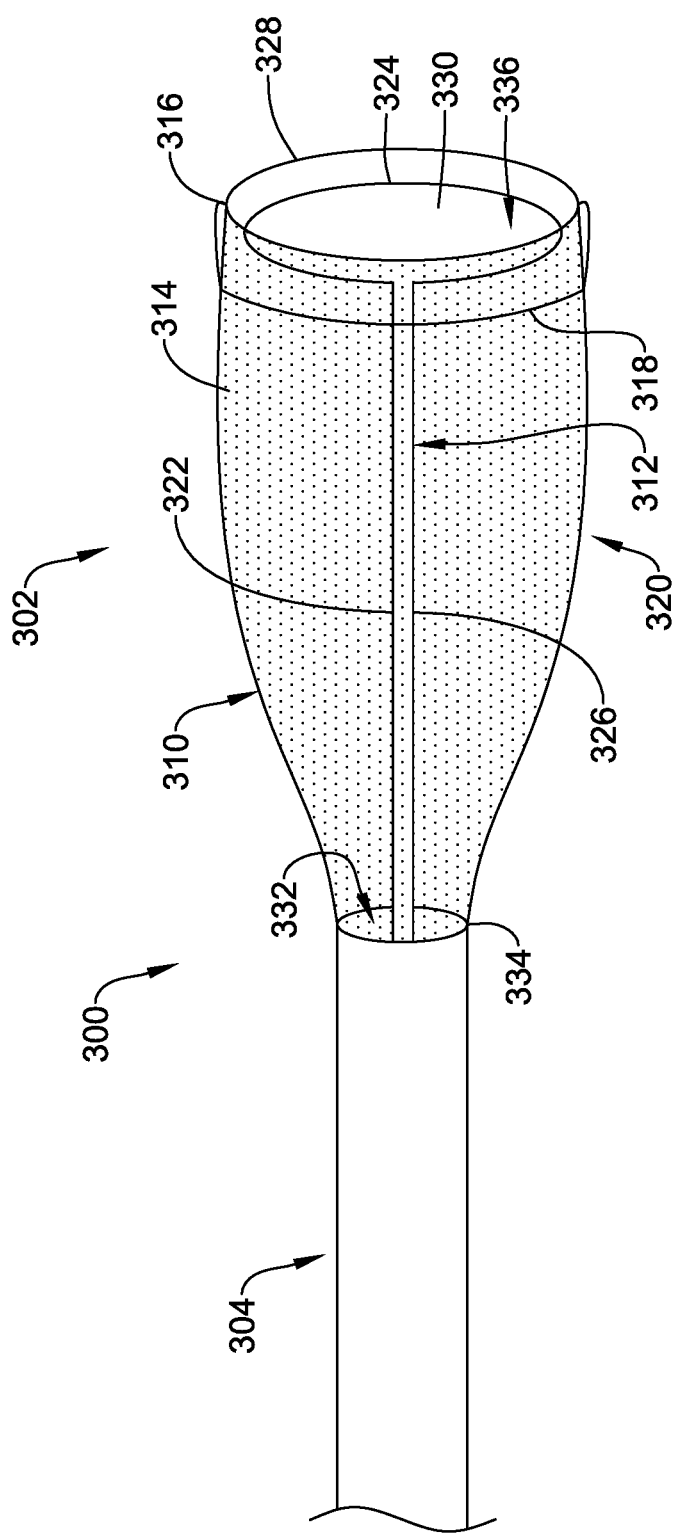
FIG. 5 illustrates another alternative embodiment of a protection device.

FIG. 5 illustrates a side view of another illustrative protection device 300. The protection device 300 may be configured to be positioned in the left subclavian artery 16 and may be similar in form and function the protection device 200 described herein. In some cases, the protection device 300 may be positioned in another vessel or lumen. In some embodiments, the protection device 300 may be used in combination with other protection devices, such as, but not limited to the protection device 30 described herein.

The protection device 300 comprises a proximal portion (not explicitly shown) and a distal portion 302. The proximal portion is configured to be held and manipulated by a user such as a surgeon. In some cases, the proximal portion may be coupled to a handle configured to facilitate delivery and deployment of the device 300. In some cases, the handle of the protection device 300 may be similar in form and function to the handles 40, 106 described herein. The distal portion 302 is configured to be positioned at a target location such as the left subclavian artery 16. When the distal portion 302 is configured to be positioned at the left subclavian artery 16, the location may be upstream of the left vertebral artery 24 such that the blood is filtered prior to entering the left vertebral artery 24.

The protection device 300 may include at least an outer sheath 304 and a filter assembly 310. The filter assembly 310 may include a filter element 314 and a tether or wire 312, or support element, woven into the filter element 314 adjacent a distal end region 316 thereof. In some embodiments, the filter assembly 310 may be a stent supported filter. The wire 312 may include two free ends (not explicitly shown) configured to remain outside the body. To weave the wire 312 into the filter element 314, a first end of the wire 312 may be woven into a main body portion 320 of the filter element 314 in the distal direction. Once the first end of the wire 312 is adjacent to the distal end 316 of the filter element 314, the wire 312 may be woven about the circumference of the filter element 314. It is contemplated that the wire 312 may extend about 360° degrees, less than 360°, less than 270°, less than 180°, etc. about the circumference of the filter element 314. The first end of the wire 312 may then be woven into the main body portion 320 of the filter element 314 in the proximal direction. For example, the wire 312 may include a generally longitudinally extending first portion 322, a circumferentially extending second portion 324, and a generally longitudinally extending third portion 326. It is contemplated that alternative patterns and/or methods of interweaving the wire 312 may be used, as desired. For example, at least one of the free ends of the wire 312 may not extend to the proximal end of the device 300. The terminating distal end or edge 318 of the filter element 314 may be folded back (e.g., in the proximal direction) over the circumferentially extending second portion 324 of the wire 312 to create an atraumatic distal end 328. Alternatively, or additionally, the distal end region 316 may be encapsulated with polymer fused into the distal end region 316. It is contemplated that any of the filter assemblies described herein may be encapsulated or include a folded edge to create an atraumatic tip.

The wire 312 may be similar in form and function to the end rings 124, 126 described herein. For example, the wire 312 may be formed from similar materials, wire shapes, sizes, etc., as the end rings 124, 126. Similarly, the filter element 314 may be similar in form and function to the filter element 128 described herein. In some embodiments, the filter assembly 310 may be self-expanding. The wire 312 generally provides expansion support to the filter element 314 in its expanded configurations, while the filter element 314 is adapted to filter fluid, such as blood, and trap particles flowing therethrough. The wire 312 may also facilitate retrieval of the filter assembly 310. The wire 312 is adapted to engage the wall of the lumen in which it is expanded to ensure good apposition and sealing with the wall. The filter element 314 has pores therein that are sized to allow the blood to flow therethrough, but are small enough to prevent unwanted foreign particles from passing therethrough. The foreign particles are therefore trapped by and within the filter element 314. As shown in FIG. 5, the filter assembly 310 has a generally distally-facing opening 330. In other embodiments, the opening 330 may be proximally facing. The orientation of the opening 330 may vary depending on where the access incision is located and/or the vessel in which it is deployed.

In some embodiments, the wire 312 and the filter element 314 form an oblique truncated cone having a non-uniform or unequal length around and along the length of the filter assembly 310. In such a configuration, along the lines of a windsock, the filter assembly 310 has a larger opening 330 (upstream) diameter and a reduced ending (downstream) diameter. The filter assembly may define a central lumen 336 extending the length thereof to allow an angiographic or pigtail catheter to pass through the lumen 336. The lumen 336 may include an open proximal end and an open distal end 330. It is contemplated that the open proximal end may be in fluid communication with the central lumen 332 of the outer sheath 304 or other tubular member to direct any captured debris away from the cerebral vasculature. In some cases, the open proximal end of the filter assembly may be positioned within a distal portion of the lumen 332 of the outer sheath 304 or other tubular member. The outer sheath 304 may define a lumen 332 extending from a proximal end to the distal end 334 thereof and may be similar in form and function to the outer sheath 204 described herein.

The filter assembly 310 may be coupled (e.g., crimped, welded, soldered, etc.) to the wire 312. For example, as described above, the wire 312 may be interwoven with the filter element 314. However, it is contemplated that the filter assembly 310 may be coupled to the wire 312 using other methods, including, but not limited to, crimping, welding, soldering, adhesives, hot melting, etc. The wire 312 can be coupled to a handle or a component thereof (not explicitly shown) to provide differential longitudinal movement relative to the outer sheath 304, which can sheathe and unsheathe the filter assembly 310 from the outer sheath 304.

While not explicitly shown, the filter assembly 310 may, in addition to, or alternatively to, the wire 312, be mounted on a tubular shaft. The tubular shaft may be similar in form and function to the guiding member 60 described above and may be advanced within the lumen 332 of the outer sheath 304. It is contemplated that the tubular shaft may be advanced over a guidewire to facilitate navigation to the left subclavian artery 16. For example, the left subclavian artery 16 may be cannulated with a guidewire and the filter assembly 310 inserted into the left subclavian artery 16 by advancing the tubular shaft over the guidewire.

The distal portion 302 may include fluoroscopic markers to aid a user in positioning the device 300, deploying the filter assembly 310, utilizing the pigtail catheter, etc. A fluoroscopic marker (not explicitly shown) may be positioned proximate to a distal end of the outer sheath 304. Another fluoroscopic marker (not explicitly shown) may be positioned proximate to a proximal end of the filter assembly 310. In some cases, another fluoroscopic marker (not explicitly shown) may be proximate to a distal end of the filter assembly 310. The fluoroscopic markers may comprise a radiopaque material (e.g., iridium, platinum, tantalum, gold, palladium, tungsten, tin, silver, titanium, nickel, zirconium, rhenium, bismuth, molybdenum, combinations thereof, and the like). More or fewer fluoroscopic markers are also possible.

In some methods of use, the filter system 300 may be advanced into the subject through an incision made in the subject's left radial artery, or alternatively the left brachial artery. The system 300 is advanced into the left subclavian artery 16. The device 300 may be positioned, deployed, and retrieved in a similar manner to that described with respect to device 200.

Figure 6:
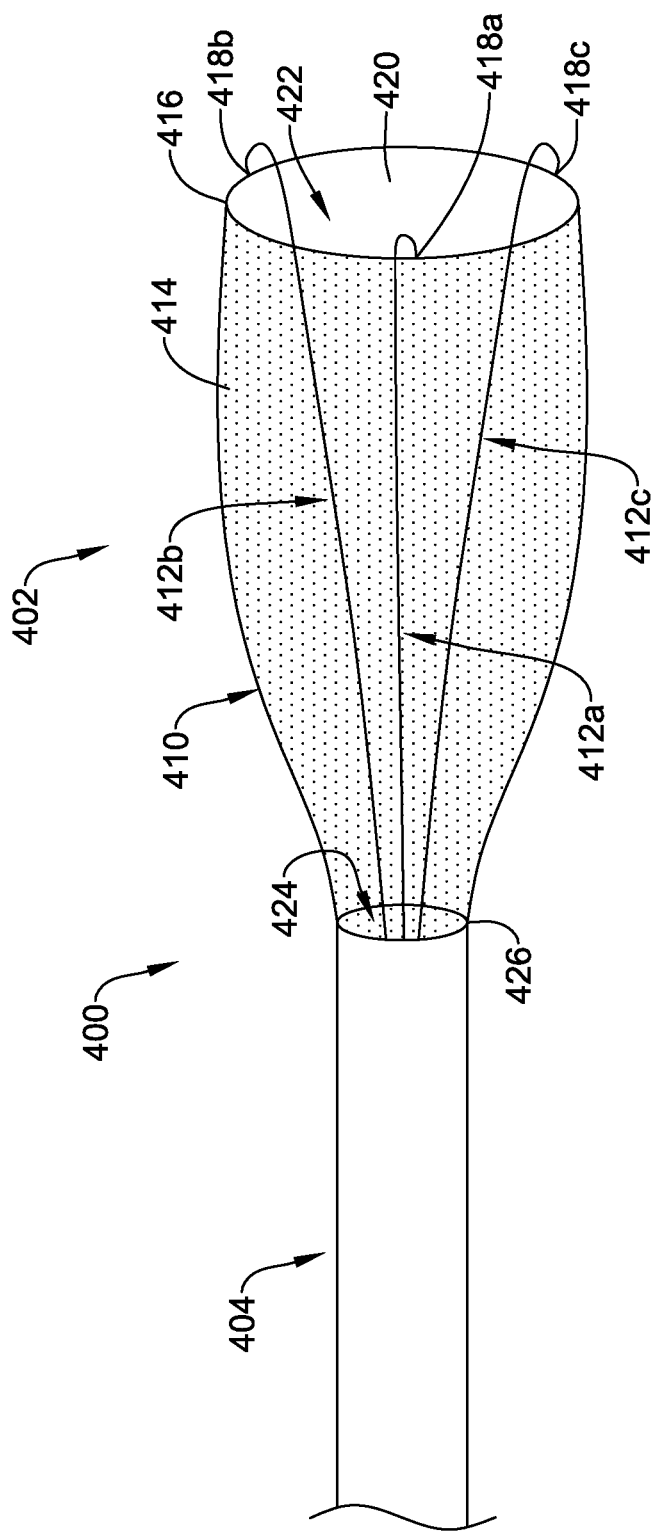
FIG. 6 illustrates another alternative embodiment of a protection device.

FIG. 6 illustrates a side view of another illustrative protection device 400. The protection device 400 may be configured to be positioned in the left subclavian artery 16 and may be similar in form and function the protection device 200 described herein. In some cases, the protection device 400 may be positioned in another vessel or lumen. In some embodiments, the protection device 400 may be used in combination with other protection devices, such as, but not limited to the protection device 30 described herein. The protection device 400 comprises a proximal portion (not explicitly shown) and a distal portion 402. The proximal portion is configured to be held and manipulated by a user such as a surgeon. In some cases, the proximal portion may be coupled to a handle configured to facilitate delivery and deployment of the device 400. In some cases, the handle of the protection device 400 may be similar in form and function to the handles 40, 106 described herein. The distal portion 402 is configured to be positioned at a target location such as the left subclavian artery 16. When the distal portion 402 is configured to be positioned at the left subclavian artery 16, the location may be upstream of the left vertebral artery 24 such that the blood is filtered prior to entering the left vertebral artery 24.

The protection device 400 may include at least an outer sheath 404 and a filter assembly 410. The filter assembly 410 may include a filter element 414 and one or more tethers or wires 412a, 412b, 412c (collectively, 412), or support element, coupled to the filter element 414 adjacent a distal end region 416 thereof. While the filter assembly 410 is illustrated as including three wires 412, the filter assembly 410 may include any number of wires 412, such as, but not limited to one, two, three, four, or more. In some embodiments, the filter assembly 410 may be a stent supported filter. The wires 412 may each include a proximal end (not explicitly shown) configured to remain outside the body. The distal ends 418a, 418b, 418c (collectively, 418) may each be coupled to the distal end region 416 of the filter element 414. The distal ends 418 may be circumferentially spaced about a circumference of the distal end region 416 of the filter element 414. In some cases, the distal ends 418 may be uniformly spaced while in other cases, the distal ends 418 may be eccentrically spaced, as desired. It is contemplated that when the proximal ends of the wires 412 are actuated to collapse or retract the filter assembly 410, the filter assembly 410 may fold more evenly as it is retrieved as it is being inverted from more than one points.

The wires 412 may be similar in form and function to the end rings 124, 126 described herein. For example, the wires 412 may be formed from similar materials, wire shapes, sizes, etc., as the end rings 124, 126. Similarly, the filter element 414 may be similar in form and function to the filter element 128 described herein. In some embodiments, the filter assembly 410 may be self-expanding. In some embodiments, the wires 412 may not provide sufficient expansion support to the filter element 414. The filter element 414 may be formed from a woven or braided nitinol wire that is shape set into a conical (or other shape) to allow apposition to the vessel wall. It is contemplated that other materials and configurations may be used for the filter element 414 which allows the filter element 414 to appose the vessel wall in the expanded configuration. When in the expanded configuration, the filter element 414 is adapted to filter fluid, such as blood, and trap particles flowing therethrough. The filter element 414 has pores therein that are sized to allow the blood to flow therethrough, but are small enough to prevent unwanted foreign particles from passing therethrough. The foreign particles are therefore trapped by and within the filter element 414. As shown in FIG. 6, the filter assembly 410 has a generally distally-facing opening 420. In other embodiments, the opening 420 may be proximally facing. The orientation of the opening 420 may vary depending on where the access incision is located and/or the vessel in which it is deployed.

In some embodiments, the wire 412 and the filter element 414 form an oblique truncated cone having a non-uniform or unequal length around and along the length of the filter assembly 410. In such a configuration, along the lines of a windsock, the filter assembly 410 has a larger opening 420 (upstream) diameter and a reduced ending (downstream) diameter. The filter assembly may define a central lumen 422 extending the length thereof to allow an angiographic or pigtail catheter to pass through the lumen 422. In some embodiments, the wires 412 may extend through the lumen 422. The lumen 422 may include an open proximal end and an open distal end 420. It is contemplated that the open proximal end may be in fluid communication with the central lumen 424 of the outer sheath 404 or other tubular member to direct any captured debris away from the cerebral vasculature. In some cases, the open proximal end of the filter assembly may be positioned within a distal portion of the lumen 424 of the outer sheath 404 or other tubular member. The outer sheath 404 may define a lumen 424 extending from a proximal end to the distal end 426 thereof and may be similar in form and function to the outer sheath 204 described herein.

The filter assembly 410 may be coupled (e.g., crimped, welded, soldered, etc.) to the wire 412. For example, as described above, the wire 412 may be interwoven with the filter element 414. However, it is contemplated that the filter assembly 410 may be coupled to the wire 412 using other methods, including, but not limited to, crimping, welding, soldering, adhesives, hot melting, etc. The wire 412 can be coupled to a handle or a component thereof (not explicitly shown) to provide differential longitudinal movement relative to the outer sheath 404, which can sheathe and unsheathe the filter assembly 410 from the outer sheath 404.

While not explicitly shown, the filter assembly 410 may, in addition to, or alternatively to, the wire 412, be mounted on a tubular shaft. The tubular shaft may be similar in form and function to the guiding member 60 described above and may be advanced within the lumen 424 of the outer sheath 404. It is contemplated that the tubular shaft may be advanced over a guidewire to facilitate navigation to the left subclavian artery 16. For example, the left subclavian artery 16 may be cannulated with a guidewire and the filter assembly 410 inserted into the left subclavian artery 16 by advancing the tubular shaft over the guidewire.

The distal portion 402 may include fluoroscopic markers to aid a user in positioning the device 400, deploying the filter assembly 410, utilizing the pigtail catheter, etc. A fluoroscopic marker (not explicitly shown) may be positioned proximate to a distal end of the outer sheath 404. Another fluoroscopic marker (not explicitly shown) may be positioned proximate to a proximal end of the filter assembly 410. In some cases, another fluoroscopic marker (not explicitly shown) may be proximate to a distal end of the filter assembly 410. The fluoroscopic markers may comprise a radiopaque material (e.g., iridium, platinum, tantalum, gold, palladium, tungsten, tin, silver, titanium, nickel, zirconium, rhenium, bismuth, molybdenum, combinations thereof, and the like). More or fewer fluoroscopic markers are also possible.

In some methods of use, the filter system 400 may be advanced into the subject through an incision made in the subject's left radial artery, or alternatively the left brachial artery. The system 400 is advanced into the left subclavian artery 16. The device 400 may be positioned, deployed, and retrieved in a similar manner to that described with respect to device 200.

Figure 7:
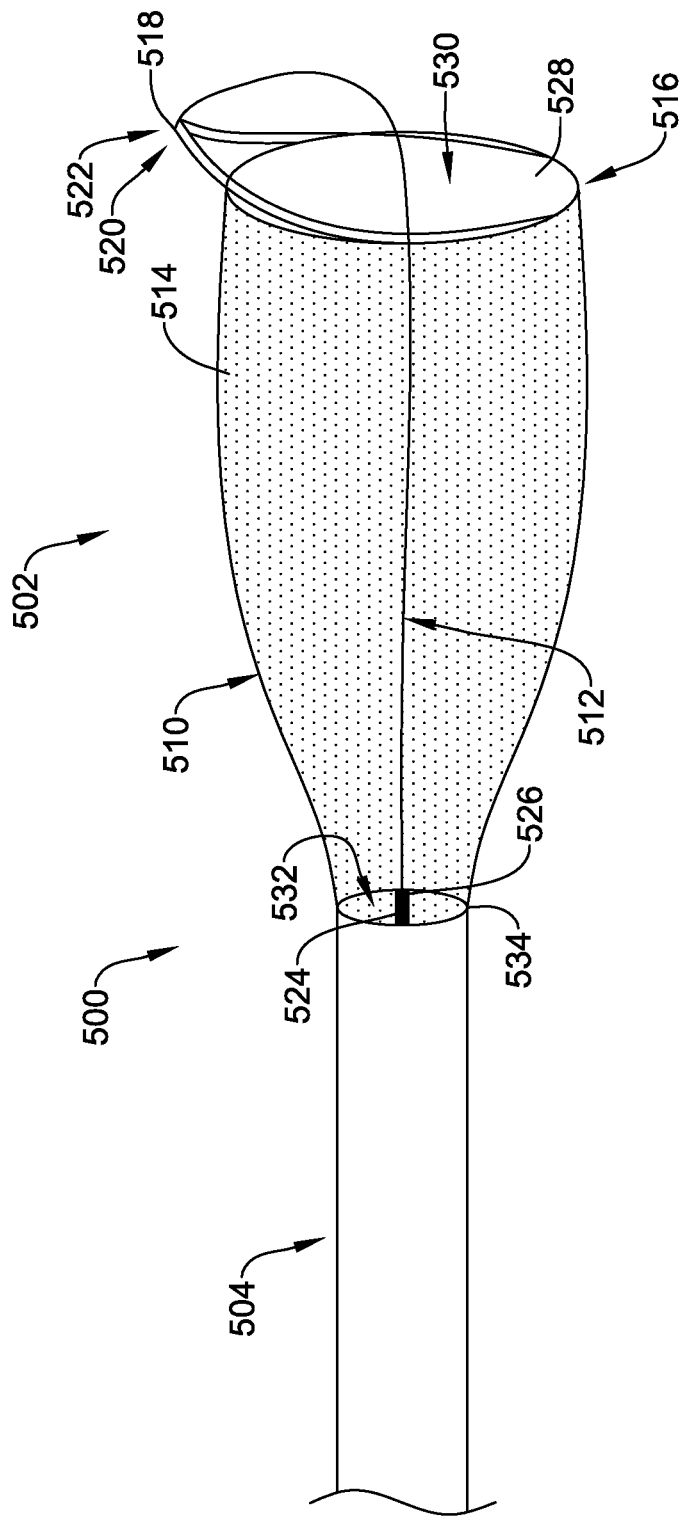
FIG. 7 illustrates another alternative embodiment of a protection device.

FIG. 7 illustrates a side view of another illustrative protection device 500. The protection device 500 may be configured to be positioned in the left subclavian artery 16 and may be similar in form and function the protection device 200 described herein. In some cases, the protection device 500 may be positioned in another vessel or lumen. In some embodiments, the protection device 500 may be used in combination with other protection devices, such as, but not limited to the protection device 30 described herein.

The protection device 500 comprises a proximal portion (not explicitly shown) and a distal portion 502. The proximal portion is configured to be held and manipulated by a user such as a surgeon. In some cases, the proximal portion may be coupled to a handle configured to facilitate delivery and deployment of the device 500. In some cases, the handle of the protection device 500 may be similar in form and function to the handles 40, 106 described herein. The distal portion 502 is configured to be positioned at a target location such as the left subclavian artery 16. When the distal portion 502 is configured to be positioned at the left subclavian artery 16, the location may be upstream of the left vertebral artery 24 such that the blood is filtered prior to entering the left vertebral artery 24.

The protection device 500 may include at least an outer sheath 504 and a filter assembly 510. The filter assembly 510 may include a filter element 514 and a tether or wire 512, or support element, coupled to the filter element 514 adjacent a distal end region 516 thereof. In some embodiments, the filter assembly 510 may be a stent supported filter. The wire 512 may be similar in form and function to the end rings 124, 126 described herein. For example, the wire 512 may be formed from similar materials, wire shapes, sizes, etc., as the end rings 124, 126. Similarly, the filter element 514 may be similar in form and function to the filter element 128 described herein. In some embodiments, the filter assembly 510 may be self-expanding. In some embodiments, the wires 512 may not provide sufficient expansion support to the filter element 514. The filter element 514 may be formed from a braided or woven nitinol wire that is shape set into a conical (or other shape) to allow apposition to the vessel wall. In some cases, the distal ends 520 of the braided material can be gathered at a distal-most portion 522 of the filter element 514. It is contemplated that other materials and configurations may be used for the filter element 514 which allows the filter element 514 to appose the vessel wall in the expanded configuration.

The wires 512 may include a proximal end (not explicitly shown) configured to remain outside the body. The distal end 518 may each be coupled to the distal end region 516 of the filter element 514. In some embodiments, the distal end 518 may be coupled to the gathered distal ends 520 of the filter element 514. This coupling arrangement may allow the filter assembly 510 to be inverted and retrieved from the most distal point 522 of the filter element 514 by proximally withdrawing the wire 512 into the outer sheath 504. In some cases, the wire 512 may extend though a lumen 526 of an inner tubular member 524, although this is not required.

When in the expanded configuration, the filter element 514 is adapted to filter fluid, such as blood, and trap particles flowing therethrough. The filter element 514 has pores therein that are sized to allow the blood to flow therethrough, but are small enough to prevent unwanted foreign particles from passing therethrough. The foreign particles are therefore trapped by and within the filter element 514. As shown in FIG. 7, the filter assembly 510 has a generally distally-facing opening 528. In other embodiments, the opening 528 may be proximally facing. The orientation of the opening 528 may vary depending on where the access incision is located and/or the vessel in which it is deployed.

In some embodiments, the wire 512 and the filter element 514 form an oblique truncated cone having a non-uniform or unequal length around and along the length of the filter assembly 510. In such a configuration, along the lines of a windsock, the filter assembly 510 has a larger opening 528 (upstream) diameter and a reduced ending (downstream) diameter. The filter assembly may define a central lumen 530 extending the length thereof to allow an angiographic or pigtail catheter to pass through the lumen 530. The lumen 530 may include an open proximal end and an open distal end 528. It is contemplated that the open proximal end may be in fluid communication with the central lumen 532 of the outer sheath 504 or other tubular member to direct any captured debris away from the cerebral vasculature. In some cases, the open proximal end of the filter assembly may be positioned within a distal portion of the lumen 532 of the outer sheath 504 or other tubular member. The outer sheath 504 may define a lumen 532 extending from a proximal end to the distal end 534 thereof and may be similar in form and function to the outer sheath 204 described herein.

The filter assembly 510 may be coupled (e.g., crimped, welded, soldered, etc.) to the wire 512. For example, as described above, the wire 512 may be interwoven with the filter element 514. However, it is contemplated that the filter assembly 510 may be coupled to the wire 512 using other methods, including, but not limited to, crimping, welding, soldering, adhesives, hot melting, etc. The wire 512 can be coupled to a handle or a component thereof (not explicitly shown) to provide differential longitudinal movement relative to the outer sheath 504, which can sheathe and unsheathe the filter assembly 510 from the outer sheath 504.

While not explicitly shown, the filter assembly 510 may, in addition to, or alternatively to, the wire 512, be mounted on a tubular shaft, such as the inner tubular member 524. The tubular shaft may be similar in form and function to the guiding member 60 described above and may be advanced within the lumen 532 of the outer sheath 504. It is contemplated that the tubular shaft 524 may be advanced over a guidewire to facilitate navigation to the left subclavian artery 16. For example, the left subclavian artery 16 may be cannulated with a guidewire and the filter assembly 510 inserted into the left subclavian artery 16 by advancing the tubular shaft over the guidewire.

The distal portion 502 may include fluoroscopic markers to aid a user in positioning the device 500, deploying the filter assembly 510, utilizing the pigtail catheter, etc. A fluoroscopic marker (not explicitly shown) may be positioned proximate to a distal end of the outer sheath 504. Another fluoroscopic marker (not explicitly shown) may be positioned proximate to a proximal end of the filter assembly 510. In some cases, another fluoroscopic marker (not explicitly shown) may be proximate to a distal end of the filter assembly 510. The fluoroscopic markers may comprise a radiopaque material (e.g., iridium, platinum, tantalum, gold, palladium, tungsten, tin, silver, titanium, nickel, zirconium, rhenium, bismuth, molybdenum, combinations thereof, and the like). More or fewer fluoroscopic markers are also possible.

In some methods of use, the filter system 500 may be advanced into the subject through an incision made in the subject's left radial artery, or alternatively the left brachial artery. The system 500 is advanced into the left subclavian artery 16. The device 500 may be positioned, deployed, and retrieved in a similar manner to that described with respect to device 200.

Figure 8:
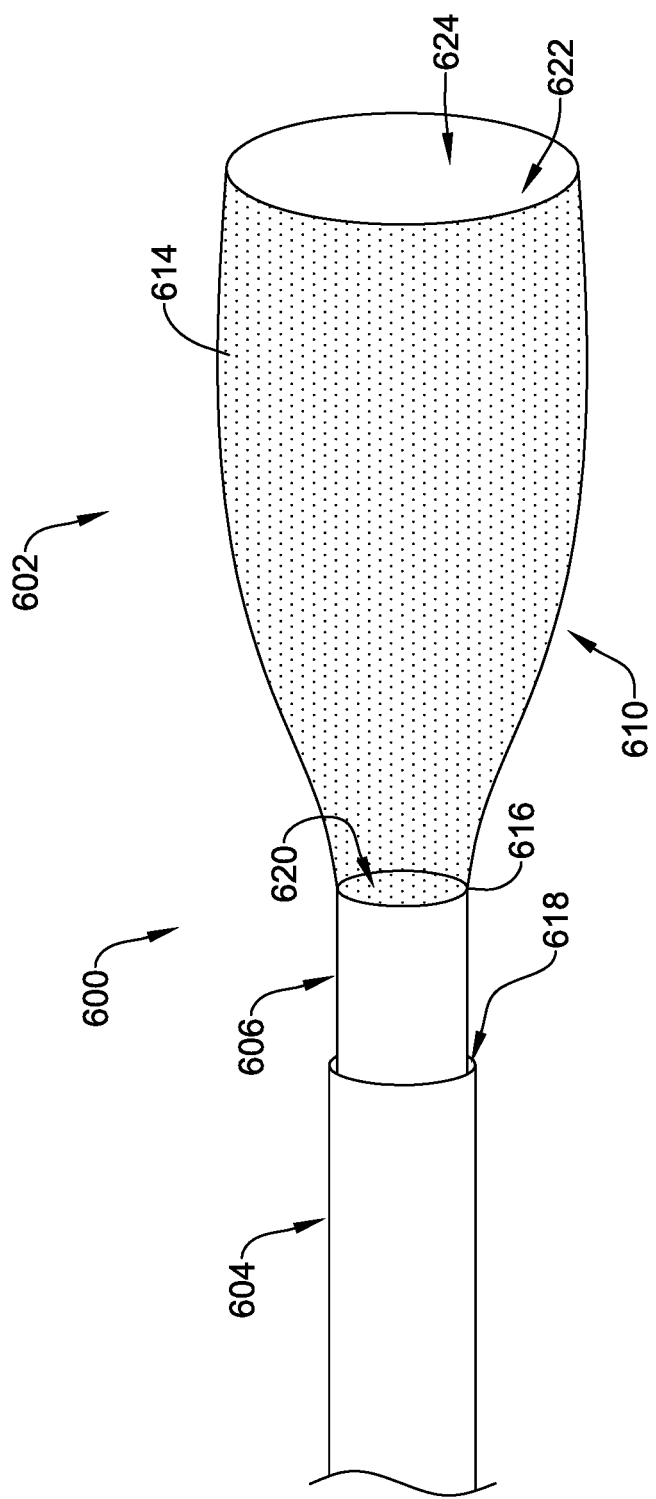
FIG. 8 illustrates another alternative embodiment of a protection device.

FIG. 8 illustrates a side view of another illustrative protection device 600. The protection device 600 may be configured to be positioned in the left subclavian artery 16 and may be similar in form and function the protection device 200 described herein. In some cases, the protection device 600 may be positioned in another vessel or lumen. In some embodiments, the protection device 600 may be used in combination with other protection devices, such as, but not limited to the protection device 30 described herein.

The protection device 600 comprises a proximal portion (not explicitly shown) and a distal portion 602. The proximal portion is configured to be held and manipulated by a user such as a surgeon. In some cases, the proximal portion may be coupled to a handle configured to facilitate delivery and deployment of the device 600. In some cases, the handle of the protection device 600 may be similar in form and function to the handles 40, 106 described herein. The distal portion 602 is configured to be positioned at a target location such as the left subclavian artery 16. When the distal portion 602 is configured to be positioned at the left subclavian artery 16, the location may be upstream of the left vertebral artery 24 such that the blood is filtered prior to entering the left vertebral artery 24.

The protection device 600 may include at least an outer sheath 604, an inner shaft or tubular member 606, and a filter assembly 610. The filter assembly 610 may include a filter element 614. The filter element may be similar in form and function to the filter element 128 described herein. In some embodiments, the filter element 614 may be self-supporting. For example, the filter element 614 may be formed from a braided or woven nitinol wire that is shape set into a conical (or other shape) to allow apposition to the vessel wall. In some cases, while not explicitly shown, the filter element 614 may be formed from a more flexible porous material and expanded with an expanding frame or wire. In some embodiments, the filter element 614 may be manually expanded through an actuation device. It is contemplated that other materials and configurations may be used for the filter element 614 which allows the filter element 614 to appose the vessel wall in the expanded configuration.

The filter assembly 610 may be coupled to a distal end region 616 of the inner tubular member 606. The inner tubular member 606 may be slidably disposed within and extend through a lumen 618 of the outer sheath 604. The inner tubular member may have an outer diameter that is smaller than the inner diameter of the outer sheath 604 and a minimum inner diameter seized to fit an angiographic catheter through a lumen 620 of the inner tubular member 606 and the filter assembly 610 with minimal resistance. It is contemplated that the inner tubular member may be a laser cut stainless steel tube or a braided shaft configured or designed to withstand the sheathing and deployment forces of the filter assembly 610.

The filter assembly 610 may be disposed within the outer sheath 604 as the device 600 is advanced to the desired location. The outer sheath 604 may be configured to maintain the filter assembly 610 in a radially collapsed configuration for navigation through the vasculature. It is further contemplated that the inner tubular member 606 may be axially and rotationally movable independent of the outer sheath 604. For example, the inner tubular member 606 may be distally advanced, the outer sheath 604 proximally retracted, or combinations thereof to deploy the filter assembly 610. To recapture the filter assembly 610, the outer sheath 604 can be distally advanced over the filter assembly 610, the inner tubular member 606 can be proximally retracted within the lumen 618 of the outer sheath 604, or combinations thereof.

When in the expanded configuration, the filter element 614 is adapted to filter fluid, such as blood, and trap particles flowing therethrough. The filter element 614 has pores therein that are sized to allow the blood to flow therethrough, but are small enough to prevent unwanted foreign particles from passing therethrough. The foreign particles are therefore trapped by and within the filter element 614. As shown in FIG. 8, the filter assembly 610 has a generally distally-facing opening 622. In other embodiments, the opening 622 may be proximally facing. The orientation of the opening 622 may vary depending on where the access incision is located and/or the vessel in which it is deployed.

In some embodiments, the filter element 614 forms an oblique truncated cone having a non-uniform or unequal length around and along the length of the filter assembly 610. In such a configuration, along the lines of a windsock, the filter assembly 610 has a larger opening 622 (upstream) diameter and a reduced ending (downstream) diameter. The filter assembly 610 may define a central lumen 624 extending the length thereof to allow an angiographic or pigtail catheter to pass through the lumen 624. The lumen 624 may include an open proximal end and an open distal end 622. It is contemplated that the open proximal end may be in fluid communication with the central lumen 620 of the inner tubular member 606 or other tubular member to direct any captured debris away from the cerebral vasculature. In some cases, the open proximal end of the filter assembly 610 may be coupled to or within a distal portion of the inner tubular member 606.

As described herein, the filter assembly 610 may be coupled to the inner tubular member 606. It is contemplated that the filter assembly 610 may be coupled to the inner tubular member 606 using any method desired, including, but not limited to, crimping, welding, soldering, adhesives, hot melting, etc. The inner tubular member 606 can be coupled to a handle or a component thereof (not explicitly shown) to provide differential longitudinal movement relative to the outer sheath 604, which can sheathe and unsheathe the filter assembly 610 from the outer sheath 604.

The distal portion 602 may include fluoroscopic markers to aid a user in positioning the device 600, deploying the filter assembly 610, utilizing the pigtail catheter, etc. A fluoroscopic marker (not explicitly shown) may be positioned proximate to a distal end of the outer sheath 604. Another fluoroscopic marker (not explicitly shown) may be positioned proximate to a proximal end of the filter assembly 610. In some cases, another fluoroscopic marker (not explicitly shown) may be proximate to a distal end of the filter assembly 610. The fluoroscopic markers may comprise a radiopaque material (e.g., iridium, platinum, tantalum, gold, palladium, tungsten, tin, silver, titanium, nickel, zirconium, rhenium, bismuth, molybdenum, combinations thereof, and the like). More or fewer fluoroscopic markers are also possible.

In some methods of use, the filter system 600 may be advanced into the subject through an incision made in the subject's left radial artery, or alternatively the left brachial artery. The system 600 is advanced into the left subclavian artery 16. The device 600 may be positioned, deployed, and retrieved in a similar manner to that described with respect to device 200.

Figure 9:
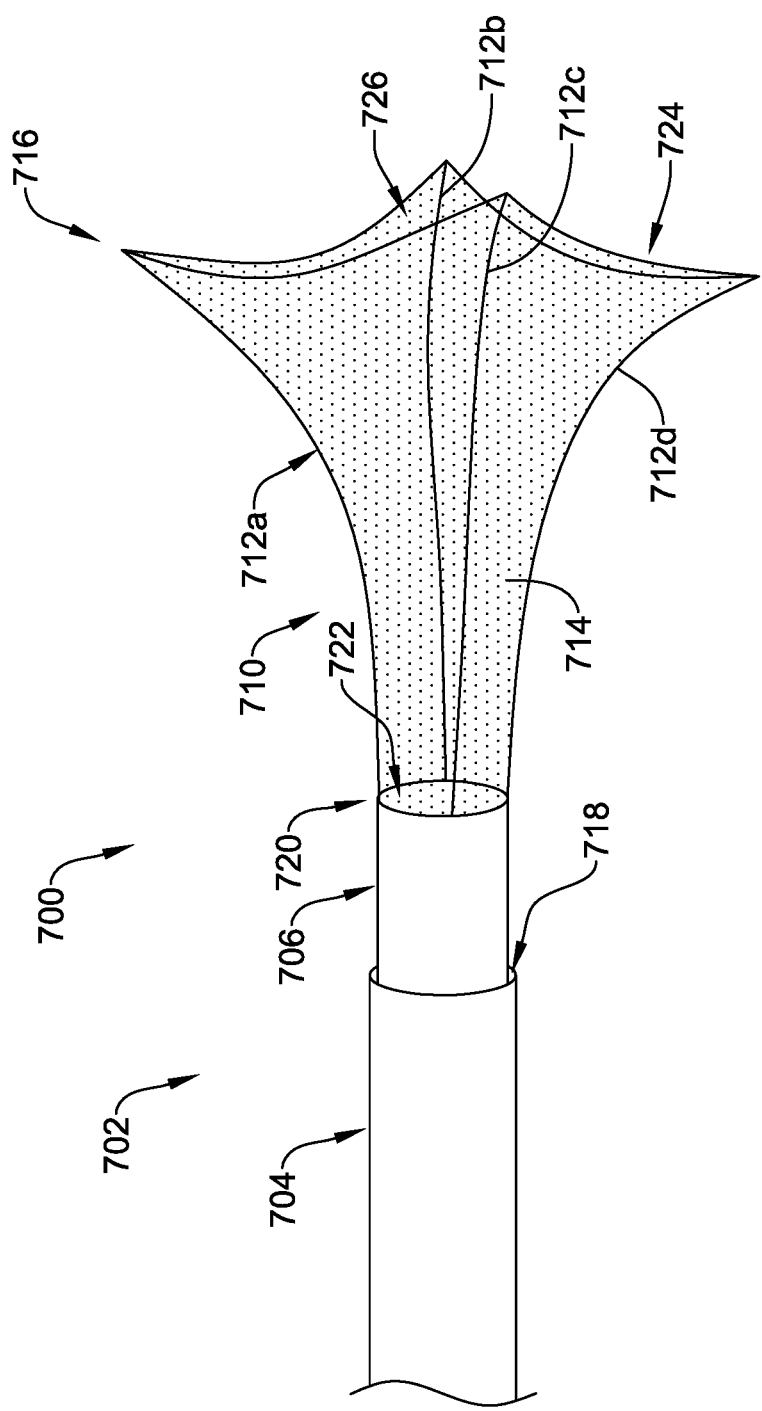
FIG. 9 illustrates another alternative embodiment of a protection device.

FIG. 9 illustrates a side view of another illustrative protection device 700. The protection device 700 may be configured to be positioned in the left subclavian artery 16 and may be similar in form and function the protection device 200 described herein. In some cases, the protection device 700 may be positioned in another vessel or lumen. In some embodiments, the protection device 700 may be used in combination with other protection devices, such as, but not limited to the protection device 30 described herein.

The protection device 700 comprises a proximal portion (not explicitly shown) and a distal portion 702. The proximal portion is configured to be held and manipulated by a user such as a surgeon. In some cases, the proximal portion may be coupled to a handle configured to facilitate delivery and deployment of the device 700. In some cases, the handle of the protection device 700 may be similar in form and function to the handles 40, 106 described herein. The distal portion 702 is configured to be positioned at a target location such as the left subclavian artery 16. When the distal portion 702 is configured to be positioned at the left subclavian artery 16, the location may be upstream of the left vertebral artery 24 such that the blood is filtered prior to entering the left vertebral artery 24.

The protection device 700 may include at least an outer sheath 704, an inner shaft or inner tubular member 706, and a filter assembly 710. The filter assembly 710 may include a support frame including a plurality of longitudinally extending legs 712a, 712b, 712c, 712d (collectively, 712) and a filter element 714. The legs 712 may be similar in form and function to the end rings 124, 126 described herein. For example, the legs 712 may be formed from similar materials, wire shapes, sizes, etc., as the end rings 124, 126. The filter element 714 may be coupled to the plurality of legs 712 adjacent to a distal end 716 of the filter element 714 and/or continuously or intermittently along a length of the filter element 714. While the filter assembly 710 is illustrated as including four legs 712, the filter assembly 710 may include any number of legs 712, such as, but not limited to one, two, three, four, or more. It is contemplated that the number of legs 712 may be varied to change the wall apposition of the filter assembly 710. For example, increasing a number of legs 712 may increase the wall apposition. In some embodiments, the legs 712 may have a length approximately equal to a length of the filter element 714. In other embodiments, the legs 712 may have a length longer than the filter element 714. For example, the legs 712 may extend to a proximal end of the device 700 to facilitate removal of the filter assembly 710.

In some embodiments, the filter assembly 710 may be a stent supported filter. The filter element may be similar in form and function to the filter element 128 described herein. For example, the filter element 714 may be formed from a drilled or perforated membrane extending between the legs 712. In some cases, while not explicitly shown, the filter element 714 may be formed from a woven or braided structure. In some embodiments, the filter element 714 may be manually expanded through an actuation device. It is contemplated that other materials and configurations may be used for the filter element 714 which allows the filter element 714 to appose the vessel wall in the expanded configuration.

The filter assembly 710 may be coupled to a distal end region 720 of the inner tubular member 706. The inner tubular member 706 may be slidably disposed within and extend through a lumen 718 of the outer sheath 704. The inner tubular member may have an outer diameter that is smaller than the inner diameter of the outer sheath 704 and a minimum inner diameter seized to fit an angiographic catheter through a lumen 722 of the inner tubular member 706 and the filter assembly 710 with minimal resistance. It is contemplated that the inner tubular member may be a laser cut stainless steel tube or a braided shaft configured or designed to withstand the sheathing and deployment forces of the filter assembly 710.

The filter assembly 710 may be disposed within the outer sheath 704 as the device 700 is advanced to the desired location. The outer sheath 704 may be configured to maintain the filter assembly 710 in a radially collapsed configuration for navigation through the vasculature. It is further contemplated that the inner tubular member 706 may be axially and rotationally movable independent of the outer sheath 704. For example, the inner tubular member 706 may be distally advanced, the outer sheath 704 proximally retracted, or combinations thereof to deploy the filter assembly 710. As the filter assembly 710 is deployed, the legs 712 may open the filter element 714 to the size of the vessel. To recapture the filter assembly 710, the outer sheath 704 can be distally advanced over the filter assembly 710, the inner tubular member 706 can be proximally retracted within the lumen 718 of the outer sheath 704, or combinations thereof.

When in the expanded configuration, the filter element 714 is adapted to filter fluid, such as blood, and trap particles flowing therethrough. The filter element 714 has pores therein that are sized to allow the blood to flow therethrough, but are small enough to prevent unwanted foreign particles from passing therethrough. The foreign particles are therefore trapped by and within the filter element 714. As shown in FIG. 9, the filter assembly 710 has a generally distally-facing opening 724. In some cases, the shape of the opening 724 may vary depending on the number of legs 712 supporting the filter element 714. In other embodiments, the opening 724 may be proximally facing. The orientation of the opening 724 may vary depending on where the access incision is located and/or the vessel in which it is deployed.

In some embodiments, the filter element 714 forms an oblique truncated cone having a non-uniform or unequal length around and along the length of the filter assembly 710. In such a configuration, along the lines of a windsock, the filter assembly 710 has a larger opening 724 (upstream) diameter and a reduced ending (downstream) diameter. The filter assembly 710 may define a central lumen 726 extending the length thereof to allow an angiographic or pigtail catheter to pass through the lumen 726. The lumen 726 may include an open proximal end and an open distal end 724. It is contemplated that the open proximal end may be in fluid communication with the central lumen 722 of the inner tubular member 706 or other tubular member to direct any captured debris away from the cerebral vasculature. In some cases, the open proximal end of the filter assembly 710 may be coupled to or within a distal portion of the inner tubular member 706.

As described herein, the filter assembly 710 may be coupled to the inner tubular member 706. It is contemplated that the filter assembly 710 may be coupled to the inner tubular member 706 using any method desired, including, but not limited to, crimping, welding, soldering, adhesives, hot melting, etc. The inner tubular member 706 can be coupled to a handle or a component thereof (not explicitly shown) to provide differential longitudinal movement relative to the outer sheath 704, which can sheathe and unsheathe the filter assembly 710 from the outer sheath 704.

The distal portion 702 may include fluoroscopic markers to aid a user in positioning the device 700, deploying the filter assembly 710, utilizing the pigtail catheter, etc. A fluoroscopic marker (not explicitly shown) may be positioned proximate to a distal end of the outer sheath 704. Another fluoroscopic marker (not explicitly shown) may be positioned proximate to a proximal end of the filter assembly 710. In some cases, another fluoroscopic marker (not explicitly shown) may be proximate to a distal end of the filter assembly 710. The fluoroscopic markers may comprise a radiopaque material (e.g., iridium, platinum, tantalum, gold, palladium, tungsten, tin, silver, titanium, nickel, zirconium, rhenium, bismuth, molybdenum, combinations thereof, and the like). More or fewer fluoroscopic markers are also possible.

In some methods of use, the filter system 700 may be advanced into the subject through an incision made in the subject's left radial artery, or alternatively the left brachial artery. The system 700 is advanced into the left subclavian artery 16. The device 700 may be positioned, deployed, and retrieved in a similar manner to that described with respect to device 200.

Figure 10:
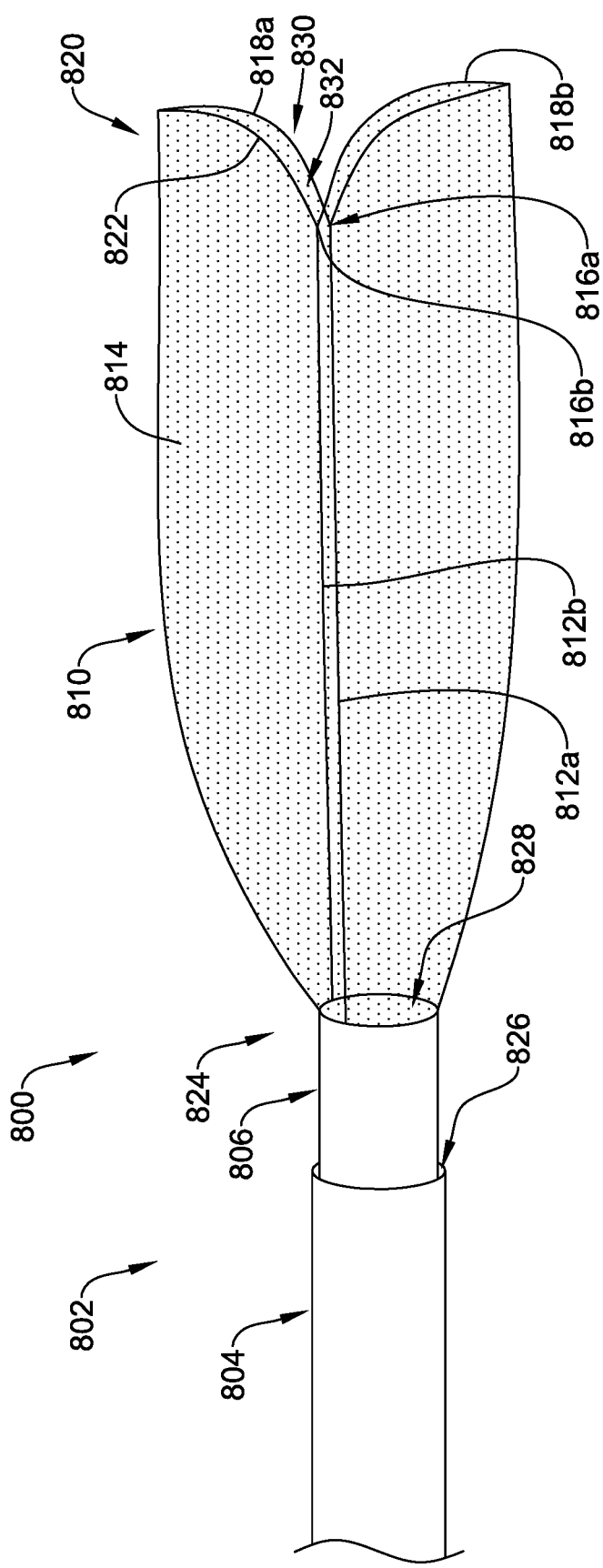
FIG. 10 illustrates another alternative embodiment of a protection device.

FIG. 10 illustrates a side view of another illustrative protection device 800. The protection device 800 may be configured to be positioned in the left subclavian artery 16 and may be similar in form and function the protection device 200 described herein. In some cases, the protection device 800 may be positioned in another vessel or lumen. In some embodiments, the protection device 800 may be used in combination with other protection devices, such as, but not limited to the protection device 30 described herein.

The protection device 800 comprises a proximal portion (not explicitly shown) and a distal portion 802. The proximal portion is configured to be held and manipulated by a user such as a surgeon. In some cases, the proximal portion may be coupled to a handle configured to facilitate delivery and deployment of the device 800. In some cases, the handle of the protection device 800 may be similar in form and function to the handles 40, 106 described herein. The distal portion 802 is configured to be positioned at a target location such as the left subclavian artery 16. When the distal portion 802 is configured to be positioned at the left subclavian artery 16, the location may be upstream of the left vertebral artery 24 such that the blood is filtered prior to entering the left vertebral artery 24.

The protection device 800 may include at least an outer sheath 804, an inner shaft or inner tubular member 806, and a filter assembly 810 including a filter element 814. The filter assembly 810 may further include a support frame including a plurality of longitudinally extending legs 812a, 812b (collectively, 812), a ring 822 having a first portion 818a and a second portion 818b (collectively, 818), and a pair of hinges 816a, 816b (collectively, 816). The legs 812 may be similar in form and function to the end rings 124, 126 described herein. For example, the legs 812 may be formed from similar materials, wire shapes, sizes, etc., as the end rings 124, 126. In some embodiments, the hinges 816 may movingly couple the first and second portions 818a, 818b of the distal ring. Each leg 812a, 812b may be coupled to a respective hinge 816a, 816b. In some cases, the hinges 816 and the ring 822 may be positioned and coupled to adjacent to a distal end region 820 of the filter element 810. However, the hinges 816 and/or the ring 822 may be positioned anywhere between a distal end region 824 of the inner tubular member 806 and the distal end region 820 of the filter element 810. The hinges 816 may be configured to facilitate collapse and/or expansion of the filter assembly 810, as desired.

The filter element 814 may be coupled to the plurality of legs 812 and/or the ring 822 adjacent to a distal end 820 of the filter element 814 and/or continuously or intermittently along a length of the filter element 814. While the filter assembly 810 is illustrated as including two legs 812, the filter assembly 810 may include any number of legs 812, such as, but not limited to one, two, three, four, or more. It is contemplated that the number of legs 812 may be varied to change the wall apposition of the filter assembly 810. For example, increasing a number of legs 812 may increase the wall apposition. In some embodiments, the legs 812 may have a length approximately equal to a length of the filter element 814. In other embodiments, the legs 812 may have a length longer than the filter element 814. For example, the legs 812 may extend to a proximal end of the device 800 to facilitate removal of the filter assembly 810 by acting as a pull wire or may be coupled to a pull wire (in addition to or in place of the inner tubular member 806).

In some embodiments, the filter assembly 810 may be a stent supported filter. The filter element may be similar in form and function to the filter element 128 described herein. For example, the filter element 814 may be formed from a drilled or perforated membrane extending between the legs 812. In some cases, while not explicitly shown, the filter element 814 may be formed from a woven or braided structure. In some embodiments, the filter element 814 may be manually expanded through an actuation device. It is contemplated that other materials and configurations may be used for the filter element 814 which allows the filter element 814 to appose the vessel wall in the expanded configuration.

The filter assembly 810 may be coupled to a distal end region 824 of the inner tubular member 806. The inner tubular member 806 may be slidably disposed within and extend through a lumen 826 of the outer sheath 804. The inner tubular member may have an outer diameter that is smaller than the inner diameter of the outer sheath 804 and a minimum inner diameter seized to fit an angiographic catheter through a lumen 828 of the inner tubular member 806 and the filter assembly 810 with minimal resistance. It is contemplated that the inner tubular member may be a laser cut stainless steel tube or a braided shaft configured or designed to withstand the sheathing and deployment forces of the filter assembly 810.

The filter assembly 810 may be disposed within the outer sheath 804 as the device 800 is advanced to the desired location. The outer sheath 804 may be configured to maintain the filter assembly 810 in a radially collapsed configuration for navigation through the vasculature. It is further contemplated that the inner tubular member 806 may be axially and rotationally movable independent of the outer sheath 804. For example, the inner tubular member 806 may be distally advanced, the outer sheath 804 proximally retracted, or combinations thereof to deploy the filter assembly 810. As the filter assembly 810 is deployed, the legs 812 may open the filter element 814 to the size of the vessel. To recapture the filter assembly 810, the outer sheath 804 can be distally advanced over the filter assembly 810, the inner tubular member 806 can be proximally retracted within the lumen 826 of the outer sheath 804, or combinations thereof.

When in the expanded configuration, the filter element 814 is adapted to filter fluid, such as blood, and trap particles flowing therethrough. The filter element 814 has pores therein that are sized to allow the blood to flow therethrough, but are small enough to prevent unwanted foreign particles from passing therethrough. The foreign particles are therefore trapped by and within the filter element 814. As shown in FIG. 10, the filter assembly 810 has a generally distally-facing opening 830. In other embodiments, the opening 830 may be proximally facing. The orientation of the opening 830 may vary depending on where the access incision is located and/or the vessel in which it is deployed.

In some embodiments, the filter element 814 forms an oblique truncated cone having a non-uniform or unequal length around and along the length of the filter assembly 810. In such a configuration, along the lines of a windsock, the filter assembly 810 has a larger opening 830 (upstream) diameter and a reduced ending (downstream) diameter. The filter assembly 810 may define a central lumen 832 extending the length thereof to allow an angiographic or pigtail catheter to pass through the lumen 832. The lumen 832 may include an open proximal end and an open distal end 830. It is contemplated that the open proximal end may be in fluid communication with the central lumen 828 of the inner tubular member 806 or other tubular member to direct any captured debris away from the cerebral vasculature. In some cases, the open proximal end of the filter assembly 810 may be coupled to or within a distal portion of the inner tubular member 806.

As described herein, the filter assembly 810 may be coupled to the inner tubular member 806. It is contemplated that the filter assembly 810 may be coupled to the inner tubular member 806 using any method desired, including, but not limited to, crimping, welding, soldering, adhesives, hot melting, etc. The inner tubular member 806 can be coupled to a handle or a component thereof (not explicitly shown) to provide differential longitudinal movement relative to the outer sheath 804, which can sheathe and unsheathe the filter assembly 810 from the outer sheath 804.

The distal portion 802 may include fluoroscopic markers to aid a user in positioning the device 800, deploying the filter assembly 810, utilizing the pigtail catheter, etc. A fluoroscopic marker (not explicitly shown) may be positioned proximate to a distal end of the outer sheath 804. Another fluoroscopic marker (not explicitly shown) may be positioned proximate to a proximal end of the filter assembly 810. In some cases, another fluoroscopic marker (not explicitly shown) may be proximate to a distal end of the filter assembly 810. The fluoroscopic markers may comprise a radiopaque material (e.g., iridium, platinum, tantalum, gold, palladium, tungsten, tin, silver, titanium, nickel, zirconium, rhenium, bismuth, molybdenum, combinations thereof, and the like). More or fewer fluoroscopic markers are also possible.

In some methods of use, the filter system 800 may be advanced into the subject through an incision made in the subject's left radial artery, or alternatively the left brachial artery. The system 800 is advanced into the left subclavian artery 16. The device 800 may be positioned, deployed, and retrieved in a similar manner to that described with respect to device 200.

Figure 11:
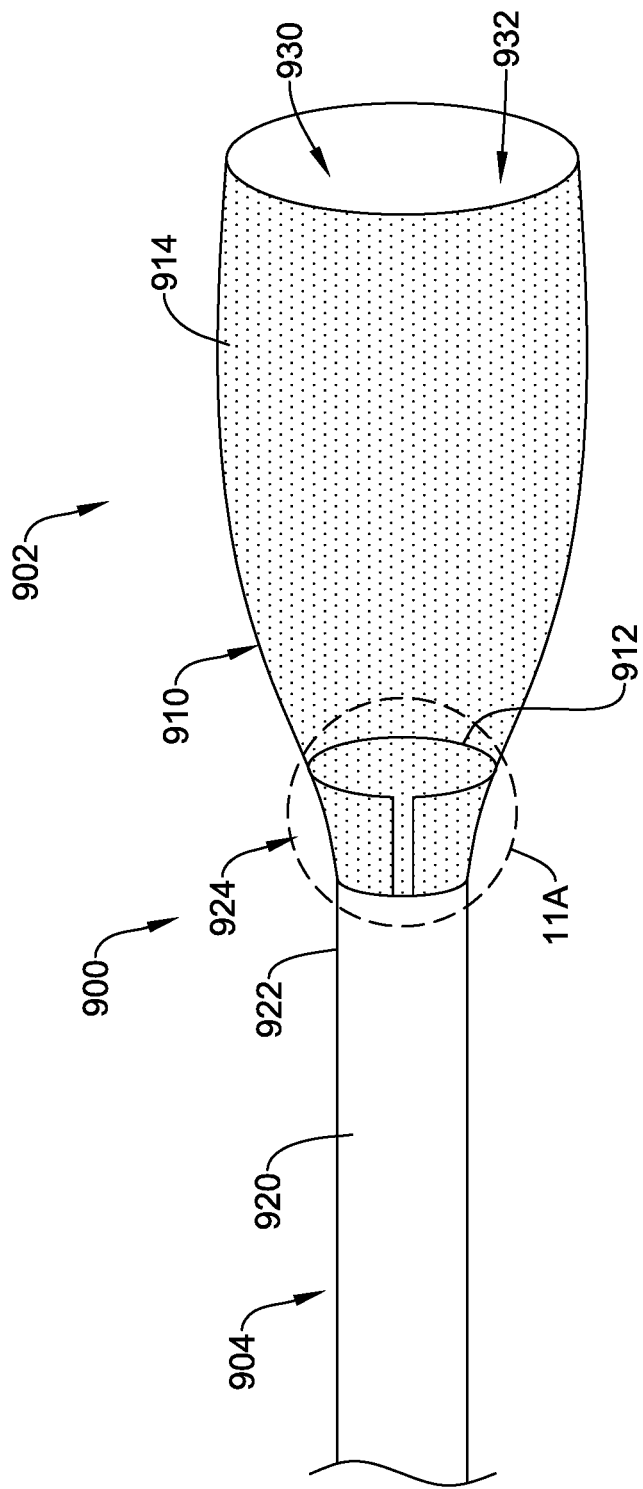
FIG. 11 illustrates another alternative embodiment of a protection device.

FIG. 11 illustrates a side view of another illustrative protection device 900. The protection device 900 may be configured to be positioned in the left subclavian artery 16 and may be similar in form and function the protection device 200 described herein. In some cases, the protection device 900 may be positioned in another vessel or lumen. In some embodiments, the protection device 900 may be used in combination with other protection devices, such as, but not limited to the protection device 30 described herein.

The protection device 900 comprises a proximal portion (not explicitly shown) and a distal portion 902. The proximal portion is configured to be held and manipulated by a user such as a surgeon. In some cases, the proximal portion may be coupled to a handle configured to facilitate delivery and deployment of the device 900. In some cases, the handle of the protection device 900 may be similar in form and function to the handles 40, 106 described herein. The distal portion 902 is configured to be positioned at a target location such as the left subclavian artery 16. When the distal portion 902 is configured to be positioned at the left subclavian artery 16, the location may be upstream of the left vertebral artery 24 such that the blood is filtered prior to entering the left vertebral artery 24.

Figure 11A:
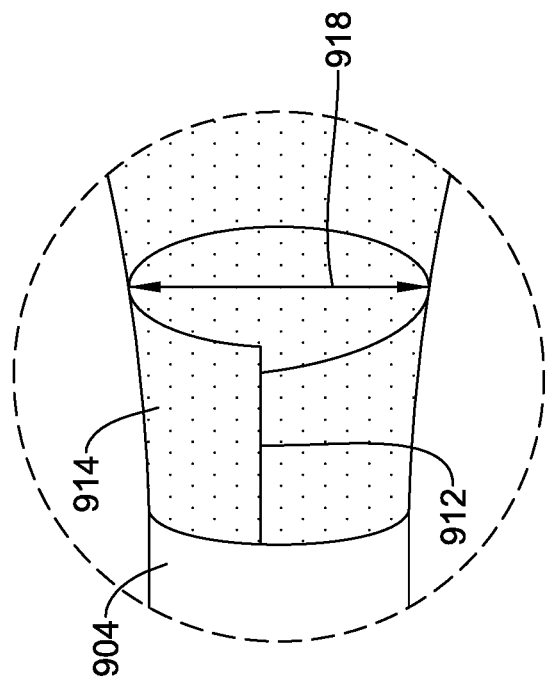
FIG. 11A is an enlarged view of a portion of the protection device of FIG. 11 in a first configuration.
Figure 11B:
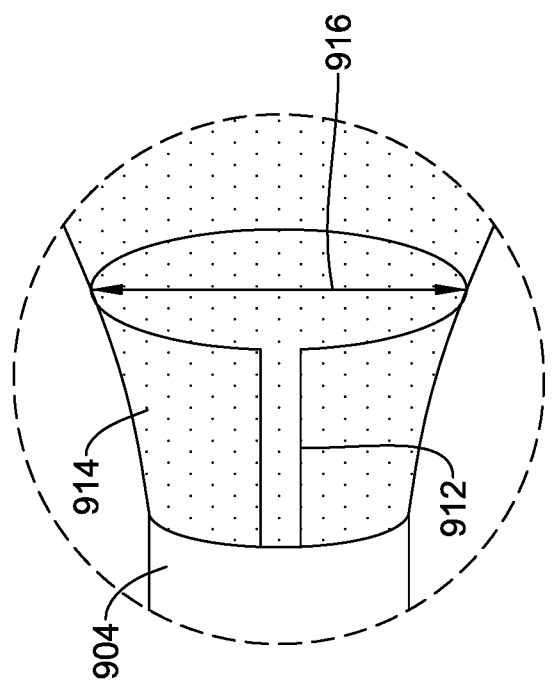
FIG. 11B is an enlarged view of a portion of the protection device of FIG. 11 in a second configuration.

The protection device 900 may include at least an outer sheath 904, an angiographic catheter (not explicitly shown), and a filter assembly 910 including a filter element 914. The filter assembly 910 may further include an expandable support structure 912. The support structure 912 may be woven into or otherwise attached to the filter element 914, in a similar manner to that described with respect to wire 212. The support structure 912 may be similar in form and function to the end rings 124, 126 described herein. For example, the support structure 912 may be formed from similar materials, wire shapes, sizes, etc., as the end rings 124, 126. Referring additionally to FIG. 11A, which illustrates an enlarged view of the support structure 912 in a fully expanded configuration, the support structure 912 may have a first cross-sectional or radial dimension 916 in a fully expanded configuration. As the filter assembly 910 is partially collapsed (as the filter assembly 910 is withdrawn into the outer sheath 904), the support structure 912 may have a second cross-sectional or radial dimension 918 that is smaller than the first cross-sectional or radial dimension 916, as shown in FIG. 11B which illustrates an enlarged view of the support structure 912 in a partially collapsed configuration. In the fully collapsed configuration, the cross-sectional or radial dimension may be smaller than both the first and second cross-sectional or radial dimension 916, 918. It is contemplated the cross-sectional or radial dimension of the support structure in the fully collapsed configuration may be smaller than an outer diameter of an angiographic catheter or pusher element. This may allow the angiographic catheter or pusher element to push against the support structure 912 to facilitate deployment of the filter assembly 910. For example, as the catheter or pusher element is through a lumen 920 of the outer sheath 904, the catheter or pusher element abuts the support structure 912 and pushes the support structure 912 out of the distal end 922 of the outer sheath 904 where it expands to seal against the lumen. It is contemplated that the support structure 912 may be resheathed by pulling on a pull wire (not explicitly shown) attached to the support structure 912.

Figure 11C:
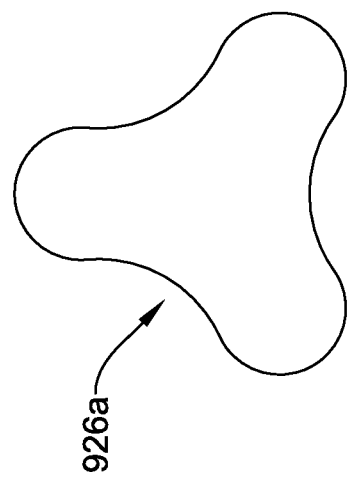
FIG. 11C is an end view of the protection device of FIG. 11 in a third configuration.
Figure 11D:
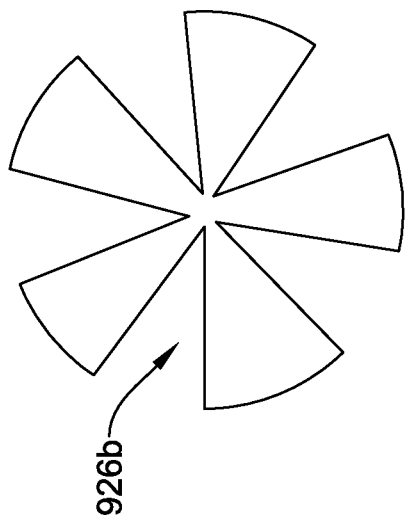
FIG. 11D is an end view of the protection device of FIG. 11 in an alternative third configuration.

In some embodiments, the support structure 912 may be positioned adjacent to a proximal end region 924 of the filter element 914, although this is not required. In some cases, the support structure 912 may be a shape memory structure made of, for example, but not limited to, nitinol. In some cases, the support structure 912 may be a slotted tube that coils up when sheathed. It is contemplated that the support structure 912 may include other features configured to reduce the cross-sectional dimension thereof when in a collapsed configuration. It is contemplated that the cross-sectional dimension of the support structure 912 in the collapsed configuration may take any shape desired, as long as the cross-sectional dimension has a smaller inner diameter than the outer diameter of the angiographic catheter or pusher element. Some illustrative, but non-limiting cross-sectional shapes 926a, 926b are illustrated in FIGS. 11C and 11D.

In some embodiments, the filter assembly 910 may be a stent supported filter. The filter element 914 may be similar in form and function to the filter element 128 described herein. For example, the filter element 914 may be formed from a drilled or perforated membrane extending between the legs 912. In some cases, the filter element 914 may be formed from a woven or braided structure. In some embodiments, the filter element 914 may be manually expanded through an actuation device. It is contemplated that other materials and configurations may be used for the filter element 914 which allows the filter element 914 to appose the vessel wall in the expanded configuration.

The filter assembly 910 may be coupled to a pull wire (not explicitly shown) and loaded within the lumen 920 of the outer sheath 904. The filter assembly 910 may be disposed within the outer sheath 904 as the device 900 is advanced to the desired location. The outer sheath 904 may be configured to maintain the filter assembly 910 in a radially collapsed configuration for navigation through the vasculature. As described above, an angiographic catheter or pusher element may be distally advanced to deploy the filter assembly 910. In some cases, the outer sheath 904 may be proximally retracted substantially simultaneously therewith. As the filter assembly 910 is deployed, the support structure 912 may open the filter element 914 to the size of the vessel. To recapture the filter assembly 910, the outer sheath 904 can be distally advanced over the filter assembly 910, the filter assembly 910 proximally retracted (e.g., via a pull wire), or combinations thereof.

When in the expanded configuration, the filter element 914 is adapted to filter fluid, such as blood, and trap particles flowing therethrough. The filter element 914 has pores therein that are sized to allow the blood to flow therethrough, but are small enough to prevent unwanted foreign particles from passing therethrough. The foreign particles are therefore trapped by and within the filter element 914. As shown in FIG. 11, the filter assembly 910 has a generally distally-facing opening 930. In other embodiments, the opening 930 may be proximally facing. The orientation of the opening 930 may vary depending on where the access incision is located and/or the vessel in which it is deployed.

In some embodiments, the filter element 914 forms an oblique truncated cone having a non-uniform or unequal length around and along the length of the filter assembly 910. In such a configuration, along the lines of a windsock, the filter assembly 910 has a larger opening 930 (upstream) diameter and a reduced ending (downstream) diameter. The filter assembly 910 may define a central lumen 932 extending the length thereof to allow an angiographic or pigtail catheter to pass through the lumen 932. The lumen 932 may include an open proximal end and an open distal end 930. It is contemplated that the open proximal end may be in fluid communication with the central lumen 928 of the inner tubular member 906 or other tubular member to direct any captured debris away from the cerebral vasculature. In some cases, the open proximal end of the filter assembly 910 may be coupled to or within a distal portion of the inner tubular member 906.

As described herein, the filter assembly 910 may be coupled to the inner tubular member 906. It is contemplated that the filter assembly 910 may be coupled to the inner tubular member 906 using any method desired, including, but not limited to, crimping, welding, soldering, adhesives, hot melting, etc. The inner tubular member 906 can be coupled to a handle or a component thereof (not explicitly shown) to provide differential longitudinal movement relative to the outer sheath 904, which can sheathe and unsheathe the filter assembly 910 from the outer sheath 904.

The distal portion 902 may include fluoroscopic markers to aid a user in positioning the device 900, deploying the filter assembly 910, utilizing the pigtail catheter, etc. A fluoroscopic marker (not explicitly shown) may be positioned proximate to a distal end of the outer sheath 904. Another fluoroscopic marker (not explicitly shown) may be positioned proximate to a proximal end of the filter assembly 910. In some cases, another fluoroscopic marker (not explicitly shown) may be proximate to a distal end of the filter assembly 910. The fluoroscopic markers may comprise a radiopaque material (e.g., iridium, platinum, tantalum, gold, palladium, tungsten, tin, silver, titanium, nickel, zirconium, rhenium, bismuth, molybdenum, combinations thereof, and the like). More or fewer fluoroscopic markers are also possible.

In some methods of use, the filter system 900 may be advanced into the subject through an incision made in the subject's left radial artery, or alternatively the left brachial artery. The system 900 is advanced into the left subclavian artery 16. The device 900 may be positioned, deployed, and retrieved in a similar manner to that described with respect to device 200.

Figure 12A:
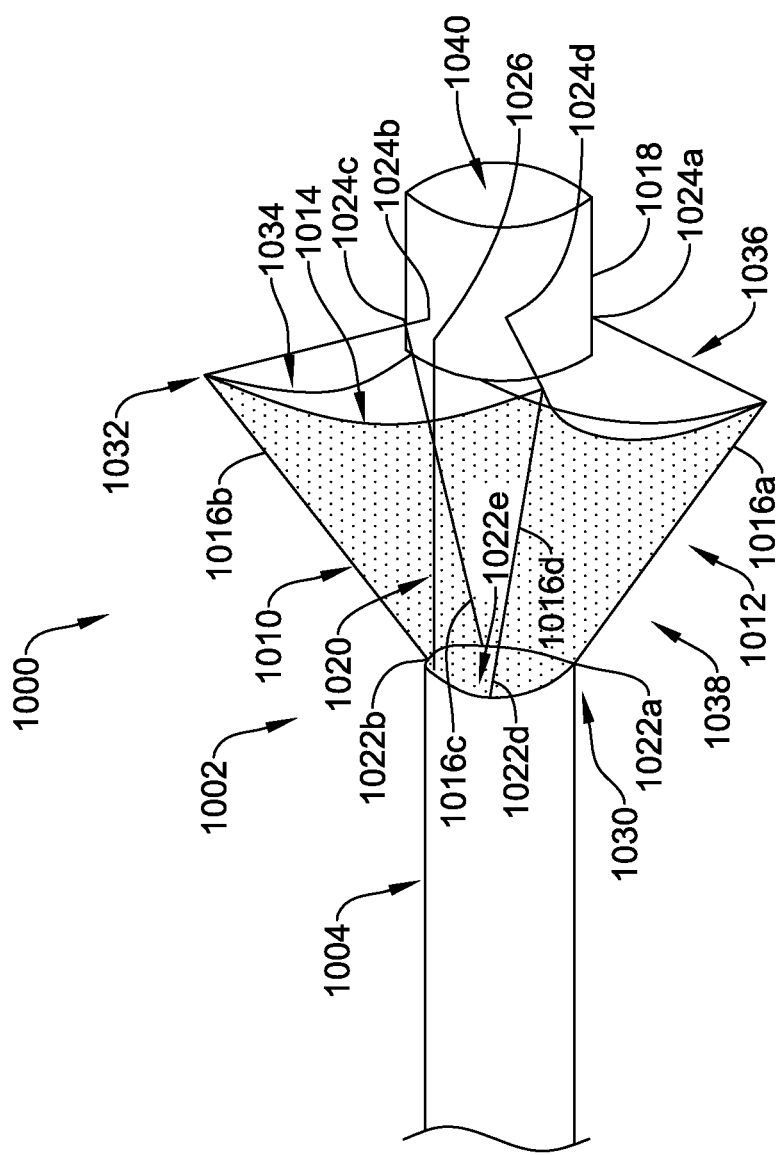
FIG. 12A illustrates another alternative embodiment of a protection device.

FIG. 12A illustrates a side view of another illustrative protection device 1000 in an expanded configuration. The protection device 1000 may be configured to be positioned in the left subclavian artery 16 and may be similar in form and function the protection device 200 described herein. In some cases, the protection device 1000 may be positioned in another vessel or lumen. In some embodiments, the protection device 1000 may be used in combination with other protection devices, such as, but not limited to the protection device 30 described herein.

The protection device 1000 comprises a proximal portion (not explicitly shown) and a distal portion 1002. The proximal portion is configured to be held and manipulated by a user such as a surgeon. In some cases, the proximal portion may be coupled to a handle configured to facilitate delivery and deployment of the device 1000. In some cases, the handle of the protection device 1000 may be similar in form and function to the handles 40, 106 described herein. The distal portion 1002 is configured to be positioned at a target location such as the left subclavian artery 16. When the distal portion 1002 is configured to be positioned at the left subclavian artery 16, the location may be upstream of the left vertebral artery 24 such that the blood is filtered prior to entering the left vertebral artery 24.

The protection device 1000 may include at least an outer sheath 1004, an angiographic catheter (not explicitly shown), and a filter assembly 1010 including a filter element 1014. The filter assembly 1010 may further include an expandable support structure 1012. The support structure 1012 may include a plurality of legs 1016a, 1016b, 1016c, 1016d (collectively, 1016), a distal ring 1018, and a pull wire 1020. A proximal end 1022a, 1022b, 1022c, 1022d (collectively, 1022) of each leg 1016 may be coupled to the distal end region 1030 of the outer sheath 1004 and a distal end 1024a, 1024b, 1024c, 1024d (collectively, 1024) of each leg 1016 may be coupled to the distal ring 1018. A distal end 1026 of the pull wire 1020 may also be coupled to the distal ring 1018. The proximal end of the pull wire 1020 may extend proximally through a lumen 1032 of the outer sheath 1004 to a point outside the body where the pull wire can be actuated by a user. The distal ring 1018 may be a generally tubular element configured to be axially displaced relative to the distal end region 1030 of the outer sheath 1004

The support structure 1012 may be similar in form and function to the end rings 124, 126 described herein. For example, the support structure 1012, or components thereof, may be formed from similar materials, wire shapes, sizes, etc., as the end rings 124, 126. In some embodiments, the filter assembly 1010 may be a stent supported filter, although this is not required. The filter element 1014 may be coupled to and extend between the plurality of legs 1016. The filter element 1014 may be similar in form and function to the filter element 128 described herein. For example, the filter element 1014 may be formed from a drilled or perforated membrane extending between the legs 1016. In some cases, the filter element 1014 may be formed from a woven or braided structure. In some embodiments, the filter element 1014 may be manually expanded through an actuation device. It is contemplated that other materials and configurations may be used for the filter element 1014 which allows the filter element 1014 to appose the vessel wall in the expanded configuration.

Figure 12B:
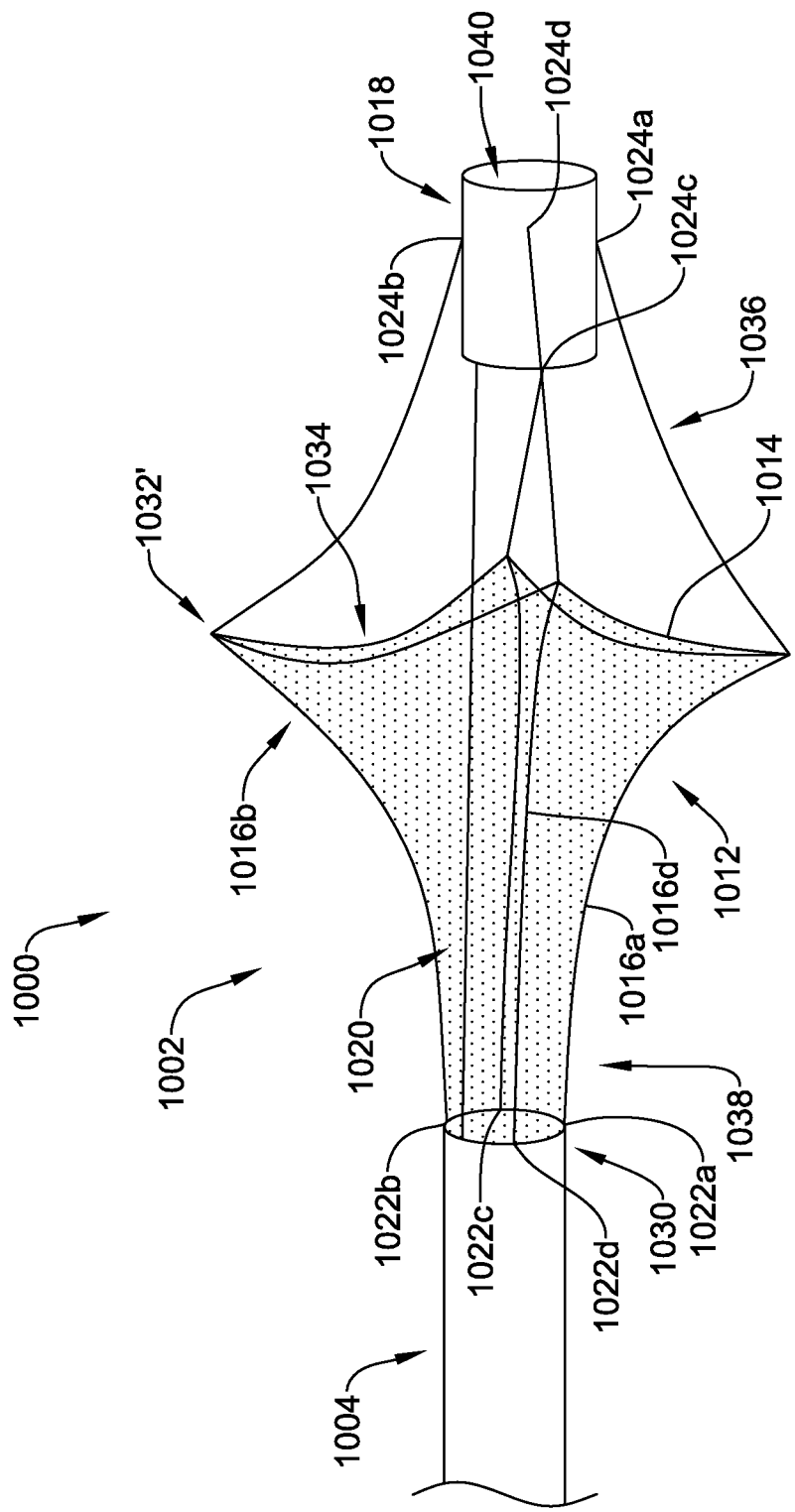
FIG. 12B illustrates another alternative embodiment of a protection device.
Figure 12C:
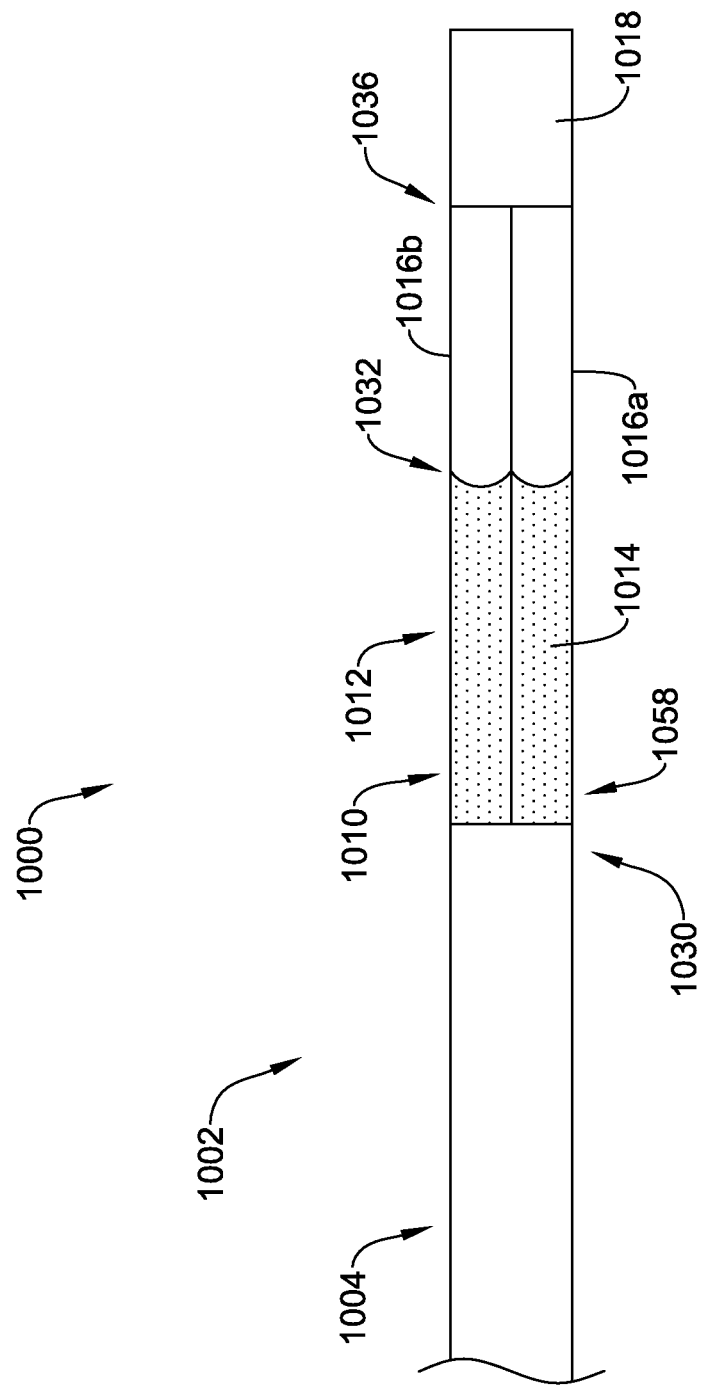
FIG. 12C illustrates the protection device of FIG. 12A in a collapsed configuration.

In a collapsed configuration, the filter assembly 1010 may extend generally in line with the outer sheath (see, for example, FIG. 12C, which illustrates the illustrative device 1000 in a collapsed or delivery configuration). Said differently, the filter assembly 1010 may extend distally from the distal end 1030 of the outer sheath 1004 in both the collapsed delivery configuration (FIG. 12C) and the expanded deployed configuration (FIG. 12A). To move the filter assembly 1010 from the collapsed delivery configuration (FIG. 12C) to the expanded deployed configuration (FIG. 12A), the pull wire 1020 is tensioned (e.g., proximally actuated). As the pull wire 1020 is pulled, the distance between the distal ring 1018 and the distal end 1030 of the outer sheath 1004 is reduced. As this distance is reduced, the legs 1016 are deflected or forced radially outwards, thus opening the filter element 1014. In some cases, the legs 1016 may be configured to bend at a predetermined position 1032. This may be achieved by mechanically deforming the legs 1016, using a shape memory material, etc. It is contemplated that the location of bend 1032 may be repositioned to vary a location of the distal opening 1034 of the filter element 1014 in the expanded configuration. For example, in FIG. 12A, the bend 1032 is more distally located whereas in FIG.

12B, the bend 1032' is more centrally located between the distal end 1030 of the outer sheath 1004 and the distal ring 1018. In both embodiments, as the filter assembly 1010 expands from the collapsed delivery configuration (FIG. 12C) to the expanded configuration (FIG. 12A or 12B), the bent portion 1032, 1032' expands to a greater diameter than the distal end region 1036 and/or the proximal end region 1038 of the filter assembly 1010.

To deploy the filter assembly 1010, the device 1000 is advanced through the vasculature to the desired location. The pull wire 1020 may be maintained in a distally advanced position to elongate the legs 1016 and maintain the filter assembly 1010 in the radially collapsed configuration during delivery. As described above, the pull wire 1020 may be proximally actuated to expand the filter assembly 1010. As the filter assembly 1010 is deployed, the support structure 1012 may open the filter element 1014 to the size of the vessel. To collapse the filter assembly 1010, the pull wire 1020 can be distally advanced to elongate the legs 1016.

When in the expanded configuration, the filter element 1014 is adapted to filter fluid, such as blood, and trap particles flowing therethrough. The filter element 1014 has pores therein that are sized to allow the blood to flow therethrough, but are small enough to prevent unwanted foreign particles from passing therethrough. The foreign particles are therefore trapped by and within the filter element 1014. As shown in FIGS. 12A and 12B, the filter assembly 1010 has a generally distally-facing opening 1034. In other embodiments, the opening 1034 may be proximally facing. The orientation of the opening 1034 may vary depending on where the access incision is located and/or the vessel in which it is deployed.

In some embodiments, the filter element 1014 forms an oblique truncated cone having a non-uniform or unequal length around and along the length of the filter assembly 1010. In such a configuration, along the lines of a windsock, the filter assembly 1010 has a larger opening 1034 (upstream) diameter and a reduced ending (downstream) diameter. The filter assembly 1010 may define a central lumen 1040 extending the length thereof (e.g., from the proximal end region 1038 and through the distal ring 1018) to allow an angiographic or pigtail catheter to pass through the lumen 1040. In some embodiments, the device 1000 may be advanced with the angiographic catheter within the lumen 1042 of the outer sheath 1004 and/or within the lumen 1040 of the filter assembly 1010 to provide support to the filter assembly 1010 during navigation, although this is not required. The lumen 1040 may include an open proximal end and an open distal end. It is contemplated that the open proximal end may be in fluid communication with the central lumen 1042 of the outer sheath 1004 or other tubular member to direct any captured debris away from the cerebral vasculature. In some cases, the open proximal end region 1038 of the filter assembly 1010 may be coupled to or within a distal portion of the outer sheath 1004.

The distal portion 1002 may include fluoroscopic markers to aid a user in positioning the device 1000, deploying the filter assembly 1010, utilizing the pigtail catheter, etc. A fluoroscopic marker (not explicitly shown) may be positioned proximate to a distal end of the outer sheath 1004. Another fluoroscopic marker (not explicitly shown) may be positioned proximate to a proximal end of the filter assembly 1010. In some cases, another fluoroscopic marker (not explicitly shown) may be proximate to a distal end of the filter assembly 1010. The fluoroscopic markers may comprise a radiopaque material (e.g., iridium, platinum, tantalum, gold, palladium, tungsten, tin, silver, titanium, nickel, zirconium, rhenium, bismuth, molybdenum, combinations thereof, and the like). More or fewer fluoroscopic markers are also possible.

In some methods of use, the filter system 1000 may be advanced into the subject through an incision made in the subject's left radial artery, or alternatively the left brachial artery. The system 1000 is advanced into the left subclavian artery 16. The device 1000 may be positioned, deployed, and retrieved in a similar manner to that described with respect to device 200.

Figure 13A:
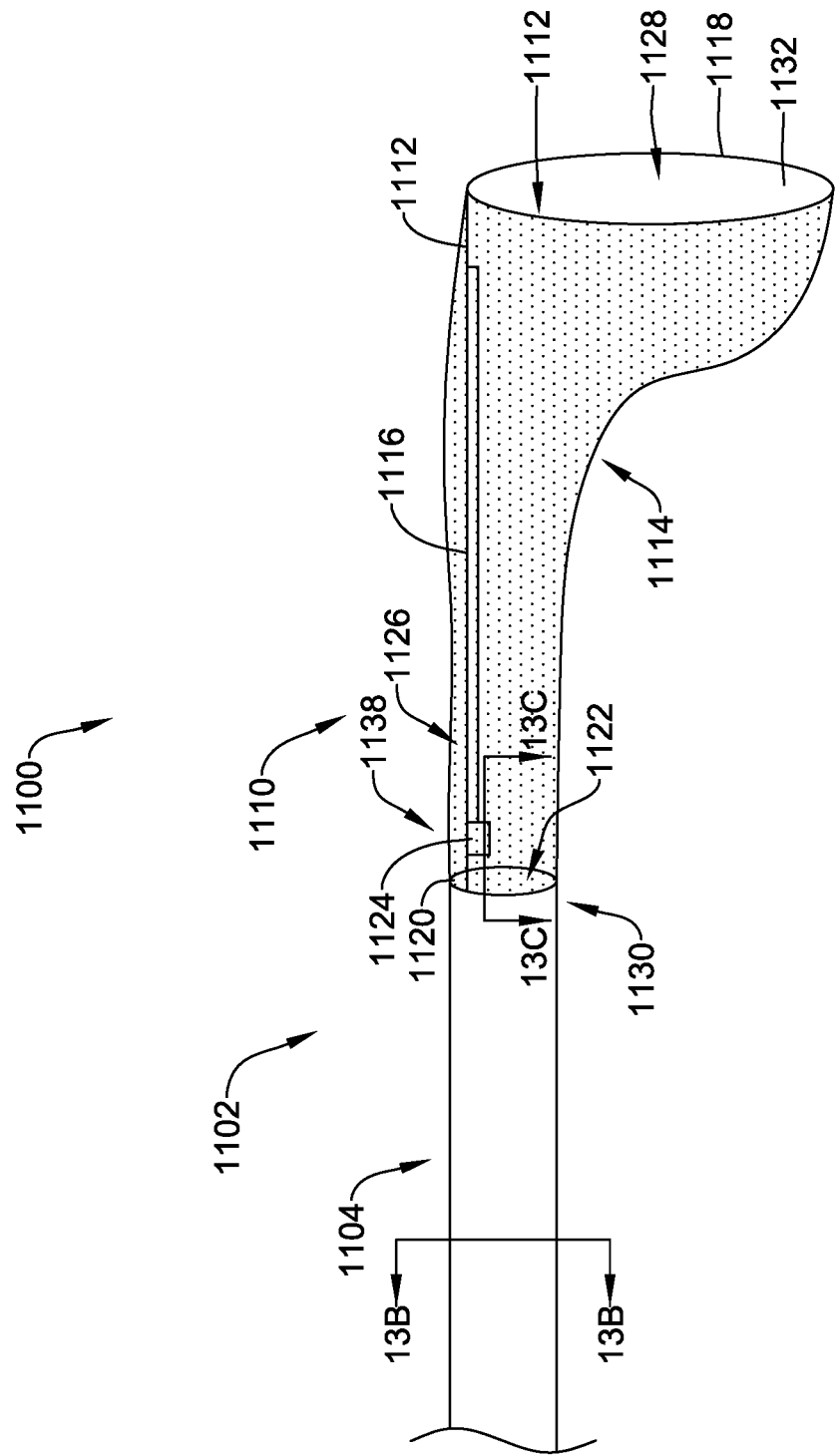
FIG. 13A illustrates another alternative embodiment of a protection device.

FIG. 13A illustrates a partial side view of another illustrative protection device 1100 in an expanded configuration. The protection device 1100 may be configured to be positioned in the left subclavian artery 16 and may be similar in form and function the protection device 200 described herein. In some cases, the protection device 1100 may be positioned in another vessel or lumen. In some embodiments, the protection device 1100 may be used in combination with other protection devices, such as, but not limited to the protection device 30 described herein.

The protection device 1100 comprises a proximal portion (not explicitly shown) and a distal portion 1102. The proximal portion is configured to be held and manipulated by a user such as a surgeon. In some cases, the proximal portion may be coupled to a handle configured to facilitate delivery and deployment of the device 1100. In some cases, the handle of the protection device 1100 may be similar in form and function to the handles 40, 106 described herein. The distal portion 1102 is configured to be positioned at a target location such as the left subclavian artery 16. When the distal portion 1102 is configured to be positioned at the left subclavian artery 16, the location may be upstream of the left vertebral artery 24 such that the blood is filtered prior to entering the left vertebral artery 24.

The protection device 1100 may include at least an outer sheath 1104, an angiographic catheter (not explicitly shown), and a filter assembly 1110 including a filter element 1114. The filter assembly 1110 may further include an expandable support structure or frame 1112. The support structure 1112 may include a longitudinally extending leg 1116 and a distal hoop 1118. The filter element 1114 may be mounted to a distal end region 1130 of the elongate shaft 1104 and supported by the support structure 1112. The support structure 1112 may be similar in form and function to the end rings 124, 126 described herein. For example, the support structure 1112, or components thereof, may be formed from similar materials, wire shapes, sizes, etc., as the end rings 124, 126. In some embodiments, the filter assembly 1110 may be a stent supported filter, although this is not required. The filter element 1114 may be coupled to the support structure. The filter element 1114 may be similar in form and function to the filter element 128 described herein. For example, the filter element 1114 may be formed from a drilled or perforated membrane extending across the support structure 1112. In some cases, the filter element 1114 may be formed from a woven or braided structure. In some embodiments, the filter element 1114 may be manually expanded through an actuation device. It is contemplated that other materials and configurations may be used for the filter element 1114 which allows the filter element 1114 to appose the vessel wall in the expanded configuration.

The filter assembly 1110 may further include a pull wire 1120. A distal end of the pull wire 1120 may be coupled to the support structure 1112. The pull wire 1120 extends proximally therefrom to a point outside the body where it can be manipulate by a user. The pull wire 1120 may be configured to retrieve the support structure 1112 into a lumen 1122 of the outer sheath 1104 and inverting the filter element 1114 until the filter assembly 1110 is fully contained within the lumen 1122 of the outer sheath 1104. It is contemplated that the pull wire 1120 may have a circular cross-section, a rectangular cross-section, or any other shape, as desired.

The filter assembly 1110 may further include a deployment piece, protection or member 1124 mounted onto or coupled to a proximal portion 1126 of the support structure 1112. The deployment piece 1124 may be configured to extend radially inward into a lumen 1128 of the filter assembly 1110 such that an angiographic catheter (or other inner shaft) may exert a distal force on the deployment piece when the filter assembly 1110 is in the radially collapsed delivery configuration within the lumen 1122 of the outer sheath 1104. In the fully collapsed configuration, the cross-sectional or radial dimension of the deployment piece 1124 may be sized such that it extend far enough into the lumen 1128 to be engaged by the angiographic catheter or pusher element. This may allow the angiographic catheter or pusher element to push against the deployment piece 1124 to facilitate deployment of the filter assembly 1110. For example, as the catheter or pusher element is through a lumen 1122 of the outer sheath 1104, the catheter or pusher element abuts the deployment piece 1124 and pushes the deployment piece 1124 out of the distal end region 1130 of the outer sheath 1104 where it expands to seal against the lumen. It is contemplated that as the filter assembly 1110 expands, the deployment piece 1124 is moved radially outwards to allow for passage of the angiographic catheter (or other member) through the filter assembly 1110. In some embodiments, the longitudinally extending leg 1116 and/or the distal hoop 1118 may be angled to help with or facilitate apposition within the vessel.

To deploy the filter assembly 1110, the device 1100 is advanced through the vasculature to the desired location. As described above, the angiographic catheter may be distally advanced to expand the filter assembly 1110. As the filter assembly 1110 is deployed, the support structure 1112 may open the filter element 1114 to the size of the vessel. To collapse the filter assembly 1110, the pull wire 1120 can be proximally retracted to draw the filter assembly 1110 into the lumen 1122 of the elongate sheath 1104.

Figure 13B:
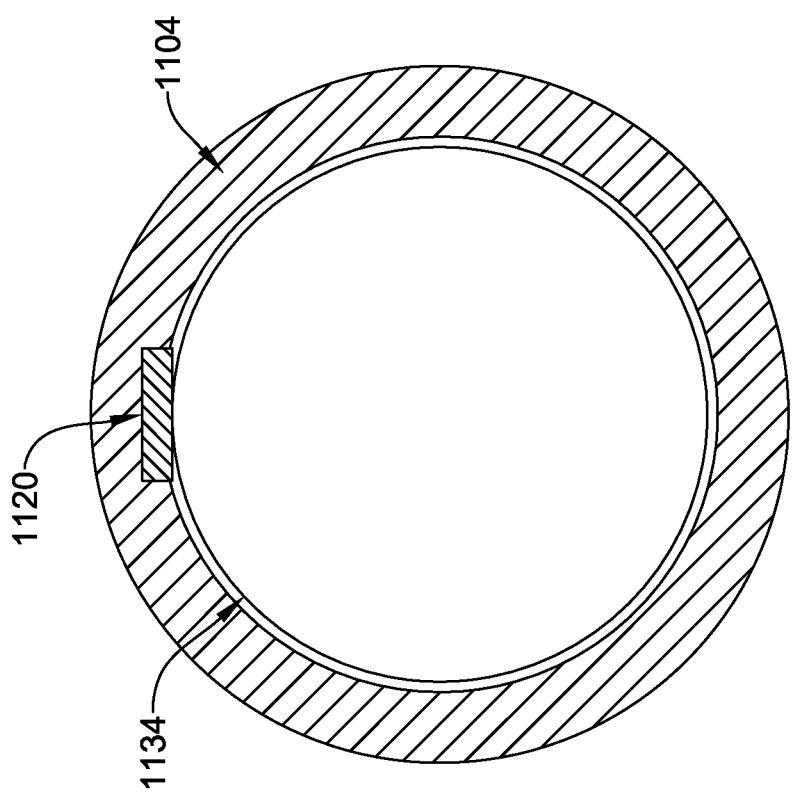
FIG. 13B is a cross-sectional view of the protection device of FIG. 13A taken at line 13B-13B.
Figure 13C:
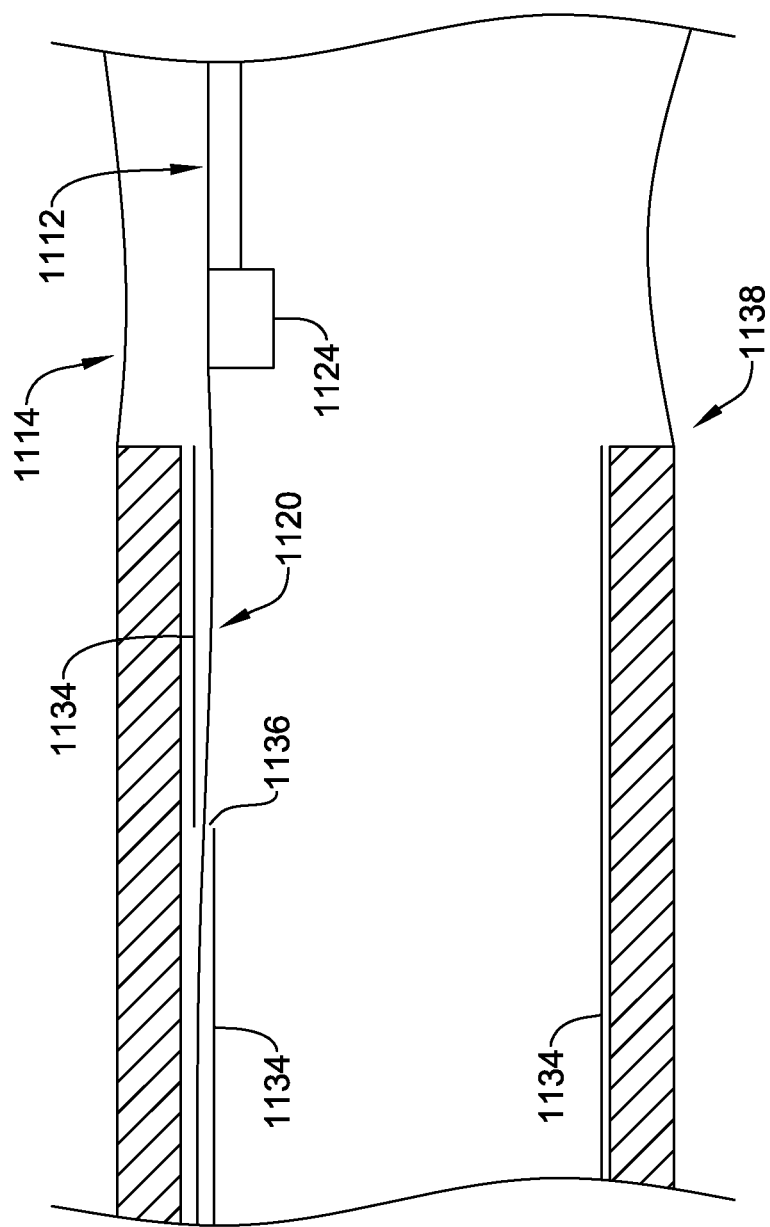
FIG. 13C is a cross-sectional view of the protection device of FIG. 13A taken at line 13C-13C.

In some embodiments, the pull wire 1120 may utilized a profiled or keyed geometry to limit rotation of the filter assembly 1110 once deployed. Referring additionally to FIG. 13B which illustrates a cross-sectional view of the protection device taken at line 13B-13B in FIG. 13A and FIG. 13C which illustrates a partial cross-sectional view of the protection device taken at line 13C-13C in FIG. 13A, a proximal portion of the pull wire 1120 may be disposed between the outer sheath 1104 and an inner liner 1134. The inner liner 1134 may be formed form a lubricious material, such as, but not limited polytetrafluoroethene (e.g., TEFLON®), to reduce the required forces for deployment and resheathing of the filter assembly 1110. The liner 1134 may be a generally tubular component and may include an opening or aperture 1136 configured to allow the pull wire to exit the space between the liner 1134 and the outer sheath 1104. The opening 1136 may be sized to limit rotational and/or radial movement of the pull wire 1120

When in the expanded configuration, the filter element 1114 is adapted to filter fluid, such as blood, and trap particles flowing therethrough. The filter element 1114 has pores therein that are sized to allow the blood to flow therethrough, but are small enough to prevent unwanted foreign particles from passing therethrough. The foreign particles are therefore trapped by and within the filter element 1114. As shown in FIG. 13A, the filter assembly 1110 has a generally distally-facing opening 1132. In other embodiments, the opening 1132 may be proximally facing. The orientation of the opening 1132 may vary depending on where the access incision is located and/or the vessel in which it is deployed.

In some embodiments, the filter element 1114 forms an oblique truncated cone having a non-uniform or unequal length around and along the length of the filter assembly 1110. In such a configuration, along the lines of a windsock, the filter assembly 1110 has a larger opening 1132 (upstream) diameter and a reduced ending (downstream) diameter. The filter assembly 1110 may define a central lumen 1128 extending the length to allow an angiographic or pigtail catheter to pass through the lumen 1128. The lumen 1128 may include an open proximal end and an open distal end. It is contemplated that the open proximal end may be in fluid communication with the central lumen 1122 of the outer sheath 1104 or other tubular member to direct any captured debris away from the cerebral vasculature. In some cases, the open proximal end region 1138 of the filter assembly 1110 may be coupled to or within a distal portion of the outer sheath 1104.

The distal portion 1102 may include fluoroscopic markers to aid a user in positioning the device 1100, deploying the filter assembly 1110, utilizing the pigtail catheter, etc. A fluoroscopic marker (not explicitly shown) may be positioned proximate to a distal end of the outer sheath 1104. Another fluoroscopic marker (not explicitly shown) may be positioned proximate to a proximal end of the filter assembly 1110. In some cases, another fluoroscopic marker (not explicitly shown) may be proximate to a distal end of the filter assembly 1110. The fluoroscopic markers may comprise a radiopaque material (e.g., iridium, platinum, tantalum, gold, palladium, tungsten, tin, silver, titanium, nickel, zirconium, rhenium, bismuth, molybdenum, combinations thereof, and the like). More or fewer fluoroscopic markers are also possible.

In some methods of use, the filter system 1100 may be advanced into the subject through an incision made in the subject's left radial artery, or alternatively the left brachial artery. The system 1100 is advanced into the left subclavian artery 16. The device 1100 may be positioned, deployed, and retrieved in a similar manner to that described with respect to device 200.

Figure 14:
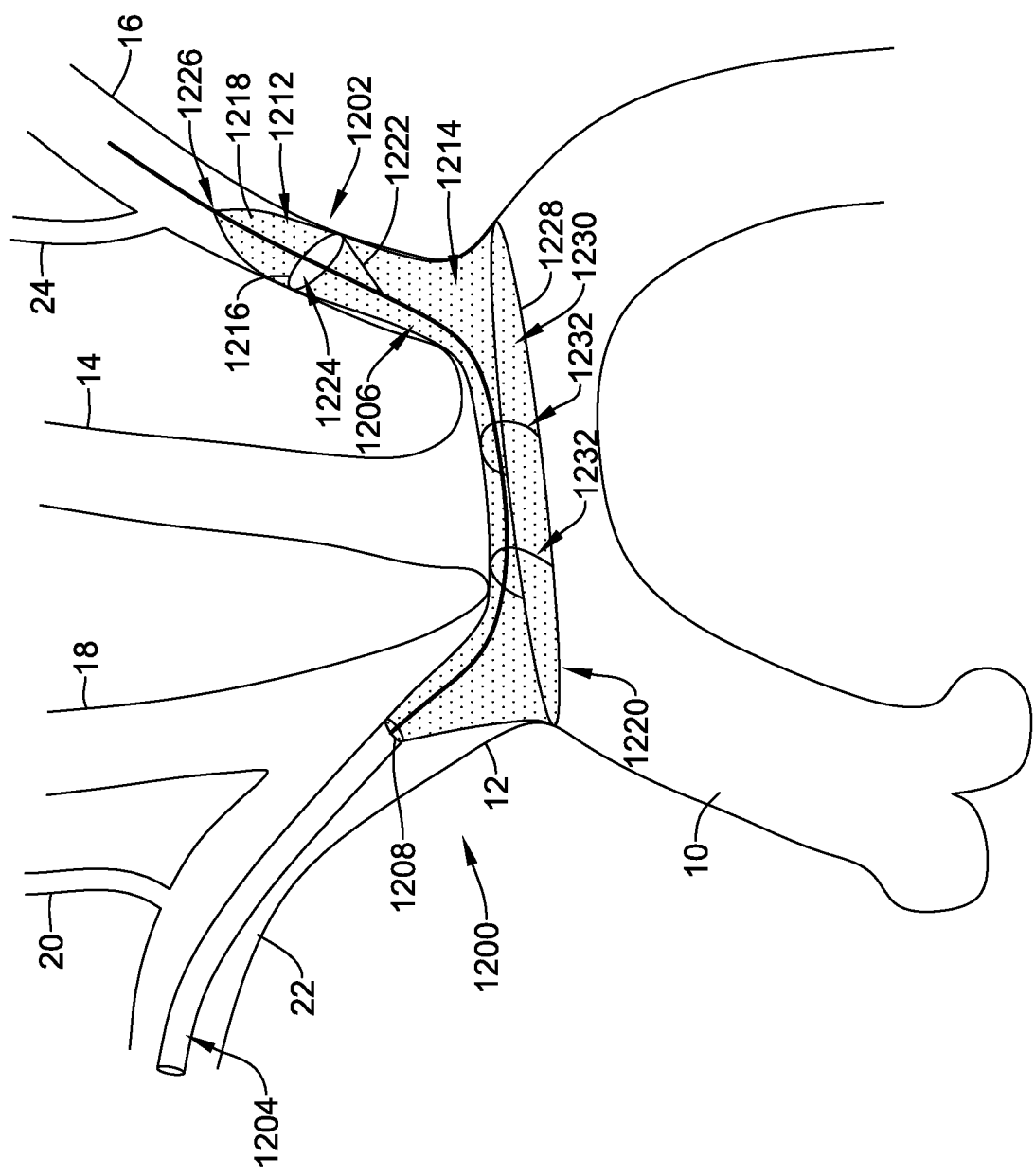
FIG. 14 illustrates another alternative embodiment of a protection device.

FIG. 14 illustrates a schematic view of another illustrative protection device 1200 in an expanded configuration within the aortic arch. The protection device 1200 may be configured to be introduced through the brachiocephalic or innominate artery 12 via the right radial or right brachial artery, and across the aortic arch 10. Generally, a distal portion 1202 of the catheter is anchored in the left subclavian artery 16, and a membrane or filter element 1214 is deployed such that the protection device 1200 isolates all three of the left subclavian, left common carotid and brachiocephalic arteries 16, 14, 12 from embolic debris that might flow through the aortic arch 10. It is contemplated that features of the protection device 1200 described herein can be differently combined to form additional embodiments. All embodiments shown may also be introduced into the left radial or brachial artery, with the distal portion of the catheter anchored in the brachiocephalic artery 12.

The protection device 1200 comprises a proximal portion (not explicitly shown) and a distal portion 1202. The proximal portion is configured to be held and manipulated by a user such as a surgeon. In some cases, the proximal portion may be coupled to a handle configured to facilitate delivery and deployment of the device 1200. In some cases, the handle of the protection device 1200 may be similar in form and function to the handles 40, 106 described herein. The distal portion 1202 is configured to be positioned at a target location such as the left subclavian artery 16. When the distal portion 1202 is configured to be positioned at the left subclavian artery 16, the location may be upstream of the left vertebral artery 24 such that the blood is filtered prior to entering the left vertebral artery 24, although this is not required.

Generally, the protection system 1200 may include an outer sheath 1204, an inner member 1206, a distal filter assembly 1212, and a proximal filter assembly 1220. The inner member 1206 and the outer sheath 1204 may be configured to extend from the proximal end region to the distal end region 1202 of the protection device 1200. The outer sheath 1204 and the inner member 1206 may be guided over a guidewire (not explicitly shown), or along the guidewire (in a rapid exchange configuration) to position a distal end of the outer sheath 1204 within the left subclavian artery 16. The inner member 1206 may be radially inward of the outer sheath 1204 and separately actuatable therefrom (e.g., slidably disposed within a lumen of the outer sheath 1204).

To position the protection device 1200 within the body, an incision may be made in the subject's right radial artery, or alternatively the right brachial artery. An introducer (not explicitly shown) may be placed into the incision and the protection device 1200 inserted into the introducer. The filter protection device 1200 may be advanced through the vasculature in a delivery configuration in which the distal filter assembly 1212 and the proximal filter assembly 1220 are collapsed or sheathed within the outer sheath 1204. The outer sheath 1204, inner member 1206, and the filter assemblies 1212, 1220 may be advanced over a guidewire (if so provided) to the target location. In some cases, the guidewire may be positioned at the target location and the outer sheath 1204, inner member 1206, and the filter assemblies 1212, 1220 subsequently advanced over the guidewire to the target location. In other instances, the guidewire and the outer sheath 1204, inner member 1206, and the filter assemblies 1212, 1220 may be advanced substantially simultaneously with the guidewire leading (e.g., positioned most distal to) the outer sheath 1204, inner member 1206, and the filter assemblies 1212, 1220.

The delivery catheter or outer sheath 1204 may have a diameter sized to navigate the vasculature from the incision to the target location. An outer sheath 1204 sized for right radial access may have a diameter in the range of about 6 French (F). An outer sheath 1204 sized for femoral access may be larger, although this is not required. These are just some examples. In some cases, the outer sheath 1204 (or other components of the protection device 1200) may include deflectable tip or an articulatable distal tip. It is contemplated that the distal tip of the outer sheath 1204 may be deflected (e.g., using a handle) to facilitate navigation of the device 1200 through the vasculature and cannulation of the target vessel. In some cases, the deflectable tip may be configured to deflect by about 90°. However, the tip of the outer sheath 1204 may be made to deflect by less than 90 or more than 90, as desired. The deflection may be controlled by a rotating knob at the handle, or the control mechanism. In some cases, the outer sheath 1204 may include a pre-shaped and/or non-deflectable tip.

The left subclavian artery 16 may be cannulated through a combination of advancing and torqueing the catheter 1204. In some cases, the left subclavian artery 16 may first be cannulated using the guidewire. It is contemplated that in some cases, the deflection of the catheter tip may be relaxed to advance the outer sheath 1204 into the left subclavian artery 16. Once the protection device 1200 (e.g., the distal end 1208 of the outer sheath 1204) has been advanced to the target location, which in the illustrated embodiment may be the left subclavian artery 16, the outer sheath 1204 may be proximally retracted to expose a distal filter assembly 1212 beyond the distal end 1208 of the outer sheath 1204. Alternatively, or additionally, the inner member 1206 may be distally advanced to deploy the distal filter assembly 1212. The distal filter assembly 1212 may be configured to be deployed in the distal-most great vessel relative to the location of the incision. For example, when right radial access is used, the distal-most great vessel is the left subclavian artery 16. However, if left radial access is used, the distal-most great vessel is the innominate artery 12.

The distal filter assembly 1212 may comprise a self-expanding filter assembly (e.g., comprising a superelastic material with stress-induced martensite due to confinement in the outer sheath 1204). The distal filter assembly 1212 may comprise a shape-memory material configured to self-expand upon a temperature change (e.g., heating to body temperature). The distal filter assembly 1212 may comprise a shape-memory or superelastic frame 1216 (e.g., comprising a nitinol hoop) and a microporous filter element 1218 (e.g., comprising a polymer including laser-drilled holes) coupled to the frame, for example similar to the filter assemblies described in U.S. Pat. No. 8,876,796.

The frame 1216 may generally provide expansion support to the filter element 1218 in the expanded state. In the expanded state, the filter element 1218 is configured to filter fluid (e.g., blood) flowing through the filter element 1218 and to inhibit or prevent particles (e.g., embolic material) from flowing through the filter element 1218 by capturing the particles in the filter element 1218. The frame 1216 may configured to anchor the distal filter assembly 1212 by engaging or apposing the inner walls of a lumen (e.g., blood vessel) in which the distal filter assembly 1212 is expanded. In some cases, the distal filter assembly 1212 may also anchor the proximal filter assembly 1220. For example, the distal filter assembly 1212 may be a distal anchoring mechanism. The anchoring mechanism may include a filter membrane or may lack a filter membrane, as desired. Other anchoring mechanisms may be provided in addition to or alternatively to the distal filter assembly 1212. The frame 1216 may be similar in form and function to the end rings 124, 126 described herein. For example, the frame 1216 may be formed from similar materials, wire shapes, sizes, etc., as the end rings 124, 126. Similarly, the filter element 1218 may be similar in form and function to the filter element 128 described herein. The frame 1216 may be coupled to a support strut 1222. The frame 1216 may form a shape of an opening 1224 of the distal filter assembly 1212. The opening 1224 may be circular, elliptical, or any shape that can appropriately appose sidewalls of a vessel such as the left subclavian artery 16. The distal filter assembly 1212 may have a generally proximally-facing opening 1224. In other embodiments, the opening 1224 may be distally facing. For example, the orientation of the opening 1224 may vary depending on where the access incision is located.

The frame 1216 may include a radiopaque marker such as a small coil wrapped around or coupled to the hoop to aid in visualization under fluoroscopy. In some embodiments, the frame 1216 may comprise a shape other than a hoop, for example, a spiral. In some embodiments, the distal filter assembly 1212 may not include or be substantially free of a frame.

In some embodiments, the frame 1216 and the filter element 1218 form an oblique truncated cone having a non-uniform or unequal length around and along the length of the distal filter assembly 1212. In such a configuration (e.g., along the lines of a windsock), the filter assembly 1212 has a larger opening 1224 (upstream) diameter and a reduced ending (downstream) diameter.

The distal filter assembly 1212 may be coupled (e.g., crimped, welded, soldered, etc.) to a distal end of a deployment wire or filter wire (not explicitly shown) and/or the inner member 1206 via a strut or wire 1222, although this is not required. When both or all of the filter wire and the strut 1222 are provided, the filter wire and the strut 1222 may be coupled to the inner member 1206 proximal to the filter assembly 1212 using a crimp mechanism. In other embodiments, the filter wire and the strut 1222 may be a single unitary structure. The filter wire and/or strut 1222 can comprise a rectangular ribbon, a round (e.g., circular, elliptical) filament, a portion of a hypotube, a braided structure, combinations thereof, and the like. A distal filter bag termination 1226 or a distal end 1226 of the distal filter assembly may also be coupled to the inner member 1206. In some cases, the distal end 1226 may be coupled to the inner member using a nose cone. The nose cone may both secure the distal end 1226 of the distal filter assembly 1212 and reduce injury and/or vessel perforation during insertion of the device 1200. In some cases, the inner member 1206 may reduce in diameter in the distal direction. The diameter may be step-wise or gradual.

The distal filter assembly 1212 in an expanded, unconstrained state may have a maximum diameter or effective diameter (e.g., if the mouth is in the shape of an ellipse the effective diameter is the diameter of the approximate circular opening 1224 of the filter viewed from an end view) The diameter can be between about 1 mm and about 15 mm (e.g., at least about 2 mm, about 4 mm, about 6 mm, about 8 mm, about 10 mm or more, but generally less than about 15 mm or 12 mm or less depending upon the intended target vessel. In some embodiments (e.g., when the distal filter assembly 1212 is configured to be positioned in the left subclavian artery 16), the diameter may be between about 7 mm and about 12 mm (e.g., about 7 mm, about 8 mm, about 9 mm, about 10 mm, about 11 mm, about 12 mm, ranges between such values, etc.). In some embodiments (e.g., when the distal filter assembly 1212 is configured to be positioned in the left vertebral artery 24), the diameter may be between about 2 mm and about 4.5 mm (e.g., about 2 mm, about 2.5 mm, about 3 mm, about 3.5 mm, about 4 mm, about 4.5 mm, ranges between such values, etc.). Other diameters or other types of lateral dimensions are also possible. Different diameters can allow treatment of a selection of subjects having different vessel sizes.

The filter assembly 1212 may have a maximum length from a proximal limit of the frame 1216 to the distal end or point of convergence 1226 with the inner member 1206. The length can be between about 7 mm and about 50 mm (e.g., at least about 7 mm, about 8 mm, about 10 mm, about 12 mm, 16 mm, about 20 mm or more, but generally less than about 40 mm or 30 mm or 20 mm or less depending upon the intended target vessel. Other lengths are also possible, for example based on the diameter or effective diameter. For example, the length of the distal filter assembly 1212 may increase as the diameter increases, and the length of the distal filter assembly 1212 may decrease as the diameter decreases.

In the illustrated embodiment, the distal filter assembly 1212 comprises a self-expanding support such as hoop or frame 1216 which supports the open proximal end of an approximately conical filter membrane 1218. A support strut 1222 may be provided to connect the frame 1216 to a portion of the device 1200 such as the inner member 1206, to facilitate resheathing of the filter assembly 1212 and also to orientate the hoop or frame 1216. In the illustrated embodiment, the distal filter assembly 1212 may function both to filter blood entering the left subclavian artery 16, and also to anchor the system.

Continued proximal actuation of the outer sheath 1204 while fixing the inner member 1206 relative to the handle may then deploy the aortic arch component or proximal filter assembly 1220, as shown in FIG. 14. It is contemplated that distal end 1208 of the outer sheath 1204 may be withdrawn into the innominate artery 12 or the right subclavian artery 22 to fully expose the proximal filter assembly 1220. As the outer sheath 1204 is withdrawn, the distal filter assembly 1212 remains in the left subclavian artery 16, supported by the inner member 1206 and helping to anchor the proximal filter assembly 1220.

The proximal filter assembly 1220 may include an aortic ring 1228 or support element and a filter membrane or filter element 1214. The aortic ring 1228 may be similar in form and function to the frame 1216 of the distal filter assembly 1212, although larger in scale. Similarly, the filter element 1214 may be similar in form and function to the filter element 128 described herein. The aortic ring 1228 generally provides expansion support to the filter element 1214 in its expanded configuration, while the filter element 1214 is adapted to filter fluid, such as blood, and trap particles flowing therethrough. The aortic ring 1228 may include an approximately elliptical hoop of a shape memory wire such as nitinol. The aortic ring 1228 may be configured to engage the wall of the aorta and seal against the roof of the aortic arch 10 outside of the ostia of all three great vessels 12, 14, 16 to isolate the cerebral vasculature. For example, the aortic ring 1228 may be sized and shaped such that it extends from the ostium of the left subclavian artery 16 to the ostium of the innominate artery 12. The center 1230 of the aortic ring 1228 is open to allow blood and debris to enter the device 1220, and the ring 1228 is attached around its perimeter to the filter element 1214. A proximal end of the filter element 1214 may be coupled to or extend into a distal end 1208 of the outer sheath 1204. The aortic ring 1228 may be self-expanding such that as the outer sheath 1204 is proximally withdrawn, the aortic ring 1228 automatically expands, although this is not required. The aortic ring 1228 may be coupled to different portions of the protection device 1200. In some embodiments, the aortic ring 1228 may further include one or more structural elements 1232 extending across the filter element 1214. The structural element 1232 may help to improve apposition and increase the overall stability of the filter element 1214.

Once the proximal filter assembly 1220 has been deployed, the inner member 1206 may be retracted to minimize intrusion into the aorta 10. The position of the inner member 1206 may be adjusted using a control at the handle. The mechanism coupling the proximal filter 1220 to the device 1200 may be adjusted by proximally retracting or distally advancing the handle to ensure the proximal filter 1220 is fully deployed, the aortic ring 1228 is apposed to the roof of the aortic arch 10, and the inner member 1206 is pulled up against the roof of the aortic arch 10 to ensure that the filter element 1214 is fully against the roof of the arch 10. The proximal filter assembly 1220 is thus positioned to protect the cerebral vasculature 14, 18, 20, 24 from embolic debris during an endovascular procedure such as TAVR.

Once the protection device 1200 has been deployed, the TAVR, or other index procedure, may be performed. Once the index procedure is contemplate, the inner member 1206 may be advanced relative to the handle to apply tension to the proximal filter element 1214 and/or the distal filter element 1218. The outer sheath 1204 may then be advanced relative to the handle, while fixing the position of the inner member 1206 relative to the handle, until the proximal filter assembly 1220 and the distal filter assembly 1212 are fully sheathed. The protection device 1200 may then be removed from the introducer sheath.

Figure 15:
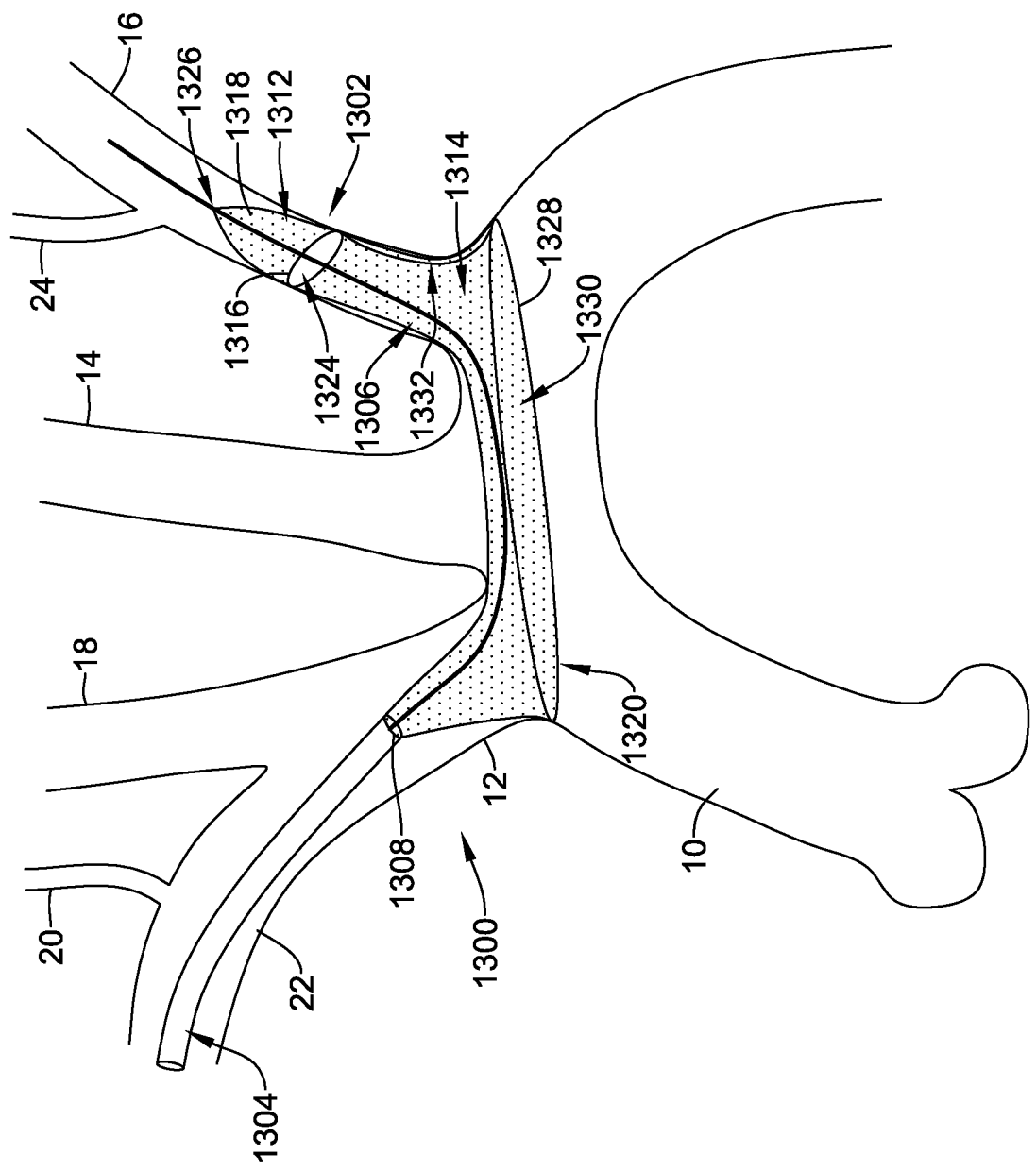
FIG. 15 illustrates another alternative embodiment of a protection device.

FIG. 15 illustrates a schematic view of another illustrative protection device 1300 in an expanded configuration within the aortic arch 10. The protection device 1300 may be configured to be introduced through the brachiocephalic or innominate artery 12 via the right radial or right brachial artery, and across the aortic arch 10. Generally, a distal portion 1302 of the catheter is anchored in the left subclavian artery 16, and a membrane or filter element 1314 is deployed such that the protection device 1300 isolates all three of the left subclavian, left common carotid and brachiocephalic arteries 16, 14, 12 from embolic debris that might flow through the aortic arch 10. It is contemplated that features of the protection device 1300 described herein can be differently combined to form additional embodiments. All embodiments shown may also be introduced into the left radial or brachial artery, with the distal portion of the catheter anchored in the brachiocephalic artery 12.

The protection device 1300 comprises a proximal portion (not explicitly shown) and a distal portion 1302. The proximal portion is configured to be held and manipulated by a user such as a surgeon. In some cases, the proximal portion may be coupled to a handle configured to facilitate delivery and deployment of the device 1300. In some cases, the handle of the protection device 1300 may be similar in form and function to the handles 40, 106 described herein. The distal portion 1302 is configured to be positioned at a target location such as the left subclavian artery 16. When the distal portion 1302 is configured to be positioned at the left subclavian artery 16, the location may be upstream of the left vertebral artery 24 such that the blood is filtered prior to entering the left vertebral artery 24, although this is not required.

Generally, the protection system 1300 may include an outer sheath 1304, an inner member 1306, a distal filter assembly 1312, and a proximal filter assembly 1320. The inner member 1306 and the outer sheath 1304 may be configured to extend from the proximal end region to the distal end region 1302 of the protection device 1300. The outer sheath 1304 and the inner member 1306 may be guided over a guidewire (not explicitly shown), or along the guidewire (in a rapid exchange configuration) to position a distal end of the outer sheath 1304 within the left subclavian artery 16. The inner member 1306 may be radially inward of the outer sheath 1304 and separately actuatable therefrom (e.g., slidably disposed within a lumen of the outer sheath 1304).

To position the protection device 1300 within the body, an incision may be made in the subject's right radial artery, or alternatively the right brachial artery. An introducer (not explicitly shown) may be placed into the incision and the protection device 1300 inserted into the introducer. The protection device 1300 may be advanced through the vasculature in a delivery configuration in which the distal filter assembly 1312 and the proximal filter assembly 1320 are collapsed or sheathed within the outer sheath 1304. The outer sheath 1304, inner member 1306, and the filter assemblies 1312, 1320 may be advanced over a guidewire (if so provided) to the target location. In some cases, the guidewire may be positioned at the target location and the outer sheath 1304, inner member 1306, and the filter assemblies 1312, 1320 subsequently advanced over the guidewire to the target location. In other instances, the guidewire and the outer sheath 1304, inner member 1306, and the filter assemblies 1312, 1320 may be advanced substantially simultaneously with the guidewire leading (e.g., positioned most distal to) the outer sheath 1304, inner member 1306, and the filter assemblies 1312, 1320.

The delivery catheter or outer sheath 1304 may have a diameter sized to navigate the vasculature from the incision to the target location. An outer sheath 1304 sized for right radial access may have a diameter in the range of about 6 French (F). An outer sheath 1304 sized for femoral access may be larger, although this is not required. These are just some examples. In some cases, the outer sheath 1304 (or other components of the protection device 1300) may include deflectable tip or an articulatable distal tip. It is contemplated that the distal tip of the outer sheath 1304 may be deflected (e.g., using a handle) to facilitate navigation of the device 1300 through the vasculature and cannulation of the target vessel. In some cases, the deflectable tip may be configured to deflect by about 90°. However, the tip of the outer sheath 1304 may be made to deflect by less than 90 or more than 90, as desired. The deflection may be controlled by a rotating knob at the handle, or the control mechanism. In some cases, the outer sheath 1304 may include a pre-shaped and/or non-deflectable tip.

The left subclavian artery 16 may be cannulated through a combination of advancing and torqueing the catheter 1304. In some cases, the left subclavian artery 16 may first be cannulated using the guidewire. It is contemplated that in some cases, the deflection of the catheter tip may be relaxed to advance the outer sheath 1304 into the left subclavian artery 16. Once the protection device 1300 (e.g., the distal end 1308 of the outer sheath 1304) has been advanced to the target location, which in the illustrated embodiment may be the left subclavian artery 16, the outer sheath 1304 may be proximally retracted to expose a distal filter assembly 1312 beyond the distal end 1308 of the outer sheath 1304. Alternatively, or additionally, the inner member 1306 may be distally advanced to deploy the distal filter assembly 1312. The distal filter assembly 1312 may be configured to be deployed in the distal-most great vessel relative to the location of the incision. For example, when right radial access is used, the distal-most great vessel is the left subclavian artery 16. However, if left radial access is used, the distal-most great vessel is the innominate artery 12.

The distal filter assembly 1312 may comprise a self-expanding filter assembly (e.g., comprising a superelastic material with stress-induced martensite due to confinement in the outer sheath 1304). The distal filter assembly 1312 may comprise a shape-memory material configured to self-expand upon a temperature change (e.g., heating to body temperature). The distal filter assembly 1312 may comprise a shape-memory or superelastic frame 1316 (e.g., comprising a nitinol hoop) and a microporous filter element 1318 (e.g., comprising a polymer including laser-drilled holes) coupled to the frame, for example similar to the filter assemblies described in U.S. Pat. No. 8,876,796.

The frame 1316 may generally provide expansion support to the filter element 1318 in the expanded state. In the expanded state, the filter element 1318 is configured to filter fluid (e.g., blood) flowing through the filter element 1318 and to inhibit or prevent particles (e.g., embolic material) from flowing through the filter element 1318 by capturing the particles in the filter element 1318. The frame 1316 may configured to anchor the distal filter assembly 1312 by engaging or apposing the inner walls of a lumen (e.g., blood vessel) in which the distal filter assembly 1312 is expanded. In some cases, the distal filter assembly 1312 may also anchor the proximal filter assembly 1320. For example, the distal filter assembly 1312 may be a distal anchoring mechanism. The anchoring mechanism may include a filter membrane or may lack a filter membrane, as desired. Other anchoring mechanisms may be provided in addition to or alternatively to the distal filter assembly 1312. The frame 1316 may be similar in form and function to the end rings 124, 126 described herein. For example, the frame 1316 may be formed from similar materials, wire shapes, sizes, etc., as the end rings 124, 126. Similarly, the filter element 1318 may be similar in form and function to the filter element 128 described herein. The frame 1316 may form a shape of an opening 1324 of the distal filter assembly 1312. The opening 1324 may be circular, elliptical, or any shape that can appropriately appose sidewalls of a vessel such as the left subclavian artery 16. The distal filter assembly 1312 may have a generally proximally-facing opening 1324. In other embodiments, the opening 1324 may be distally facing. For example, the orientation of the opening 1324 may vary depending on where the access incision is located.

The frame 1316 may include a radiopaque marker such as a small coil wrapped around or coupled to the hoop to aid in visualization under fluoroscopy. In some embodiments, the frame 1316 may comprise a shape other than a hoop, for example, a spiral. In some embodiments, the distal filter assembly 1312 may not include or be substantially free of a frame.

In some embodiments, the frame 1316 and the filter element 1318 form an oblique truncated cone having a non-uniform or unequal length around and along the length of the distal filter assembly 1312. In such a configuration (e.g., along the lines of a windsock), the filter assembly 1312 has a larger opening 1324 (upstream) diameter and a reduced ending (downstream) diameter.

The distal filter assembly 1312 may be coupled (e.g., crimped, welded, soldered, etc.) to a distal end of a deployment wire or filter wire (not explicitly shown) and/or the inner member 1306 via a strut or wire, although this is not required. When both or all of the filter wire and the strut are provided, the filter wire and the strut may be coupled to the inner member 1306 proximal to the filter assembly 1312 using a crimp mechanism. In other embodiments, the filter wire and the strut may be a single unitary structure. The filter wire and/or strut can comprise a rectangular ribbon, a round (e.g., circular, elliptical) filament, a portion of a hypotube, a braided structure, combinations thereof, and the like. A distal filter bag termination 1326 or a distal end 1326 of the distal filter assembly may also be coupled to the inner member 1306. In some cases, the distal end 1326 may be coupled to the inner member using a nose cone. The nose cone may both secure the distal end 1326 of the distal filter assembly 1312 and reduce injury and/or vessel perforation during insertion of the device 1300. In some cases, the inner member 1306 may reduce in diameter in the distal direction. The diameter may be step-wise or gradual.

The distal filter assembly 1312 in an expanded, unconstrained state may have a maximum diameter or effective diameter (e.g., if the mouth is in the shape of an ellipse the effective diameter is the diameter of the approximate circular opening 1324 of the filter viewed from an end view) The diameter can be between about 1 mm and about 15 mm (e.g., at least about 2 mm, about 4 mm, about 6 mm, about 8 mm, about 10 mm or more, but generally less than about 15 mm or 12 mm or less depending upon the intended target vessel. In some embodiments (e.g., when the distal filter assembly 1312 is configured to be positioned in the left subclavian artery 16), the diameter may be between about 7 mm and about 12 mm (e.g., about 7 mm, about 8 mm, about 9 mm, about 10 mm, about 11 mm, about 12 mm, ranges between such values, etc.). In some embodiments (e.g., when the distal filter assembly 1312 is configured to be positioned in the left vertebral artery 24), the diameter may be between about 2 mm and about 4.5 mm (e.g., about 2 mm, about 2.5 mm, about 3 mm, about 3.5 mm, about 4 mm, about 4.5 mm, ranges between such values, etc.). Other diameters or other types of lateral dimensions are also possible. Different diameters can allow treatment of a selection of subjects having different vessel sizes.

The filter assembly 1312 may have a maximum length from a proximal limit of the frame 1316 to the distal end or point of convergence 1326 with the inner member 1306. The length can be between about 7 mm and about 50 mm (e.g., at least about 7 mm, about 8 mm, about 10 mm, about 12 mm, 16 mm, about 20 mm or more, but generally less than about 40 mm or 30 mm or 20 mm or less depending upon the intended target vessel. Other lengths are also possible, for example based on the diameter or effective diameter. For example, the length of the distal filter assembly 1312 may increase as the diameter increases, and the length of the distal filter assembly 1312 may decrease as the diameter decreases.

In the illustrated embodiment, as described herein, the distal filter assembly 1312 comprises a self-expanding support such as hoop or frame 1316 which supports the open proximal end of an approximately conical filter membrane 1318. A support strut may be provided to connect the frame 1316 to a portion of the device 1300 such as the inner member 1306, to facilitate resheathing of the filter assembly 1312 and also to orientate the hoop or frame 1316. In the illustrated embodiment, the distal filter assembly 1312 may function both to filter blood entering the left subclavian artery 16, and also to anchor the system.

Continued proximal actuation of the outer sheath 1304 while fixing the inner member 1306 relative to the handle may then deploy the aortic arch component or proximal filter assembly 1320, as shown in FIG. 15. It is contemplated that distal end 1308 of the outer sheath 1304 may be withdrawn into the innominate artery 12 or the right subclavian artery 22 to fully expose the proximal filter assembly 1320. As the outer sheath 1304 is withdrawn, the distal filter assembly 1312 remains in the left subclavian artery 16, supported by the inner member 1306 and helping to anchor the proximal filter assembly 1320.

The proximal filter assembly 1320 may include an aortic ring 1328 or support element and a filter membrane or filter element 1314. The aortic ring 1328 may be similar in form and function to the frame 1316 of the distal filter assembly 1312, although larger in scale. Similarly, the filter element 1314 may be similar in form and function to the filter element 1318 described herein. The aortic ring 1328 generally provides expansion support to the filter element 1314 in its expanded configuration, while the filter element 1314 is adapted to filter fluid, such as blood, and trap particles flowing therethrough. The aortic ring 1328 may include an approximately elliptical hoop of a shape memory wire such as nitinol. The aortic ring 1328 may be configured to engage the wall of the aorta and seal against the roof of the aortic arch 10 outside of the ostia of all three great vessels 12, 14, 16 to isolate the cerebral vasculature. For example, the aortic ring 1328 may be sized and shaped such that it extends from the ostium of the left subclavian artery 16 to the ostium of the innominate artery 12. The center 1330 of the aortic ring 1328 is open to allow blood and debris to enter the device 1320, and the ring 1328 is attached around its perimeter to the filter element 1314. A proximal end of the filter element 1314 may be coupled to or extend into a distal end 1308 of the outer sheath 1304. The aortic ring 1328 may be self-expanding such that as the outer sheath 1304 is proximally withdrawn, the aortic ring 1328 automatically expands, although this is not required. The aortic ring 1328 may be coupled to different portions of the protection device 1300. In some embodiments, the aortic ring 1328 may further include one or more support connectors 1332 extending between the aortic ring 1328 and the distal frame 1316. The support connector 1332 may help to improve apposition by offering additional support to both the distal frame 1316 and the aortic ring 1328.

Once the proximal filter assembly 1320 has been deployed, the inner member 1306 may be retracted to minimize intrusion into the aorta 10. The position of the inner member 1306 may be adjusted using a control at the handle. The mechanism coupling the proximal filter 1320 to the device 1300 may be adjusted by proximally retracting or distally advancing the handle to ensure the proximal filter 1320 is fully deployed, the aortic ring 1328 is apposed to the roof of the aortic arch 10, and the inner member 1306 is pulled up against the roof of the aortic arch 10 to ensure that the filter element 1314 is fully against the roof of the arch 10. The proximal filter assembly 1320 is thus positioned to protect the cerebral vasculature 14, 18, 20, 24 from embolic debris during an endovascular procedure such as TAVR.

Once the protection device 1300 has been deployed, the TAVR, or other index procedure, may be performed. Once the index procedure is contemplate, the inner member 1306 may be advanced relative to the handle to apply tension to the proximal filter element 1314 and/or the distal filter element 1318. The outer sheath 1304 may then be advanced relative to the handle, while fixing the position of the inner member 1306 relative to the handle, until the proximal filter assembly 1320 and the distal filter assembly 1312 are fully sheathed. The protection device 1300 may then be removed from the introducer sheath.

Figure 16:
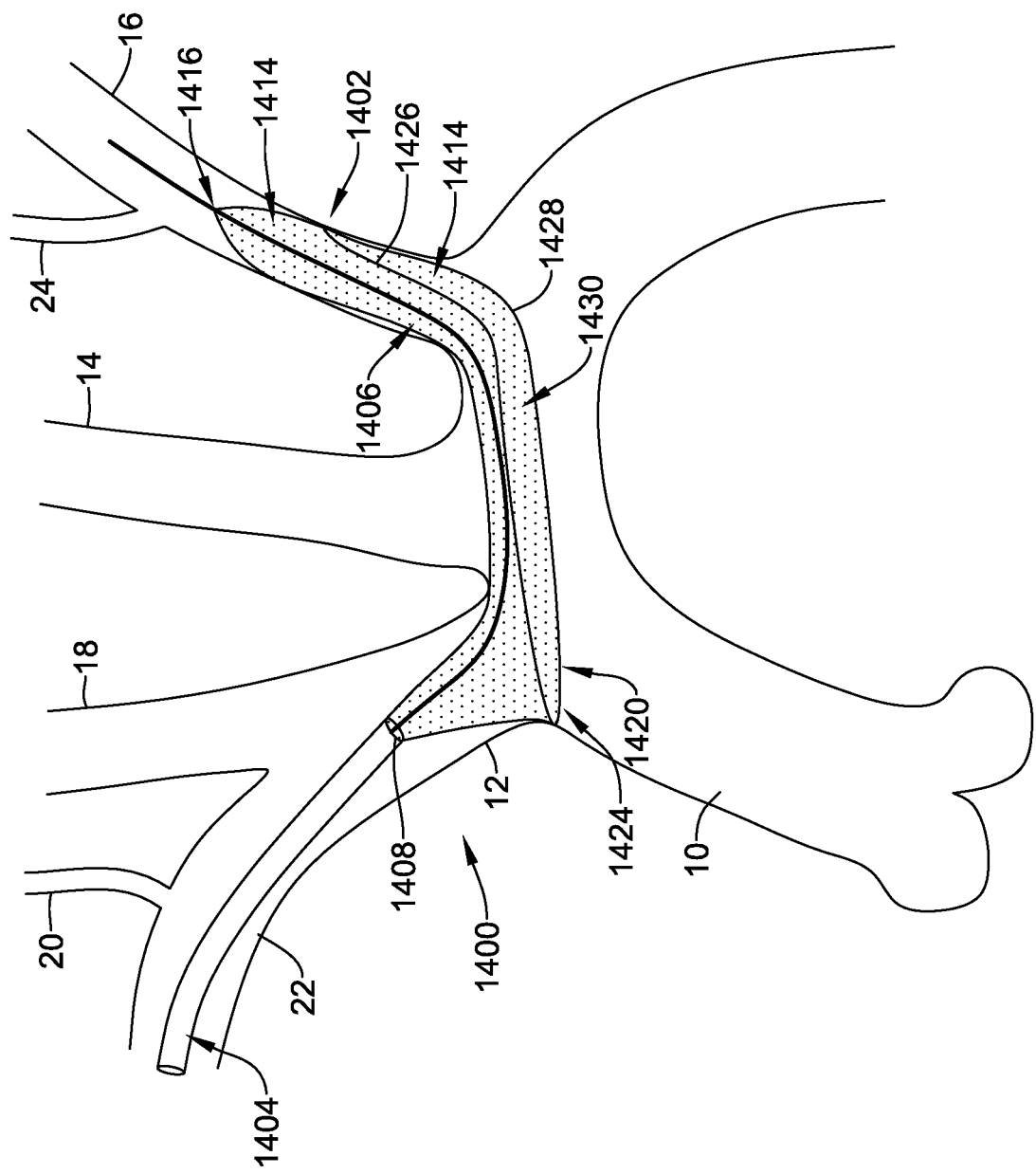
FIG. 16 illustrates another alternative embodiment of a protection device.

FIG. 16 illustrates a schematic view of another illustrative protection device 1400 in an expanded configuration within the aortic arch 10. The protection device 1400 may be configured to be introduced through the brachiocephalic or innominate artery 12 via the right radial or right brachial artery, and across the aortic arch 10. Generally, a distal portion 1402 of the catheter is anchored in the left subclavian artery 16, and a membrane or filter element 1414 is deployed such that the protection device 1400 isolates all three of the left subclavian, left common carotid and brachiocephalic arteries 16, 14, 12 from embolic debris that might flow through the aortic arch 10. It is contemplated that features of the protection device 1400 described herein can be differently combined to form additional embodiments. All embodiments shown may also be introduced into the left radial or brachial artery, with the distal portion of the catheter anchored in the brachiocephalic artery 12.

The protection device 1400 comprises a proximal portion (not explicitly shown) and a distal portion 1402. The proximal portion is configured to be held and manipulated by a user such as a surgeon. In some cases, the proximal portion may be coupled to a handle configured to facilitate delivery and deployment of the device 1400. In some cases, the handle of the protection device 1400 may be similar in form and function to the handles 40, 106 described herein. The distal portion 1402 is configured to be positioned at a target location such as the left subclavian artery 16. When the distal portion 1402 is configured to be positioned at the left subclavian artery 16, the location may be upstream of the left vertebral artery 24 such that the blood is filtered prior to entering the left vertebral artery 24, although this is not required.

Generally, the protection system 1400 may include an outer sheath 1404, an inner member 1406, and a filter assembly 1420. The inner member 1406 and the outer sheath 1404 may be configured to extend from the proximal end region to the distal end region 1402 of the protection device 1400. The outer sheath 1404 and the inner member 1406 may be guided over a guidewire (not explicitly shown), or along the guidewire (in a rapid exchange configuration) to position a distal end of the outer sheath 1404 within the left subclavian artery 16. The inner member 1406 may be radially inward of the outer sheath 1404 and separately actuatable therefrom (e.g., slidably disposed within a lumen of the outer sheath 1404).

To position the protection device 1400 within the body, an incision may be made in the subject's right radial artery, or alternatively the right brachial artery. An introducer (not explicitly shown) may be placed into the incision and the protection device 1400 inserted into the introducer. The protection device 1400 may be advanced through the vasculature in a delivery configuration in which the filter assembly 1420 is collapsed or sheathed within the outer sheath 1404. The outer sheath 1404, inner member 1406, and the filter assembly 1420 may be advanced over a guidewire (if so provided) to the target location. In some cases, the guidewire may be positioned at the target location and the outer sheath 1404, inner member 1406, and the filter assembly 1420 subsequently advanced over the guidewire to the target location. In other instances, the guidewire and the outer sheath 1404, inner member 1406, and the filter assembly 1420 may be advanced substantially simultaneously with the guidewire leading (e.g., positioned most distal to) the outer sheath 1404, inner member 1406, and the filter assembly 1420.

The delivery catheter or outer sheath 1404 may have a diameter sized to navigate the vasculature from the incision to the target location. An outer sheath 1404 sized for right radial access may have a diameter in the range of about 6 French (F). An outer sheath 1404 sized for femoral access may be larger, although this is not required. These are just some examples. In some cases, the outer sheath 1404 (or other components of the protection device 1400) may include deflectable tip or an articulatable distal tip. It is contemplated that the distal tip of the outer sheath 1404 may be deflected (e.g., using a handle) to facilitate navigation of the device 1400 through the vasculature and cannulation of the target vessel. In some cases, the deflectable tip may be configured to deflect by about 90°. However, the tip of the outer sheath 1404 may be made to deflect by less than 90 or more than 90, as desired. The deflection may be controlled by a rotating knob at the handle, or the control mechanism. In some cases, the outer sheath 1404 may include a pre-shaped and/or non-deflectable tip.

The filter assembly 1420 may comprise a self-expanding filter assembly (e.g., comprising a superelastic material with stress-induced martensite due to confinement in the outer sheath 1404). The filter assembly 1420 may comprise a shape-memory material configured to self-expand upon a temperature change (e.g., heating to body temperature). The filter assembly 1420 may comprise a shape-memory or superelastic frame 1428 (e.g., comprising a nitinol hoop) and a microporous filter element 1414 (e.g., comprising a polymer including laser-drilled holes) coupled to the frame, for example similar to the filter assemblies described in U.S. Pat. No. 8,876,796.

The frame 1428 may generally provide expansion support to the filter element 1414 in the expanded state. In the expanded state, the filter element 1414 is configured to filter fluid (e.g., blood) flowing through the filter element 1414 and to inhibit or prevent particles (e.g., embolic material) from flowing through the filter element 1414 by capturing the particles in the filter element 1414. The frame 1428 may be configured to engage the wall of the aorta and seal against the roof of the aortic arch 10 outside of the ostia of all three great vessels 12, 14, 16 to isolate the cerebral vasculature. The frame 1428 may be similar in form and function to the end rings 124, 126 described herein. For example, the frame 1428 may be formed from similar materials, wire shapes, sizes, etc., as the end rings 124, 126. Similarly, the filter element 1414 may be similar in form and function to the filter element 128 described herein.

The frame 1428 may include a radiopaque marker such as a small coil wrapped around or coupled to the hoop to aid in visualization under fluoroscopy. In some embodiments, the frame 1428 may comprise a shape other than a hoop, for example, a spiral. In some embodiments, the filter assembly 1420 may not include or be substantially free of a frame.

The left subclavian artery 16 may be cannulated through a combination of advancing and torqueing the catheter or outer sheath 1404. In some cases, the left subclavian artery 16 may first be cannulated using the guidewire. It is contemplated that in some cases, the deflection of the catheter tip may be relaxed to advance the outer sheath 1404 into the left subclavian artery 16. Once the protection device 1400 (e.g., the distal end 1408 of the outer sheath 1404) has been advanced to the target location, which in the illustrated embodiment may be the left subclavian artery 16, the outer sheath 1404 may be proximally retracted to expose a distal end region 1416 of a filter element 1414 of the filter assembly 1420 beyond the distal end 1408 of the outer sheath 1404. Alternatively, or additionally, the inner member 1406 may be distally advanced to deploy the distal end region 1416 of the filter element 1414. The distal end region 1416 of the filter element 1414 may be coupled to or otherwise affixed to the inner member 1406. The inner member 1406 may be advanced into and held in position within the left subclavian artery 16. In some embodiments, an anchoring device (not explicitly shown) may be coupled to the inner member 1406 to help maintain the position of the inner member 1406. The anchoring device may be an expandable frame or other structure. The distal end region 1416 of the filter element 1414 may be configured to be deployed in the distal-most great vessel relative to the location of the incision. For example, when right radial access is used, the distal-most great vessel is the left subclavian artery 16. However, if left radial access is used, the distal-most great vessel is the innominate artery 12.

Continued proximal retraction of the outer sheath 1404 while fixing the inner member 1406 relative to the handle may deploy a distal portion 1426 of a support frame 1428 within the left subclavian artery 16. Said differently, the support frame 1428 may be angled to extend from the aorta 10 to the left subclavian artery 16. Additional continued proximal actuation of the outer sheath 1404 while fixing the inner member 1406 relative to the handle may then deploy the proximal portion 1424 of the filter assembly 1420. Said differently, the support frame 1428 may be angled to extend from the aorta 10 to the left subclavian artery 16. It is contemplated that distal end 1408 of the outer sheath 1404 may be withdrawn into the innominate artery 12 or the right subclavian artery 22 to fully expose the filter assembly 1420. As the outer sheath 1404 is withdrawn, the distal portion 1416 of the filter element 1414 remains in the left subclavian artery 16, supported by the inner member 1406 and helping to anchor the filter assembly 1420.

The frame 1428 generally provides expansion support to the filter element 1414 in its expanded configuration, while the filter element 1414 is adapted to filter fluid, such as blood, and trap particles flowing therethrough. The frame 1428 may include an approximately elliptical hoop of a shape memory wire such as nitinol. The frame 1428 may be configured to engage the wall of the aorta and seal against the roof of the aortic arch 10 outside of the ostia of all three great vessels 12, 14, 16 to isolate the cerebral vasculature. For example, the frame 1428 may be sized and shaped such that it extends from the ostium of the left subclavian artery 16 to the ostium of the innominate artery 12. The center 1430 of the frame 1428 is open to allow blood and debris to enter the device 1420, and the ring 1428 is attached around its perimeter to the filter element 1414. A proximal end of the filter element 1414 may be coupled to or extend into a distal end 1408 of the outer sheath 1404. The frame 1428 may be self-expanding such that as the outer sheath 1404 is proximally withdrawn, the frame 1428 automatically expands, although this is not required. The frame 1428 may be coupled to different portions of the protection device 1400. In some embodiments, the frame 1428 may further include one or more support connectors extending between the frame 1428 and the distal portion 1416. The support connector may help to improve apposition by offering additional support to both the distal portion 1416 and the frame 1428.

Once the filter assembly 1420 has been deployed, the inner member 1406 may be retracted to minimize intrusion into the aorta 10. The position of the inner member 1406 may be adjusted using a control at the handle. The mechanism coupling the proximal filter 1420 to the device 1400 may be adjusted by proximally retracting or distally advancing the handle to ensure the proximal filter 1420 is fully deployed, the frame 1428 is apposed to the roof of the aortic arch 10, and the inner member 1406 is pulled up against the roof of the aortic arch 10 to ensure that the filter element 1414 is fully against the roof of the arch 10. The filter assembly 1420 is thus positioned to protect the cerebral vasculature 14, 18, 20, 24 from embolic debris during an endovascular procedure such as TAVR. It is contemplated that positioning the distal portion 1426 of the frame 1428 in the left subclavian artery 16 may decrease the chance of interaction between the frame 1428 and anything passing through the aortic arch 10, such as, but not limited to a TAVR delivery catheter.

Once the protection device 1400 has been deployed, the TAVR, or other index procedure, may be performed. Once the index procedure is contemplate, the inner member 1406 may be advanced relative to the handle to apply tension to the proximal filter element 1414 and/or the distal filter element 1418. The outer sheath 1404 may then be advanced relative to the handle, while fixing the position of the inner member 1406 relative to the handle, until the filter assembly 1420 is fully sheathed. The protection device 1400 may then be removed from the introducer sheath.

Figure 17:
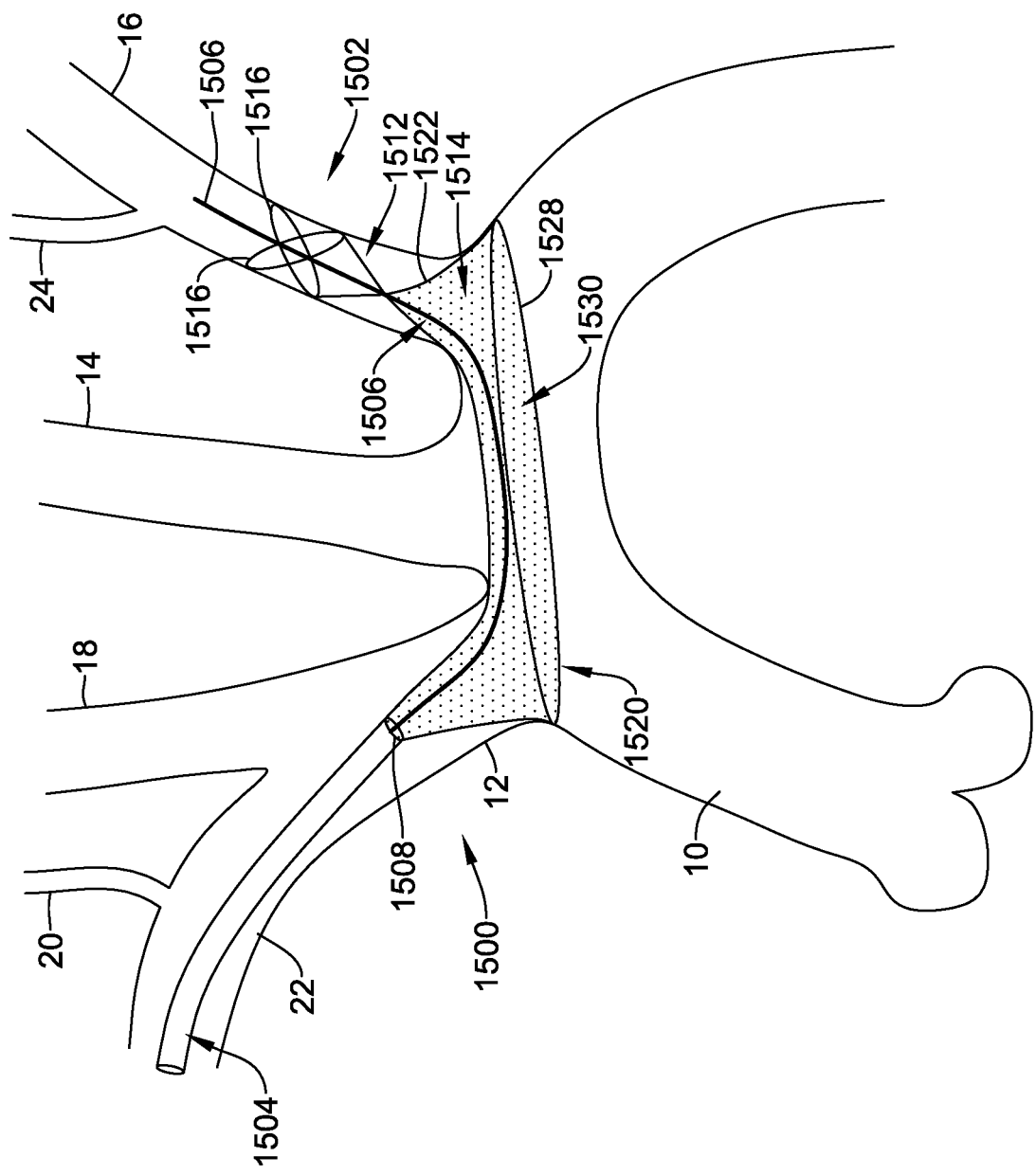
FIG. 17 illustrates another alternative embodiment of a protection device.
Figure 18:
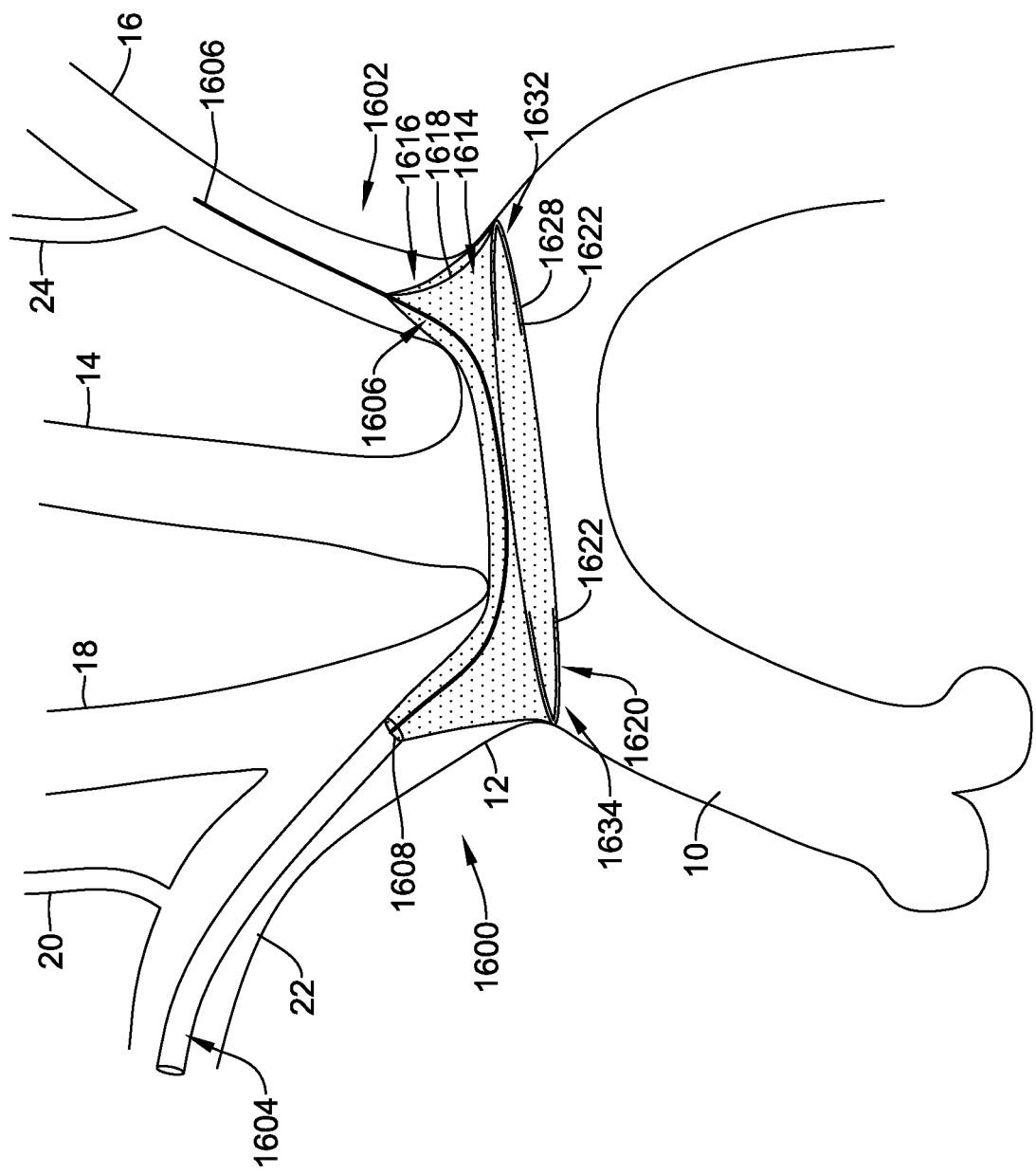
FIG. 18 illustrates another alternative embodiment of a protection device.

FIG. 17 illustrates a schematic view of another illustrative protection device 1500 in an expanded configuration within the aortic arch 10. The protection device 1500 may be configured to be introduced through the brachiocephalic or innominate artery 12 via the right radial or right brachial artery, and across the aortic arch 10. Generally, a distal portion 1502 of the catheter is anchored in the left subclavian artery 16, and a membrane or filter element 1514 is deployed such that the protection device 1500 isolates all three of the left subclavian, left common carotid and brachiocephalic arteries 16, 14, 12 from embolic debris that might flow through the aortic arch 10. It is contemplated that features of the protection device 1500 described herein can be differently combined to form additional embodiments. All embodiments shown may also be introduced into the left radial or brachial artery, with the distal portion of the catheter anchored in the brachiocephalic artery 12.

The protection device 1500 comprises a proximal portion (not explicitly shown) and a distal portion 1502. The proximal portion is configured to be held and manipulated by a user such as a surgeon. In some cases, the proximal portion may be coupled to a handle configured to facilitate delivery and deployment of the device 1500. In some cases, the handle of the protection device 1500 may be similar in form and function to the handles 40, 106 described herein. The distal portion 1502 is configured to be positioned at a target location such as the left subclavian artery 16. When the distal portion 1502 is configured to be positioned at the left subclavian artery 16, the location may be upstream of the left vertebral artery 24 such that the blood is filtered prior to entering the left vertebral artery 24, although this is not required.

Generally, the protection system 1500 may include an outer sheath 1504, an inner member 1506, a distal anchoring structure 1512, and a filter assembly 1520. The inner member 1506 and the outer sheath 1504 may be configured to extend from the proximal end region to the distal end region 1502 of the protection device 1500. The outer sheath 1504 and the inner member 1506 may be guided over a guidewire (not explicitly shown), or along the guidewire (in a rapid exchange configuration) to position a distal end of the outer sheath 1504 within the left subclavian artery 16. The inner member 1506 may be radially inward of the outer sheath 1504 and separately actuatable therefrom (e.g., slidably disposed within a lumen of the outer sheath 1504).

To position the protection device 1500 within the body, an incision may be made in the subject's right radial artery, or alternatively the right brachial artery. An introducer (not explicitly shown) may be placed into the incision and the protection device 1500 inserted into the introducer. The protection device 1500 may be advanced through the vasculature in a delivery configuration in which the distal anchoring structure 1512 and the filter assembly 1520 are collapsed or sheathed within the outer sheath 1504. The outer sheath 1504, inner member 1506, the distal anchoring structure 1512, and the filter assembly 1520 may be advanced over a guidewire (if so provided) to the target location. In some cases, the guidewire may be positioned at the target location and the outer sheath 1504, inner member 1506, distal anchoring structure 1512, and the filter assembly 1520 subsequently advanced over the guidewire to the target location. In other instances, the guidewire and the outer sheath 1504, inner member 1506, and distal anchoring structure 1512, and the filter assembly 1520 may be advanced substantially simultaneously with the guidewire leading (e.g., positioned most distal to) the outer sheath 1504, inner member 1506, distal anchoring structure 1512, and the filter assembly 1520.

The delivery catheter or outer sheath 1504 may have a diameter sized to navigate the vasculature from the incision to the target location. An outer sheath 1504 sized for right radial access may have a diameter in the range of about 6 French (F). An outer sheath 1504 sized for femoral access may be larger, although this is not required. These are just some examples. In some cases, the outer sheath 1504 (or other components of the protection device 1500) may include deflectable tip or an articulatable distal tip. It is contemplated that the distal tip of the outer sheath 1504 may be deflected (e.g., using a handle) to facilitate navigation of the device 1500 through the vasculature and cannulation of the target vessel. In some cases, the deflectable tip may be configured to deflect by about 90°. However, the tip of the outer sheath 1504 may be made to deflect by less than 90 or more than 90, as desired. The deflection may be controlled by a rotating knob at the handle, or the control mechanism. In some cases, the outer sheath 1504 may include a pre-shaped and/or non-deflectable tip.

The left subclavian artery 16 may be cannulated through a combination of advancing and torqueing the catheter 1504. In some cases, the left subclavian artery 16 may first be cannulated using the guidewire. It is contemplated that in some cases, the deflection of the catheter tip may be relaxed to advance the outer sheath 1504 into the left subclavian artery 16. Once the protection device 1500 (e.g., the distal end 1508 of the outer sheath 1504) has been advanced to the target location, which in the illustrated embodiment may be the left subclavian artery 16, the outer sheath 1504 may be proximally retracted to expose a distal anchoring structure 1512 beyond the distal end 1508 of the outer sheath 1504. Alternatively, or additionally, the inner member 1506 may be distally advanced to deploy the distal anchoring structure 1512. The distal anchoring structure 1512 may be configured to be deployed in the distal-most great vessel relative to the location of the incision. For example, when right radial access is used, the distal-most great vessel is the left subclavian artery 16. However, if left radial access is used, the distal-most great vessel is the innominate artery 12.

The distal anchoring structure 1512 may comprise one or more self-expanding rings 1516 (e.g., comprising a superelastic material with stress-induced martensite due to confinement in the outer sheath 1504). The distal anchoring structure 1512 may comprise a shape-memory material configured to self-expand upon a temperature change (e.g., heating to body temperature). The distal anchoring structure 1512 may help anchor the distal end of the inner member 1506 in the left subclavian artery 16. In some cases, the distal anchoring structure 1512 may also anchor the filter assembly 1520. The anchoring mechanism 1512 may include a filter membrane or may lack a filter membrane, as desired. Other anchoring mechanisms may be provided in addition to or alternatively to the distal anchoring structure 1512. The rings 1516 may be similar in form and function to the end rings 124, 126 described herein. For example, the rings 1516 may be formed from similar materials, wire shapes, sizes, etc., as the end rings 124, 126. The distal anchoring structure 1512 may be coupled to the inner member 1506 adjacent a distal end region thereof.

The distal anchoring structure 1512 may include a radiopaque marker such as a small coil wrapped around or coupled to the hoop to aid in visualization under fluoroscopy. In some embodiments, the distal anchoring structure 1512 may comprise a shape other than a hoop or ring, for example, a spiral. In some embodiments, the distal anchoring structure 1512 may not include or be substantially free of a frame and may include another expandable component, such as, but not limited to, an expandable balloon.

Continued proximal actuation of the outer sheath 1504 while fixing the inner member 1506 relative to the handle may then deploy the aortic arch component or filter assembly 1520, as shown in FIG. 17. It is contemplated that distal end 1508 of the outer sheath 1504 may be withdrawn into the innominate artery 12 or the right subclavian artery 22 to fully expose the filter assembly 1520. As the outer sheath 1504 is withdrawn, the distal anchoring structure 1512 remains in the left subclavian artery 16, supported by the inner member 1506 and helping to anchor the filter assembly 1520.

The filter assembly 1520 may include an aortic ring 1528 or support element and a filter membrane or filter element 1514. The aortic ring 1528 may be similar in form and function to the rings 1516 of the distal anchoring structure 1512, although larger in scale. Similarly, the filter element 1514 may be similar in form and function to the filter element 128 described herein. The aortic ring 1528 generally provides expansion support to the filter element 1514 in its expanded configuration, while the filter element 1514 is adapted to filter fluid, such as blood, and trap particles flowing therethrough. The aortic ring 1528 may include an approximately elliptical hoop of a shape memory wire such as nitinol. The aortic ring 1528 may be configured to engage the wall of the aorta and seal against the roof of the aortic arch 10 outside of the ostia of all three great vessels 12, 14, 16 to isolate the cerebral vasculature. For example, the aortic ring 1528 may be sized and shaped such that it extends from the ostium of the left subclavian artery 16 to the ostium of the innominate artery 12. The center 1530 of the aortic ring 1528 is open to allow blood and debris to enter the filter 1520, and the ring 1528 is attached around its perimeter to the filter element 1514. A proximal end of the filter element 1514 may be coupled to or extend into a distal end 1508 of the outer sheath 1504. A distal end 1522 of the filter element 1514 may be coupled to the inner member 1506. It is contemplated that the distal end 1522 maybe coupled to the inner member 1506 proximal to the distal anchoring structure 1512. For example, the distal anchoring structure 1512 could be placed distal to the filter element 1514 as shown in FIG. 17. In other embodiments, the distal anchoring structure 1512 may be placed in the filter element 1514 similar to the protection device 1300 in FIG. 15.

The aortic ring 1528 may be self-expanding such that as the outer sheath 1504 is proximally withdrawn, the aortic ring 1528 automatically expands, although this is not required. The aortic ring 1528 may be coupled to different portions of the protection device 1500.

Once the filter assembly 1520 has been deployed, the inner member 1506 may be retracted to minimize intrusion into the aorta 10. The position of the inner member 1506 may be adjusted using a control at the handle. The mechanism coupling the proximal filter 1520 to the device 1500 may be adjusted by proximally retracting or distally advancing the handle to ensure the proximal filter 1520 is fully deployed, the aortic ring 1528 is apposed to the roof of the aortic arch 10, and the inner member 1506 is pulled up against the roof of the aortic arch 10 to ensure that the filter element 1514 is fully against the roof of the arch 10. The filter assembly 1520 is thus positioned to protect the cerebral vasculature 14, 18, 20, 24 from embolic debris during an endovascular procedure such as TAVR.

Once the protection device 1500 has been deployed, the TAVR, or other index procedure, may be performed. Once the index procedure is contemplate, the inner member 1506 may be advanced relative to the handle to apply tension to the proximal filter element 1514 and/or the distal filter element 1218. The outer sheath 1504 may then be advanced relative to the handle, while fixing the position of the inner member 1506 relative to the handle, until the filter assembly 1520 and the distal anchoring structure 1512 are fully sheathed. The protection device 1500 may then be removed from the introducer sheath.

FIG. 16 illustrates a schematic view of another illustrative protection device 1600 in an expanded configuration within the aortic arch 10. The protection device 1600 may be configured to be introduced through the brachiocephalic or innominate artery 12 via the right radial or right brachial artery, and across the aortic arch 10. Generally, a distal portion 1602 of the catheter is anchored in the left subclavian artery 16, and a membrane or filter element 1614 is deployed such that the protection device 1600 isolates all three of the left subclavian, left common carotid and brachiocephalic arteries 16, 14, 12 from embolic debris that might flow through the aortic arch 10. It is contemplated that features of the protection device 1600 described herein can be differently combined to form additional embodiments. All embodiments shown may also be introduced into the left radial or brachial artery, with the distal portion of the catheter anchored in the brachiocephalic artery 12.

The protection device 1600 comprises a proximal portion (not explicitly shown) and a distal portion 1602. The proximal portion is configured to be held and manipulated by a user such as a surgeon. In some cases, the proximal portion may be coupled to a handle configured to facilitate delivery and deployment of the device 1600. In some cases, the handle of the protection device 1600 may be similar in form and function to the handles 40, 106 described herein. The distal portion 1602 is configured to be positioned at a target location such as the left subclavian artery 16. When the distal portion 1602 is configured to be positioned at the left subclavian artery 16, the location may be upstream of the left vertebral artery 24 such that the blood is filtered prior to entering the left vertebral artery 24, although this is not required.

Generally, the protection system 1600 may include an outer sheath 1604, an inner member 1606, and a filter assembly 1620. The inner member 1606 and the outer sheath 1604 may be configured to extend from the proximal end region to the distal end region 1602 of the protection device 1600. The outer sheath 1604 and the inner member 1606 may be guided over a guidewire (not explicitly shown), or along the guidewire (in a rapid exchange configuration) to position a distal end of the outer sheath 1604 within the left subclavian artery 16. The inner member 1606 may be radially inward of the outer sheath 1604 and separately actuatable therefrom (e.g., slidably disposed within a lumen of the outer sheath 1604).

To position the protection device 1600 within the body, an incision may be made in the subject's right radial artery, or alternatively the right brachial artery. An introducer (not explicitly shown) may be placed into the incision and the protection device 1600 inserted into the introducer. The protection device 1600 may be advanced through the vasculature in a delivery configuration in which the filter assembly 1620 is collapsed or sheathed within the outer sheath 1604. The outer sheath 1604, inner member 1606, and the filter assembly 1620 may be advanced over a guidewire (if so provided) to the target location. In some cases, the guidewire may be positioned at the target location and the outer sheath 1604, inner member 1606, and the filter assembly 1620 subsequently advanced over the guidewire to the target location. In other instances, the guidewire and the outer sheath 1604, inner member 1606, and the filter assembly 1620 may be advanced substantially simultaneously with the guidewire leading (e.g., positioned most distal to) the outer sheath 1604, inner member 1606, and the filter assembly 1620.

The delivery catheter or outer sheath 1604 may have a diameter sized to navigate the vasculature from the incision to the target location. An outer sheath 1604 sized for right radial access may have a diameter in the range of about 6 French (F). An outer sheath 1604 sized for femoral access may be larger, although this is not required. These are just some examples. In some cases, the outer sheath 1604 (or other components of the protection device 1600) may include deflectable tip or an articulatable distal tip. It is contemplated that the distal tip of the outer sheath 1604 may be deflected (e.g., using a handle) to facilitate navigation of the device 1600 through the vasculature and cannulation of the target vessel. In some cases, the deflectable tip may be configured to deflect by about 90°. However, the tip of the outer sheath 1604 may be made to deflect by less than 90 or more than 90, as desired. The deflection may be controlled by a rotating knob at the handle, or the control mechanism. In some cases, the outer sheath 1604 may include a pre-shaped and/or non-deflectable tip.

The filter assembly 1620 may comprise a self-expanding filter assembly (e.g., comprising a superelastic material with stress-induced martensite due to confinement in the outer sheath 1604). The filter assembly 1620 may comprise a shape-memory material configured to self-expand upon a temperature change (e.g., heating to body temperature). The filter assembly 1620 may comprise a shape-memory or superelastic frame 1628 (e.g., comprising a nitinol hoop) and a microporous filter element 1614 (e.g., comprising a polymer including laser-drilled holes) coupled to the frame, for example similar to the filter assemblies described in U.S. Pat. No. 8,876,796.

The frame 1620 may generally provide expansion support to the filter element 1614 in the expanded state. In the expanded state, the filter element 1614 is configured to filter fluid (e.g., blood) flowing through the filter element 1614 and to inhibit or prevent particles (e.g., embolic material) from flowing through the filter element 1614 by capturing the particles in the filter element 1614. The frame 1628 may be configured to engage the wall of the aorta and seal against the roof of the aortic arch 10 outside of the ostia of all three great vessels 12, 14, 16 to isolate the cerebral vasculature. The frame 1628 may be similar in form and function to the end rings 124, 126 described herein. For example, the frame 1628 may be formed from similar materials, wire shapes, sizes, etc., as the end rings 124, 126. Similarly, the filter element 1614 may be similar in form and function to the filter element 128 described herein.

The frame 1628 may include a radiopaque marker such as a small coil wrapped around or coupled to the hoop to aid in visualization under fluoroscopy. In some embodiments, the frame 1628 may comprise a shape other than a hoop, for example, a spiral. In some embodiments, the filter assembly 1620 may not include or be substantially free of a frame.

The left subclavian artery 16 may be cannulated through a combination of advancing and torqueing the catheter or outer sheath 1604. In some cases, the left subclavian artery 16 may first be cannulated using the guidewire. It is contemplated that in some cases, the deflection of the catheter tip may be relaxed to advance the outer sheath 1604 into the left subclavian artery 16. Once the protection device 1600 (e.g., the distal end 1608 of the outer sheath 1604) has been advanced to the target location, which in the illustrated embodiment may be the left subclavian artery 16, the outer sheath 1604 may be proximally retracted to expose a distal end region 1616 of a filter element 1614 of the filter assembly 1620 beyond the distal end 1608 of the outer sheath 1604. Alternatively, or additionally, the inner member 1606 may be distally advanced to deploy the distal end region 1616 of the filter element 1614. The distal end region 1616 of the filter element 1614 may be coupled to or otherwise affixed to the inner member 1606. The inner member 1606 may be advanced into and held in position within the left subclavian artery 16. In some embodiments, an anchoring device (not explicitly shown) may be coupled to the inner member 1606 to help maintain the position of the inner member 1606. The anchoring device may be an expandable frame or other structure. The distal end region 1616 of the filter element 1614 may be configured to be deployed in the distal-most great vessel relative to the location of the incision. For example, when right radial access is used, the distal-most great vessel is the left subclavian artery 16. However, if left radial access is used, the distal-most great vessel is the innominate artery 12. A support leg 1618 may extend between the distal end region 1616 of the filter element 1614 and the frame 1628. The support leg 1618 may offer additional support to the distal end of the support frame 1628, increasing stability. The support leg 1618 could be attached to the inner member 1606, distal anchor (if so provided), or the filter element 1614 itself.

Continued proximal retraction of the outer sheath 1606 while fixing the inner member 1606 relative to the handle may deploy the support frame 1628. It is contemplated that distal end 1608 of the outer sheath 1604 may be withdrawn into the innominate artery 12 or the right subclavian artery 22 to fully expose the filter assembly 1620. As the outer sheath 1604 is withdrawn, the distal portion 1616 of the filter element 1614 remains in the left subclavian artery 16, supported by the inner member 1606 and helping to anchor the filter assembly 1620.

The frame 1628 generally provides expansion support to the filter element 1614 in its expanded configuration, while the filter element 1614 is adapted to filter fluid, such as blood, and trap particles flowing therethrough. The frame 1628 may include an approximately elliptical hoop of a shape memory wire such as nitinol. The frame 1628 may be configured to engage the wall of the aorta and seal against the roof of the aortic arch 10 outside of the ostia of all three great vessels 12, 14, 16 to isolate the cerebral vasculature. For example, the frame 1628 may be sized and shaped such that it extends from the ostium of the left subclavian artery 16 to the ostium of the innominate artery 12. The center 1630 of the frame 1628 is open to allow blood and debris to enter the device 1620, and the ring 1628 is attached around its perimeter to the filter element 1614. A proximal end of the filter element 1614 may be coupled to or extend into a distal end 1608 of the outer sheath 1604. The frame 1628 may be self-expanding such that as the outer sheath 1604 is proximally withdrawn, the frame 1628 automatically expands, although this is not required. The frame 1628 may be coupled to different portions of the protection device 1600. In some embodiments, the filter assembly 1620 may further include one or more support structures 1622 added around the filter element 1614. In some embodiments, the support structures 1622 may be positioned to reinforce the frame at the hinge points of the frame 1628 which may improve apposition by reinforcing the fold points of the frame 1628, giving better overall hoop strength. The support structures 1622 may be generally curved structures positioned at the distal and proximal ends 1632, 1634 of the support frame 1628. However, other configurations and/or position may be used, as desired.

Once the filter assembly 1620 has been deployed, the inner member 1606 may be retracted to minimize intrusion into the aorta 10. The position of the inner member 1606 may be adjusted using a control at the handle. The mechanism coupling the proximal filter 1620 to the device 1600 may be adjusted by proximally retracting or distally advancing the handle to ensure the proximal filter 1620 is fully deployed, the frame 1628 is apposed to the roof of the aortic arch 10, and the inner member 1606 is pulled up against the roof of the aortic arch 10 to ensure that the filter element 1614 is fully against the roof of the arch 10. The filter assembly 1620 is thus positioned to protect the cerebral vasculature 14, 18, 20, 24 from embolic debris during an endovascular procedure such as TAVR. It is contemplated that positioning the distal portion 1426 of the frame 1628 in the left subclavian artery 16 may decrease the chance of interaction between the frame 1628 and anything passing through the aortic arch 10, such as, but not limited to a TAVR delivery catheter.

Once the protection device 1600 has been deployed, the TAVR, or other index procedure, may be performed. Once the index procedure is contemplate, the inner member 1606 may be advanced relative to the handle to apply tension to the proximal filter element 1614 and/or the distal anchoring mechanism (if so provided). The outer sheath 1604 may then be advanced relative to the handle, while fixing the position of the inner member 1606 relative to the handle, until the filter assembly 1620 is fully sheathed. The protection device 1600 may then be removed from the introducer sheath.

Although certain filter assemblies have been described or illustrated herein as including a filter, the filters described herein can also be a self-expanding stent, a balloon, a deflector, or other occluding device. The filter assemblies described or illustrated herein can be introduced through a right radial or right brachial artery. The filter assemblies may alternatively be introduced through a left radial or left brachial artery.

As used herein, the relative terms "proximal" and "distal" shall be defined from the perspective of the protection system. Thus, proximal refers to the direction of the handle portion of the delivery system and distal refers to the direction of the distal tip.

Conditional language used herein, such as, among others, "can," "might," "may," "e.g.," and the like, unless specifically stated otherwise, or otherwise understood within the context as used, is generally intended to convey that some embodiments include, while other embodiments do not include, certain features, elements, and/or states. Thus, such conditional language is not generally intended to imply that features, elements, blocks, and/or states are in any way required for one or more embodiments or that one or more embodiments necessarily include logic for deciding, with or without author input or prompting, whether these features, elements and/or states are included or are to be performed in any particular embodiment.

Although certain embodiments and examples have been described herein, it may be understood by those skilled in the art that many aspects of the delivery systems shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

For purposes of this disclosure, certain aspects, advantages, and novel features are described herein. It is to be understood that not necessarily all such advantages may be achieved in accordance with any particular embodiment. Thus, for example, those skilled in the art may recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

While the methods and devices described herein may be susceptible to various modifications and alternative forms, specific examples thereof have been shown in the drawings and are described in detail herein. It should be understood, however, that the inventive subject matter is not to be limited to the particular forms or methods disclosed, but, to the contrary, covers all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. In any methods disclosed herein, the acts or operations can be performed in any suitable sequence and are not necessarily limited to any particular disclosed sequence and not be performed in the order recited. Various operations can be described as multiple discrete operations in turn, in a manner that can be helpful in understanding certain embodiments; however, the order of description should not be construed to imply that these operations are order dependent. Additionally, the structures described herein can be embodied as integrated components or as separate components. For purposes of comparing various embodiments, certain aspects and advantages of these embodiments are described. Not necessarily all such aspects or advantages are achieved by any particular embodiment. Thus, for example, embodiments can be carried out in a manner that achieves or optimizes one advantage or group of advantages without necessarily achieving other advantages or groups of advantages. The methods disclosed herein may include certain actions taken by a practitioner; however, the methods can also include any third-party instruction of those actions, either expressly or by implication. For example, actions such as "deploying a self-expanding filter" include "instructing deployment of a self-expanding filter." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 7 mm" includes "7 mm." Phrases preceded by a term such as "substantially" include the recited phrase and should be interpreted based on the circumstances (e.g., as much as reasonably possible under the circumstances). For example, "substantially straight" includes "straight."

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. An embolic protection system for isolating the cerebral vasculature, the system comprising:
    a first protection device having a proximal portion configured to remain outside a body and a distal portion, the distal portion comprising:
        a proximal sheath;
        a proximal self-expanding filter assembly radially within the proximal sheath;
        a distal sheath; and
        a distal self-expanding filter assembly radially within the distal sheath;
    a second protection device having a proximal portion configured to remain outside the body and a distal portion, the distal portion comprising:
        an outer sheath;
        a wire radially within the outer sheath; and
        a third filter assembly radially within the outer sheath and coupled to the wire,
    wherein the third filter assembly of the second protection device has a generally tubular self-expanding main body portion defining a lumen extending from a distal end to a proximal end thereof.

2. The embolic protection system of claim 1, wherein the generally tubular self-expanding main body portion is configured to be positioned over an ostium of a left subclavian artery.

3. The embolic protection system of claim 1, wherein the wire is woven into the third filter assembly adjacent a distal end of the third filter assembly.

4. The embolic protection system of claim 3, wherein a distal edge of a filter element of the third filter assembly is folded proximally over the wire.

5. The embolic protection system of claim 1, wherein the wire comprises a plurality of wires each having a distal end coupled to a distal end of the third filter assembly.

6. The embolic protection system of claim 5, wherein proximal actuation of the plurality of wires is configured to invert the third filter assembly.

7. The embolic protection system of claim 1, wherein the wire is interwoven into the third filter assembly to form an expandable support structure having a first cross-sectional dimension in a first expanded configuration exterior to the outer sheath and a second cross-sectional dimension in a second collapsed configuration within the outer sheath, the second cross-sectional dimension smaller than the first cross-sectional dimension.

8. The embolic protection system of claim 7, further comprising an angiographic catheter radially within the outer sheath, wherein the angiographic catheter has an outer dimension greater than the second cross-sectional dimension of the expandable support structure.

9. The embolic protection system of claim 8, wherein a distal end of the angiographic catheter is configured to engage the expandable support structure when the expandable support structure is in the second collapsed configuration within the outer sheath.

10. An embolic protection system for isolating the cerebral vasculature, the system comprising:
    a first protection device having a proximal portion configured to remain outside a body and a distal portion, the distal portion comprising:
        a proximal sheath;
        a proximal self-expanding filter assembly radially within the proximal sheath;
        a distal sheath; and
        a distal self-expanding filter assembly radially within the distal sheath;
    a second protection device having a proximal portion configured to remain outside the body and a distal portion, the distal portion comprising:
        an outer sheath;
        an inner member radially within the outer sheath; and
        a third filter assembly radially within the outer sheath and coupled to a distal end of the inner member, the third filter assembly including an expandable support structure and a filter element,
    wherein the expandable support structure comprises a plurality of longitudinally extending legs, the filter element coupled to the plurality of longitudinally extending legs adjacent to a distal end of the filter element.

11. The embolic protection system of claim 10, wherein the expandable support structure comprises a first longitudinally extending leg, a second longitudinally extending leg, a support ring having a first portion and a second portion, and a pair of hinges movingly coupling the first and second portions of the support ring to the first and second longitudinally extending legs.

12. The embolic protection system of claim 11, wherein the support ring is coupled to the filter element adjacent to a distal end of the filter element.

13. An embolic protection system for isolating the cerebral vasculature, the system comprising:
    a first protection device having a proximal portion configured to remain outside a body and a distal portion, the distal portion comprising:
        a proximal sheath;
        a proximal self-expanding filter assembly radially within the proximal sheath;
        a distal sheath; and
        a distal self-expanding filter assembly radially within the distal sheath;
    a second protection device having a proximal portion configured to remain outside the body and a distal portion, the distal portion comprising:
        an outer sheath; and
        a third filter assembly coupled to and extending distally from a distal end of the outer sheath, the third filter assembly including an expandable support structure and a filter element,
    wherein the expandable support structure comprises a plurality of legs, a distal ring, and a pull wire, wherein a distal end of each leg of the plurality of legs is coupled to the distal ring and a proximal end of each leg of the plurality of legs is coupled to the distal end of the outer sheath.

14. The embolic protection system of claim 13, wherein a distal end of the pull wire is coupled to the distal ring and proximal actuation of the pull wire is configured to proximally displace the distal ring relative to the outer sheath and deflect the plurality of legs radially outward to expand the filter element.

15. The embolic protection system of claim 13, wherein the expandable support structure comprises a longitudinally extending leg and a distal hoop.

16. The embolic protection system of claim 15, further comprising a radially inward extending deployment member coupled to a proximal portion of the longitudinally extending leg and a pull wire coupled to the proximal portion of the longitudinally extending leg.

17. The embolic protection system of claim 16, wherein a proximal portion of the pull wire is disposed between the outer sheath and an inner liner.

\* \* \* \* \*